(12) United States Patent
Shukla et al.

(10) Patent No.: US 10,358,684 B2
(45) Date of Patent: *Jul. 23, 2019

(54) TARGETED MODIFICATION OF MALATE DEHYDROGENASE

(71) Applicants: Dow AgroSciences LLC, Indianapolis, IN (US); Sangamo BioSciences, Inc., Richmond, CA (US)

(72) Inventors: Vipula Shukla, Indianapolis, IN (US); Manju Gupta, Indianapolis, IN (US); Fyodor Urnov, Richmond, CA (US); Dmitry Y. Guschin, Gyeonggi-do (KR); Michiel Jan De Both, Wageningen (NL); Paul Bundock, Wageningen (NL); Lakshmi Sastry-Dent, Indianapolis, IN (US)

(73) Assignees: Dow AgroSciences LLC, Indianapolis, IN (US); Sangamo Therapeutics, Inc., Richmond, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/379,152

(22) Filed: Dec. 14, 2016

(65) Prior Publication Data

US 2017/0088825 A1 Mar. 30, 2017

Related U.S. Application Data

(63) Continuation of application No. 13/875,992, filed on May 2, 2013, now Pat. No. 9,523,098.

(60) Provisional application No. 61/641,776, filed on May 2, 2012, provisional application No. 61/780,512, filed on Mar. 13, 2013.

(51) Int. Cl.
*C12N 15/82* (2006.01)

(52) U.S. Cl.
CPC .. *C12Y 101/01037* (2013.01); *C12N 15/8213* (2013.01); *C12N 15/8241* (2013.01); *C12N 15/8243* (2013.01); *C12N 15/8261* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas et al. | |
| 6,200,759 B1 | 3/2001 | Dove et al. | |
| 6,242,568 B1 | 6/2001 | Barbas et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,534,261 B1 | 3/2003 | Cox et al. | |
| 6,824,978 B1 | 11/2004 | Cox et al. | |
| 6,933,113 B2 | 8/2005 | Case et al. | |
| 7,253,273 B2 | 8/2007 | Collingwood | |
| 7,888,121 B2 | 2/2011 | Urnov et al. | |
| 8,399,218 B2 | 3/2013 | Gupta et al. | |
| 9,523,098 B2 * | 12/2016 | Shukla | A01C 14/00 |
| 2003/0232410 A1 | 12/2003 | Liljedahl et al. | |
| 2005/0026157 A1 | 2/2005 | Baltimore et al. | |
| 2005/0064474 A1 | 3/2005 | Holmes et al. | |
| 2005/0208489 A1 * | 9/2005 | Carroll | A01K 67/0339 435/6.16 |
| 2006/0058190 A1 | 3/2006 | Ehrhardt et al. | |
| 2006/0063231 A1 | 3/2006 | Li et al. | |
| 2006/0188987 A1 | 8/2006 | Guschin et al. | |
| 2007/0218528 A1 | 9/2007 | Miller | |
| 2008/0131962 A1 | 6/2008 | Miller | |
| 2008/0182332 A1 | 7/2008 | Cai | |
| 2009/0068164 A1 | 3/2009 | Barbas et al. | |
| 2009/0093366 A1 | 4/2009 | Wright et al. | |
| 2009/0111119 A1 | 4/2009 | Doyon et al. | |
| 2009/0117617 A1 | 5/2009 | Holmes et al. | |
| 2009/0123626 A1 | 5/2009 | Rommens et al. | |
| 2009/0205083 A1 | 8/2009 | Gupta et al. | |
| 2009/0263900 A1 | 10/2009 | DeKelver et al. | |
| 2009/0305346 A1 | 12/2009 | Miller | |
| 2009/0305419 A1 | 12/2009 | Miller | |
| 2010/0047805 A1 | 2/2010 | Wang | |
| 2010/0199389 A1 | 8/2010 | Butler et al. | |
| 2011/0145940 A1 | 6/2011 | Voytas et al. | |
| 2011/0167521 A1 | 7/2011 | DeKelver et al. | |
| 2011/0189775 A1 | 8/2011 | Ainley et al. | |

(Continued)

FOREIGN PATENT DOCUMENTS

| | | |
|---|---|---|
| GB | 2338237 | 8/1998 |
| WO | WO 95/19431 | 7/1995 |

(Continued)

OTHER PUBLICATIONS

Nunes-Nesi et al, 2005, Plant Phys., 137:611-622.*
Lloyd et al, 2005, PNAS, 102:2232-2237.*
Aktas, et al, "Role of residues in the adenosine binding site of NAD of the Ascaris suum malic enzyme," Biochimica et Biophysica Acta, vol. 1784, p. 2059-2064 (2008).
Chen, et al., "Structural Constraints in Protein Engineering: The coenzyme specificity of *Escherichia coli* isocitrate dehydrogenase," Eur. J. Biochem., vol. 250, p. 578-582 (1997).
Hektor, et al., "Identification of a Magnesium-dependent NAD(P)(H)-binding Domain in the Nicotinoprotein Methanol Dehydrogenase from Bacillus methanolicus," The Journal of Biological Chemistry, vol. 277, No. 49, p. 46966-46973 (2002).

(Continued)

*Primary Examiner* — Jason Deveau Rosen
(74) *Attorney, Agent, or Firm* — Pasternak Patent Law

(57) ABSTRACT

Disclosed herein are methods and compositions for targeted modification of one or more endogenous plant malate dehydrogenase genes.

16 Claims, 11 Drawing Sheets

Specification includes a Sequence Listing.

(56) References Cited

U.S. PATENT DOCUMENTS

| | | |
|---|---|---|
| 2011/0201055 A1 | 8/2011 | Doyon et al. |
| 2011/0207221 A1 | 8/2011 | Cost et al. |
| 2011/0239315 A1 | 9/2011 | Bonas et al. |
| 2011/0301073 A1 | 12/2011 | Gregory et al. |

FOREIGN PATENT DOCUMENTS

| | | |
|---|---|---|
| WO | WO 96/06166 | 2/1996 |
| WO | WO 98/53057 | 8/1998 |
| WO | WO 98/37186 | 9/1998 |
| WO | WO 98/53058 | 11/1998 |
| WO | WO 98/53059 | 11/1998 |
| WO | WO 98/53060 | 11/1998 |
| WO | WO 98/54311 | 11/1998 |
| WO | WO 00/27878 | 5/2000 |
| WO | WO 01/53480 | 7/2001 |
| WO | WO 01/60970 | 8/2001 |
| WO | WO 01/88197 | 11/2001 |
| WO | WO 02/016536 | 2/2002 |
| WO | WO 02/057295 | 7/2002 |
| WO | WO 02/077227 | 10/2002 |
| WO | WO 02/099084 | 12/2002 |
| WO | WO 03/016496 | 2/2003 |
| WO | WO 03/080809 | 2/2003 |
| WO | WO 05/014791 | 2/2005 |
| WO | WO 05/084190 | 9/2005 |
| WO | WO 07/014275 | 1/2007 |
| WO | WO 08/056915 | 5/2008 |
| WO | 2008/076290 A2 | 6/2008 |
| WO | 2009/013263 A2 | 1/2009 |
| WO | WO 09/042163 | 4/2009 |

OTHER PUBLICATIONS

GenBank Accession No. AY725476 (Feb. 12, 2005).
Alldread, et al.,"Catalytic-Rate Improvement of a Thermostable Malate Dehydrogenase by a Subtle Alteration in Cofactor Bending," *Biochem. J.* 305:539-548 (1995).
Bibikova, et al., "Stimulation of Homologous Recombination Through Targeted Cleavage by Chimeric Nucleases," *Mol. Cell. Biol.* 21:289-297 (2001).
Bitinate, et al., "FOKI Dimerization is Required for DNA Cleavage," *PNAS USA* 95:10570-10575 (1998).
Boch, et al., "Breaking the Code of DNA Binding Specificity of TAL-Type III Effectors," *Science* 1509-1512 10.1126/science.117881 (2009).
Bombarley, et al., "The SOL Genomics Network (solgenomics.net): Growing Tomatoes Using PERL," *Nucl. Acids Res.* D1149-D1155 (2011).
Centeno, et al., "Malate Plays a Crucial Role in Starch Metabolism, Ripening, and Soluble Solid Content of Tomato Fruit and Affects Postharvest Softening," *Plant Cell* 23:162-184 (2011).
D'Halluin, et al., "Homologous Recombination: A Basis for Targeted Genome Optimization in Crop Species Such as Maize," *Plant Biotechnology Journal* 6(1):93 (2008).
Doyon, et al., "Heritable Targeted Gene Disruption in Zebrafish Using Designed Zinc-Finger Nucleases," *Nat. Biotechnol.* 26:702-708 (2008).
Finkmeier, et al., "The Role of Malate in Plant Homeostasis," *F1000 Biology Reports* I:47; doi:10.3410/B1-47 (2009).
Goodman, et al., "Malate Dehydrogenase: Viability of Cytosolic Nulls and Lethality of Mitochondrial Nulls in Maize," *Proc. Natl. Acad. Sci. USA* 78:1783-1785 (1981).
Geurts, et al., "Knockout Rats Produced Using Designed Zinc Finger Nucleases," *Science* 325:433 (2009).
Guo, et al., "Directed Evolution of an Enhanced and Highly Efficient FOKI Cleavage Domain for Zinc Finger Nucleases," *J. Mol. Biol.* 400(1):96-107 (2010).

Imsande, et al., "Independent Spontaneous Mitochondrial Malate Demydrogenase Null Mutants in Soybean are The Result of Deletions," *J. Heredity* 92:333-338 (2001).
Jinek, et al., "RNA-Programmed Genome Editing in Human Cells," *e.Life* 2:e00471 (2013).
Jinek, et al., "A Programmable Dual-RNA-Guided DNA Endonuclease in Adaptive Bacterial Immunity," *Science* 337:816-821 (2012).
Kim, et al., "Insertion and Deletion Mutants of FOKI Restriction Endonuclease," *J. Biol. Chem.* 269:31978-31982 (1994).
Kim, et al., "Chimeric Restriction Endonuclease," *Proc. Natl. Acad. Sci. USA* 91:883-887 (1994a).
Li, et al., "Functional Domains in FOK I Restriction Endonuclease," *Proc. Natl. Acad. Sci. USA* 89:4275-4279 (1992).
Lloyd, et al., "Targeted Mutagenesis Using Zinc-Finger Nucleases in Arabidopsis," *PNAS USA* 102:2232-223 (2005).
Miller, et al. "Repetitive Zinc-Binding Domains in the Protein Transcription Fator IIIA From Xenapus Oocytes," *EMBO Journal* 4:1609-1614 (1985).
Miller, et al. "A Tale Nuclease Architecture for Efficient Genome Editing," *Nature Biotechnology* 29(2):143-148 (2011).
Moehle, et al., "Targeted Gene Addition Into a Specified Location in The Human Genome Using Designed Zinc Finger Nucleases," *Proc. Natl. Acad. Sci. USA* 104(9):3055-3060 (2007).
Moore, et al., "Design of Polyzinc Finger Peptides With Structured Linkers," *Proc. Natl. Acad. Sci. USA* 98:1432-1436 (2001a).
Moore, et al., "Improved DNA Binding Specificity From Polyzinc Finger Peptides by Using Strings of Two-Finger Units," *Proc. Natl. Acad. Sci. USA* 98:1437-1441 (2001b).
Moscou, et al., "A Simple Cipher Governs DNA Recognition by TAL Effectors," *Science* 326:1501 10.1126/science.1178817 (2009).
Nunes-Nesi, et al., "Operation and Function of the Tricarboxylic Acid Cycle in the Illuminated Leaf," *Physiologia Plantaram.* 129:45-56 (2007).
Nunes-Nesi, et al., "Enhanced Photosynthetic Performance and Growth as a Consequence of Decreasing Mitochondrial Malate Dehydrogenase Activity in Transgenic Tomato Plants," *Plant Physiol.* 137:611-622 (2005).
Nunes-Nesi, "The Enigmatic Contribution of Mitochondrial Function in Photosynthesis," *J. Exp. Bol.* 59:1675-1684 (2005).
Rhodes, "Zinc Fingers," *Scientific American Feb.*:56-65 (1993).
Segal, "Bacteria Herald a New Era of Gene Editing," *eLife* 2:e00563 (2013).
Shukla, et al., "Precise Genome Modification in the Crop Species Zea Mays Using Zinc-Finger Nucleases," *Nature* 495:437-441 (2009).
Smith, et al., "Requirements for Double-Strand Cleavage by Chimeric Restriction Enzymes With Zinc Finger DNA-Recognition Domains," *Nucleic Acids Res.* 28:3361-3369 (2000).
Terada, et al., "Efficient Gene Targeting by Homologous Recombination in Rice," *Nat. Biotechnol.* 20(10):1030 (2002).
Terada, et al., "Gene Targeting by Homologous Recombination as a Biotecelnological Tool for Rice Functional Genomics," *Plant Physiol.* 144(2):846 (2007).
Tomaz, et al., "Mitochondrial Malate Dehydrogenase Lowers Leaf Respiration and Alters Photorespiration and Plant Growth in Arabidopsis," *Plant Physiol* 154(3):1143-1157 (2010).
Urnov, et al., "Highly Efficient Endogenous Human Gene Correction Using Designed Zinc-Finger Nucleases," *Nature* 435:646-651 (2005).
Van der Merwe, et al., "Decreased Mitochondrial Activities of Malate, Dehydrogenase and Fumarase in Tomato Lead to Altered Root Growth and Architecture Via Diverse Mechanisms," *Plant Physiol.* 149:653-669 (2009).
Van der Merwe, et al., "Tricarboxylic Acid Cycle Activity Regulates Tomato Root Growth Via Effects on Secondary Cell Wall Production," *Plant Physiol.* 153:611-621 (2010).
Wah, et al., "Structure of FOKI Has Implications for DNA Cleavage," *Proc. Natl. Acad. Sci. USA* 90:10564-10569 (1998).

\* cited by examiner

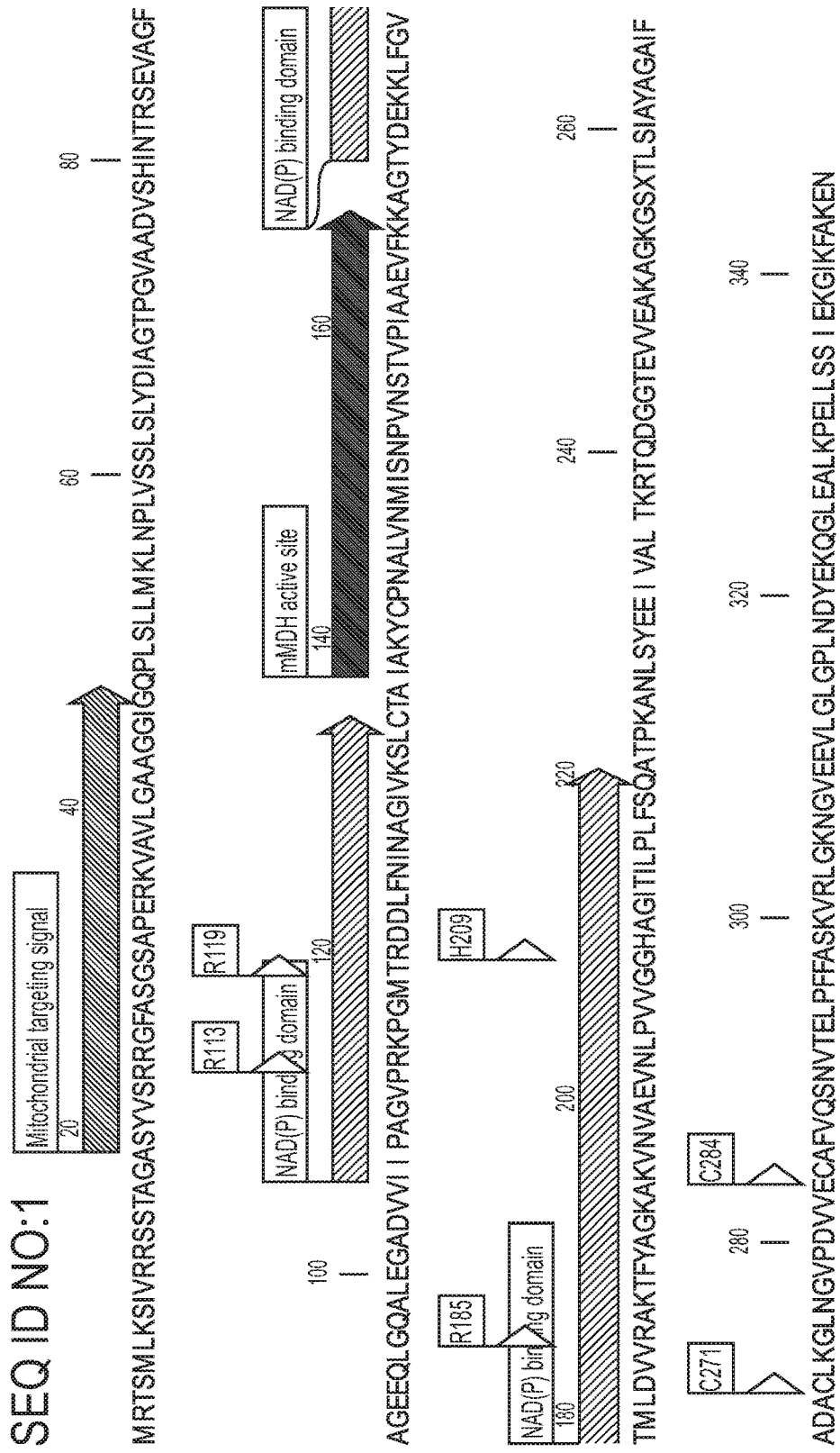

(SEQ ID NO: 2)
ATTTTCTCCGCCGTAGCTTTTACCTTTTCCTCATTTCTTTTGTATATTCCGAAATGAGGACCTCCATG
TTGAAATCCATCGTCCGCCGGAGCTCCACTGCCGGAGCATCCTATGTATCTCGCCGTG**GATTCGCATC
GGGATCCG**CGCCGGAGAGGAAAGTTGCAGTTTTGGGGGCAGCCGGAGGGATTGGACAGCCTTTATCTC
TTCTAATGAAGCTTAACCCTTTAGTATCCAGCCTTTCACTCTACGATATCGCCGGTACTCCCGGTGTT
GCCGCCGATGTTAGTCACATCAACACCAGATCTGAGGTTGTTTTCTACTCTCTCTCTCCCTTACGTTT
TCTACTTGGAATTCTCTGTTTTTGTTCATTTTGTATGAGTATTGGCGAAGATTACTAATGAGGATTTG
TATTAACTAAATTGGAACTAAGACGTATCTGGTAGGTTGATTGATTCTGTTAACATGCTTTTTTGATT
TCCTGAATCTCGAGCTCCGATCCGATTTACGTTAGTCGATTTCACTAGTGAGTTTGAGTTTGTTGCTT
GCTTCATTCCACTATTTAGTCTATTTTTCGAGTGTGTATCACATAAGTACATATAGATTCGTGAATGA
GTTACTAAAGTACAAGGTTTTGTGCTGAAAACTAGGTGTTTGTCAGCAATGAAGAGTTCAACACCAGA
TCATTTTACTCTTTGCATCAGTTGCCTGTTTTAATTTCAAGATGATTTGATTACAATGTTGTTTTAGG
CGTCCACTGTCAAGTAGTTAACGATTTGAAGCCCATCTACCTTTTGTGTCCTAAACCCCTCTAAATAG
TGTTTGTGCCAGTTTATGGTTTTCTTTCCTGCAATTCTGATCTGTAAATATATTTGTGGACTTTGCAG
GTTGCCGGTTTTGCAGGAGAAGAGCAGCTAGGGCAGGCACTGGAAGGAGCTGATGTTGTTATCATTCC
TGCTGGTGTGCCCCGAAAGCCTGGTATGACCCGAGATGATCTGTTCAACATTAATGCGGGTATTGTTA
AATCTCTATGCACGGCCATTGCTAAGTACTGCCCCAATGTGAGTATGCTTGTAATTATCTCTGTAT
ATGGGGGTTATATATAGGAGATTCTAGAAAAAGTTTCTGATTAATTTTCTCATTTGCTGCTTGTTCTG
ATAACTTAAAGGCTCTGGTCAATATGATAAGCAACCCAGTGAATTCCACTGTCCCTATTGCTGCTGAG
GTGTTTAAGAAAGCTGGAACTTATGATGAAAAGAAGCTCTTTGGAGTTACCATGCTT**GATGTGGTTAG
GGCCAAG**ACATTTTATGCTGGAAAAGCTAAAGTAAATGTTGCTGGTGCGCGTCTTCTTGTCTAATTCT
TTATTTGAATTGATTTTGTTTCGCTTTACATGAAACTGTAAATTCATACAATACTATCTGTCTACTTT
ACTTACTTTTTGCTTCGTTTTTCAGAGGTCAATCTCCCAGTAGTTGGTGGTCATGCTGGCATAACTAT
CCTCCCATTATTTTCTCAAGTAATTTTTCTTTTCTTGTCCCTTGTTATAAAGCTTTTTCTTTTTTTAG
TATCTATTATTATCTTCTTTATGTTGTAAGTGTTTGATTGAACATTTTTTAGTATGTATTATCTAAAT
TGTTATTGGTGATTTCCATATTGTGGCATATTGAGTCTTGTTTTTATCACTAAATTTTGGATACAGGC
CACTCCAAAGGCAAATCTATCAGATGAGGAAATTGTTGCACTCACAAAGCGAACCCAAGATGGTGGGA
CAGAAGTTGTAGAGGCCAAGGCTGGAAAGGGTTCAGCCACCCTCTCAATGGCGTACGTTTCCACTTCA
ATGTTTTTCTTGATTTATTTTTTTTTCCTGAAGGATTTTCACTTTGATTGCAAGATTTTGTTTACGAA
TAAGTTATGGTGCTGCCCAATGTCACGGTCAAATATTTAGGAATGTAGAGAAACAAACAAAAAAAGAA
ACTTTTTTGACATATACTGCCCCAAACCACTTCATTTACTGGCCTTTCCTGTTTGCATACTCGGTTCT
AAGCAGTTAGTTTTACTTGTGCAGCTATGCTGGGGCTATTTTTGCCGATGCTTGCTTGAAGGGGTTGA
ATGGAGTTCCCGATGTTGTTGAATGTGCTTTTGTGCAGTCCAAT**GTCACCGAGCTTCCCTTCTTCGCA
TCCAAGGTAA**TAAGCCTTTTCTTTTCCTACAAAGACACTGGACGTCATGTATACTTTTTTCTTTGAAC
TGTCTGATTCATTTGGTCATTGCCCTCTTATCATGTGGGTATGAAAAGGTCAAAACAAATTATATAGT
TCAAGTTTAGGTTTGTTTAAGCATGTCTGAAGCTGTGTCTATTCTGGATGTGTTGAGGGATAGTTTTG
ACATCATGAGTCATCGATTGATCTTGATTAAGCATGTCTCATGTGGAATGGTTGGTAGCTTTTCAACA
GTGCAAGTCGAATGTGTCAAGAACTAAGTTGACATCCTAGGTTATTATTTGTTGTTAGTCACACACGC
ATCTGAACGTAAATAGCTCGTTAACTTTGAATCATGGGCTAAATTTGTACTTCCTCTTATCAACTGAC
TTGTGGGTAATTCACTGTATAAGGTCACTATTTTCATTTTGCTTACTTATACATGTCATTCAATTTGA
TCGCTTTGCAGGTAAGACTTGGGAAAAATGGAGTGGAGGAAGTCCTAGGGTTGGGTCCACTTAACGAC
TACGAGAAGCAAGGACTTGAGGCTCTTAAGCCAGAGCTGCTCTCCTCCATTGAAAAGGGAATCAAGTT
TGCCAAAGAAAACTAAAAAAACAAAATTATGGTCTAGTTTTCTATAGTGACAGTTTTGGATCTTTTTG
GGTCAATTGTTTTTGTATCCTTTGCAAGTTTCTTGCAGCCGGAGGCTTAGATTTAGCTCTTTTTGATAT
TATACCCAACATTTCTACAAAATAATGTATGGCAAACTGGGGCCTATCCCATTTGCCTTAGTGTGGA
GGTGTTATTCTCACATGAATCGTTTTCCAATTATGGTTAGTAGCAGACAATTGATGCAAAATGAAGAA
ATGTTCATGACCAATTACTGCATCGTTTTGCAATTCATTAACCATTTTCTGTCGTTATACTTTTGA

FIG. 2B

```
107830    SEQ ID NO:73 AGCATCCTATGTATCTCGCCGTGGATTCGCATCGGGATCCG

SEQ ID NO:74 AGCATCCTATGTATCTCG-----GATTCGCATCGGGATCCG
          SEQ ID NO:75 AGCATCCTATGTATCTCGC----GATTCGCATCGGGATCCG
          SEQ ID NO:76 AGCATCCTATGTATCTCGCCG---ATTCGCATCGGGATCCG
          SEQ ID NO:77 AGCATCCTATGTATCTCGCCG--GATTCGCATCGGGATCCG
          SEQ ID NO:78 AGCATCCTATGTATCTCGCCG-------CATCGGGATCCG
          SEQ ID NO:79 AGCATCCTATGTATCTCG------ATTCGCATCGGGATCCG

107832    SEQ ID NO:80 CTCTTTGGAGTTACCATGCTTGATGTGGTTAGGGCCAAG

SEQ ID NO:81 CTCTTTGGAGTTACCATG----ATGTGGTTAGGGCCAAG
          SEQ ID NO:82 CTCTTTGGAGTTACCA---------GGTTAGGGCCAAG
          SEQ ID NO:83 CTCTTTGGAGTTACCAT---TGATGTGGTTAGGGCCAAG
          SEQ ID NO:84 CTCTTTGGAGTTACCAT--TTGATGTGGTTAGGGCCAAG
          SEQ ID NO:85 CTCTTTGGAGTTAC------GATGTGGTTAGGGCCAAG
          SEQ ID NO:86 CTCTTTGGAGTTACCA-----GATGTGGTTAGGGCCAAG
          SEQ ID NO:87 CTCTTTGGAGTTACCATTGCTTGATGTGGTTAGGGCCAA

107833 SEQ ID NO:88 TTCAGAGGTCAATCTCCCAGTAGTTGGTGGTCATGCTGGCATAAC

SEQ ID NO:89 TTCAGAGGTCAATCTCCCAGT----GGTGGTCATGCTGGCATAAC
          SEQ ID NO:90 TTCAGAGGTCAATCT--------TGGTGGTCATGCTGGCATAAC
          SEQ ID NO:91 TTCAGAGGTCAATCTCCCAGT--TTGGTGGTCATGCTGGCATAAC
          SEQ ID NO:92 TTCAGAGGTCAATCTCCCA-----TGGTGGTCATGCTGGCATAAC
          SEQ ID NO:93 TTCAGAGGTCAATCTCCCAGTAG-------TCATGCTGGCATAAC
          SEQ ID NO:94 TTCAGAGGTCAATCTCCCAGT-------GGTCATGCTGGCATAAC

SEQ ID NO:95 TTCAGAGGTCAATCTCCCAGTAGTTTGGTGGTCATGCTGGCATAA

107835 SEQ ID NO:96 CACCGAGCTTCCCTTCTTCGCATCCAAGGTAATAAGCC

SEQ ID NO:97 GTCACCGAGCTTCCCTTCTT----TCCAAGGTAATAAGCC
          SEQ ID NO:98 GTCACCGAGCTTCCCTTCTTC-----CAAGGTAATAAGCC
```

FIG. 7

|                |       | 1                                        40 |
|----------------|-------|---------------------------------------------|
| Tomato mMDH    | (1)   | MRTSMLKSIVRRSSTAGASYVSRRGFASGSAPERKVAVLG    |
| Corn mMDH      | (1)   | MRFSLMRSTSQLLRRRSYSSASGQ------PERKVATLG     |
| Soybean mMDH   | (1)   | MKFSMLRSL-HSAATRGASHLSRRGYASEPVPERKVAVLG    |
|                |       | 41                                       80 |
| Tomato mMDH    | (41)  | AAGGIGQPLSLLMKLNPLVSSLSLYDIAGTPGVAADVSHI    |
| Corn mMDH      | (34)  | AAGGIGQPLSLLMKLNPLVSSLSLYDIAGTPGVAADVSHI    |
| Soybean mMDH   | (40)  | AAGGIGQPLSLLMKLNPLVSSLSLYDIAGTPGVAADVSHI    |
|                |       | 81                                      120 |
| Tomato mMDH    | (81)  | NTRSEVAGFAGEEQLGQALEGADVVIIPAGVPRKPGMTRD    |
| Corn mMDH      | (74)  | NSPAIVKGFMGDEQLGEALEGSDVVIIPAGVPRKPGMTRD    |
| Soybean mMDH   | (80)  | NTGSEVVGYQGDEELGKALEGADVVIIPAGVPRKPGMTRD    |
|                |       | 121                                     160 |
| Tomato mMDH    | (121) | DLFNINAGIVKSLQTAIAKYCPNALVNMISNPVNSTVPIA    |
| Corn mMDH      | (114) | DLFNINAGIVKNLSTAIAKYCPNALVNMISNPVNSTVPIA    |
| Soybean mMDH   | (120) | DLFNINAGIVETLQTAIAKYCPHALVNMISNPVNSTVPIA    |
|                |       | 161                                     200 |
| Tomato mMDH    | (161) | AEVFKKAGTYDEKKLFGVTMLDVVRAKTFYAGKAKVNVAE    |
| Corn mMDH      | (154) | AEVFKKAGTYDEKKLFGVTTLDVVRAKTFYAGKANLPVTD    |
| Soybean mMDH   | (160) | AEVFKKAGTYDEKRLFGVTTLDVVRAKTFYAGKANVPVAG    |
|                |       | 201                                     240 |
| Tomato mMDH    | (201) | VNLPVVGGHAGITILPLFSQATPKAN-LSYEEIVALTKRT    |
| Corn mMDH      | (194) | VNVPVVGGHAGITILPLFSQATPATNALSDEDIKALTKRT    |
| Soybean mMDH   | (200) | VNVPVVGGHAGITILPLFSQATPKAN-LDDDVIKALTKRT    |
|                |       | 241                                     280 |
| Tomato mMDH    | (240) | QDGGTEVVEAKAGKGSXTLSIAYAGAIFADACLKGLNGVP    |
| Corn mMDH      | (234) | QDGGTEVVEAKAGKGSATLSMAYAGAVFADACLKGLNGVP    |
| Soybean mMDH   | (239) | QDGGTEVVEAKAGKGSATLSMAYAGALFADACLKGLNGVP    |
|                |       | 281                                     320 |
| Tomato mMDH    | (280) | DVVEQAFVQSNVTELPFFASKVRLGKNGVEEVLGLGPLND    |
| Corn mMDH      | (274) | DIVECSFVQSTVTELPFFASKVRLGKNGVEEVLGLGELSD    |
| Soybean mMDH   | (279) | DVVECSFVQSTVTELPYFASKVRLGKNGVEEVLGLGPLSD    |
|                |       | 321                                     360 |
| Tomato mMDH    | (320) | MEKQGLEALKPELLSSIEKGIKFAKEN-------------    |
| Corn mMDH      | (314) | FEKEGLEKLKSELKSSIEKGIKFANDIRPFCRLQQLKPL     |
| Soybean mMDH   | (319) | FEQQGLESLKPELKSSIEKGIKFANQLNMLSHTCLVGCCY    |
|                |       | 361                                     400 |
| Tomato mMDH    | (347) | ----------------------------------------    |
| Corn mMDH      | (354) | VAIETFSCGIFFHSTLFCPFLGSGRYYNKKPDGQSLQEGF    |
| Soybean mMDH   | (359) | SFKNQIKFCNLRTIVVLLPA--------------------    |
|                |       | 401                          426             |
| Tomato mMDH    | (347) | --------------------------                   |
| Corn mMDH      | (394) | IPAGRHITYVKFCTEPVVYELSAAFY                   |
| Soybean mMDH   | (379) | --------------------------                   |

FIG. 10

WT (SEQ ID NO:127):           LFGVTML   DVVRAK
107832 3-8 (SEQ ID NO:128):   LFGVT  -I  DVVRAK
107832 76-5 (SEQ ID NO:129):  LFGVD  ---  VVRAK
107832 9-8 (SEQ ID NO:130):   LFGVT  -I  VVRAK
107832 9-7 (SEQ ID NO:131):   LFGVT  -I  DVVRAK

SEQUENCE LISTING

```
<160> NUMBER OF SEQ ID NOS: 138

<210> SEQ ID NO 1
<211> LENGTH: 346
<212> TYPE: PRT
<213> ORGANISM: Solanum lycopersicum
<220> FEATURE:
<221> NAME/KEY: MOD_RES
<222> LOCATION: (256)..(256)
<223> OTHER INFORMATION: Any amino acid

<400> SEQUENCE: 1

Met Arg Thr Ser Met Leu Lys Ser Ile Val Arg Arg Ser Ser Thr Ala
```

```
              1               5                  10                 15
          Gly Ala Ser Tyr Val Ser Arg Arg Gly Phe Ala Ser Gly Ser Ala Pro
                          20                  25                  30

Glu Arg Lys Val Ala Val Leu Gly Ala Ala Gly Gly Ile Gly Gln Pro
                          35                  40                  45

Leu Ser Leu Leu Met Lys Leu Asn Pro Leu Val Ser Ser Leu Ser Leu
           50                  55                  60

Tyr Asp Ile Ala Gly Thr Pro Gly Val Ala Ala Asp Val Ser His Ile
           65                  70                  75                  80

Asn Thr Arg Ser Glu Val Ala Gly Phe Ala Gly Glu Glu Gln Leu Gly
                          85                  90                  95

Gln Ala Leu Glu Gly Ala Asp Val Val Ile Ile Pro Ala Gly Val Pro
                          100                 105                 110

Arg Lys Pro Gly Met Thr Arg Asp Asp Leu Phe Asn Ile Asn Ala Gly
                          115                 120                 125

Ile Val Lys Ser Leu Cys Thr Ala Ile Ala Lys Tyr Cys Pro Asn Ala
                          130                 135                 140

Leu Val Asn Met Ile Ser Asn Pro Val Asn Ser Thr Val Pro Ile Ala
           145                 150                 155                 160

Ala Glu Val Phe Lys Lys Ala Gly Thr Tyr Asp Glu Lys Lys Leu Phe
                          165                 170                 175

Gly Val Thr Met Leu Asp Val Val Arg Ala Lys Thr Phe Tyr Ala Gly
                          180                 185                 190

Lys Ala Lys Val Asn Val Ala Glu Val Asn Leu Pro Val Val Gly Gly
                          195                 200                 205

His Ala Gly Ile Thr Ile Leu Pro Leu Phe Ser Gln Ala Thr Pro Lys
                          210                 215                 220

Ala Asn Leu Ser Tyr Glu Glu Ile Val Ala Leu Thr Lys Arg Thr Gln
           225                 230                 235                 240

Asp Gly Gly Thr Glu Val Val Glu Ala Lys Ala Gly Lys Gly Ser Xaa
                          245                 250                 255

Thr Leu Ser Ile Ala Tyr Ala Gly Ala Ile Phe Ala Asp Ala Cys Leu
                          260                 265                 270

Lys Gly Leu Asn Gly Val Pro Asp Val Val Glu Cys Ala Phe Val Gln
                          275                 280                 285

Ser Asn Val Thr Glu Leu Pro Phe Phe Ala Ser Lys Val Arg Leu Gly
                          290                 295                 300

Lys Asn Gly Val Glu Glu Val Leu Gly Leu Gly Pro Leu Asn Asp Tyr
           305                 310                 315                 320

Glu Lys Gln Gly Leu Glu Ala Leu Lys Pro Glu Leu Leu Ser Ser Ile
                          325                 330                 335

Glu Lys Gly Ile Lys Phe Ala Lys Glu Asn
                          340                 345

<210> SEQ ID NO 2
<211> LENGTH: 3126
<212> TYPE: DNA
<213> ORGANISM: Solanum lycopersicum

<400> SEQUENCE: 2
attttctccg ccgtagcttt tacctttctcc tcatttcttt tgtatattcc gaaatgagga    60
cctccatgtt gaaatccatc gtccgccgga gctccactgc cggagcatcc tatgtatctc   120
gccgtggatt cgcatcggga tccgcgccgg agaggaaagt tgcagttttg ggggcagccg   180
```

```
gagggattgg acagcctttta tctcttctaa tgaagcttaa ccctttagta tccagccttt    240
cactctacga tatcgccggt actcccggtg ttgccgccga tgttagtcac atcaacacca    300
gatctgaggt tgttttctac tctctctctc ccttacgttt tctacttgga attctctgtt    360
tttgttcatt ttgtatgagt attggcgaag attactaatg aggatttgta ttaactaaat    420
tggaactaag acgtatctgg taggttgatt gattctgtta acatgctttt ttgatttcct    480
gaatctcgag ctccgatccg atttacgtta gtcgatttca ctagtgagtt tgagtttgtt    540
gcttgcttca ttccactatt tagtctattt ttcgagtgtg tatcacataa gtacatatag    600
attcgtgaat gagttactaa agtacaaggt tttgtgctga aaactaggtg tttgtcagca    660
atgaagagtt caacaccaga tcattttact ctttgcatca gttgcctgtt ttaatttcaa    720
gatgatttga ttacaatgtt gttttaggcg tccactgtca agtagttaac gatttgaagc    780
ccatctacct tttgtgtcct aaaccctct aaatagtgtt tgtgccagtt tatggttttc    840
tttcctgcaa ttctgatctg taaatatatt tgtggacttt gcaggttgcc ggttttgcag    900
gagaagagca gctagggcag gcactggaag gagctgatgt tgttatcatt cctgctggtg    960
tgccccgaaa gcctggtatg acccgagatg atctgttcaa cattaatgcg ggtattgtta   1020
aatctctatg cacggccatt gctaagtact gccccaatgt gagtatgctt gtgtaattat   1080
ctctgtatat gggggttata tataggagat tctagaaaaa gtttctgatt aattttctca   1140
tttgctgctt gttctgataa cttaaaggct ctggtcaata tgataagcaa cccagtgaat   1200
tccactgtcc ctattgctgc tgaggtgttt aagaaagctg gaacttatga tgaaaagaag   1260
ctctttggag ttaccatgct tgatgtggtt agggccaaga cattttatgc tggaaaagct   1320
aaagtaaatg ttgctggtgc gcgtcttctt gtctaattct ttatttgaat tgattttgtt   1380
tcgctttaca tgaaactgta aattcataca atactatctg tctactttac ttactttttg   1440
cttcgttttt cagaggtcaa tctcccagta gttggtggtc atgctggcat aactatcctc   1500
ccattatttt ctcaagtaat ttttcttttc ttgtcccttg ttataaagct ttttcttttt   1560
ttagtatcta ttattatctt ctttatgttg taagtgtttg attgaacatt ttttagtatg   1620
tattatctaa attgttattg gtgatttcca tattgtggca tattgagtct tgttttttatc   1680 actaaatttt ggatacaggc cactccaaag gcaaatctat cagatgagga aattgttgca   1740
ctcacaaagc gaacccaaga tggtgggaca gaagttgtag aggccaaggc tggaaagggt   1800
tcagccaccc tctcaatggc gtacgtttcc acttcaatgt ttttcttgat ttatttttttt  1860 ttcctgaagg atttcacttt tgattgcaag attttgtttta cgaataagtt atggtgctgc   1920
ccaatgtcac ggtcaaatat ttaggaatgt agagaaacaa acaaaaaaag aaactttttt   1980
gacatatact gccccaaacc acttcattta ctggcctttc ctgtttgcat actcggttct   2040
aagcagttag ttttacttgt gcagctatgc tggggctatt tttgccgatg cttgcttgaa   2100
ggggttgaat ggagttcccg atgttgttga atgtgctttt gtgcagtcca atgtcaccga   2160
gcttcccttc ttcgcatcca aggtaataag ccttttcttt tcctacaaag acactggacg   2220
tcatgtatac ttttttcttt gaactgtctg attcatttgg tcattgccct cttatcatgt   2280
gggtatgaaa aggtcaaaac aaattatata gttcaagttt aggtttgttt aagcatgtct   2340
gaagctgtgt ctattctgga tgtgttgagg atagttttg acatcatgag tcatcgattg   2400
atcttgatta agcatgtctc atgtggaatg gttggtagct tttcaacagt gcaagtcgaa   2460
tgtgtcaaga actaagttga catcctaggt tattatttgt tgttagtcac acacgcatct   2520
gaacgtaaat agctcgttaa ctttgaatca tgggctaaat ttgtacttcc tcttatcaac   2580
```

```
tgacttgtgg gtaattcact gtataaggtc actattttca ttttgcttac ttatacatgt    2640
cattcaattt gatcgctttg caggtaagac ttgggaaaaa tggagtggag gaagtcctag    2700
ggttgggtcc acttaacgac tacgagaagc aaggacttga ggctcttaag ccagagctgc    2760
tctcctccat tgaaaaggga atcaagtttg ccaaagaaaa ctaaaaaaac aaaattatgg    2820
tctagttttc tatagtgaca gttttggatc tttttgggtc aattgttttt gtatcctttg    2880
caagtttctt gcagccggag gcttagattt agctcttttg atattatacc caacatttct    2940
acaaaataat gtatggcaaa ctgggggcct atcccatttg ccttagtgtg gaggtgttat    3000
tctcacatga atcgttttcc aattatggtt agtagcagac aattgatgca aaatgaagaa    3060
atgttcatga ccaattactg catcgttttg caattcatta accatttttct gtcgttatac    3120 ttttga                                                                3126
```

<210> SEQ ID NO 3
<211> LENGTH: 41
<212> TYPE: DNA
<213> ORGANISM: Solanum lycopersicum

<400> SEQUENCE: 3
agcatcctat gtatctcgcc gtggattcgc atcgggatcc g                         41

<210> SEQ ID NO 4
<211> LENGTH: 41
<212> TYPE: DNA
<213> ORGANISM: Solanum lycopersicum

<400> SEQUENCE: 4
cggatcccga tgcgaatcca cggcgagata cataggatgc t                         41

<210> SEQ ID NO 5
<211> LENGTH: 39
<212> TYPE: DNA
<213> ORGANISM: Solanum lycopersicum

<400> SEQUENCE: 5
ctctttggag ttaccatgct tgatgtggtt agggccaag                            39

<210> SEQ ID NO 6
<211> LENGTH: 39
<212> TYPE: DNA
<213> ORGANISM: Solanum lycopersicum

<400> SEQUENCE: 6
cttggcccta accacatcaa gcatggtaac tccaaagag                            39

<210> SEQ ID NO 7
<211> LENGTH: 45
<212> TYPE: DNA
<213> ORGANISM: Solanum lycopersicum

<400> SEQUENCE: 7
ttcagaggtc aatctcccag tagttggtgg tcatgctggc ataac                     45

<210> SEQ ID NO 8
<211> LENGTH: 45
<212> TYPE: DNA
<213> ORGANISM: Solanum lycopersicum

<400> SEQUENCE: 8
gttatgccag catgaccacc aactactggg agattgacct ctgaa    45

```
<210> SEQ ID NO 9
<211> LENGTH: 40
<212> TYPE: DNA
<213> ORGANISM: Solanum lycopersicum

<400> SEQUENCE: 9
```
gtcaccgagc ttcccttctt cgcatccaag gtaataagcc    40

```
<210> SEQ ID NO 10
<211> LENGTH: 40
<212> TYPE: DNA
<213> ORGANISM: Solanum lycopersicum

<400> SEQUENCE: 10
```
ggcttattac cttggatgcg aagaagggaa gctcggtgac    40

```
<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

Arg Ser Asp Asp Leu Ser Glu
1               5

```
<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12
```

Thr Asn Ser Asn Arg Lys Arg
1               5

```
<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13
```

Arg Ser Asp His Leu Ser Thr
1               5

```
<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14
```

Thr Asn Ser Asn Arg Ile Thr
1               5

```
<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Arg Glu Asp Leu Ile Thr
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Ser Ser Asn Leu Ser Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Ser Ser Asp Leu Ser Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Ser Gly Asn Leu Thr Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ser Asp Tyr Leu Ser Lys
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20
```

Thr Ser Ser Val Arg Thr Thr
1               5

<210> SEQ ID NO 21

<400> SEQUENCE: 21

000

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Arg Ser His Leu Ser Asp
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Ser Asp Thr Leu Ser Val
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Asn Ser Thr Arg Ile Lys
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ser Asp His Leu Ser Glu
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Ser Gly Ser Leu Thr Arg

```
<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Ser Asp Ala Leu Ser Arg
1               5

<210> SEQ ID NO 28

<400> SEQUENCE: 28

000

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ser Asp Asn Leu Ala Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Arg Gly Asn Arg Asn Thr
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Ser Ser Asp Arg Lys Lys
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Arg Ser Asn Leu Ser Arg
1               5
```

```
<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Arg His His Leu Thr Arg
1               5

<210> SEQ ID NO 34

<400> SEQUENCE: 34

000

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Arg Gln Asn Leu Ile Met
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ser Asp Ala Leu Ser Glu
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ser Ser Thr Arg Lys Thr
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Arg Ser Ala Leu Ser Arg
1               5

<210> SEQ ID NO 39
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Ser Asp Ala Leu Ala Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Ser Gly Asn Leu Ala Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asn Arg Tyr Asp Leu His Lys
1               5

<210> SEQ ID NO 42

<400> SEQUENCE: 42

000

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Arg Phe Ala Arg Asp Ala
1               5

<210> SEQ ID NO 44

<400> SEQUENCE: 44

000

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45
```

Arg Ser Asp His Leu Thr Gln
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Arg Ser Asp Leu Ser Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Ala Gly Asn Leu Lys Lys
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ser Gly Ser Leu Thr Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Ser Asp Asn Leu Arg Glu
1               5

<210> SEQ ID NO 50

<400> SEQUENCE: 50

000

<210> SEQ ID NO 51

<400> SEQUENCE: 51

000

<210> SEQ ID NO 52
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 52

Leu Lys Gln His Leu Thr Arg
1               5

<210> SEQ ID NO 53

<400> SEQUENCE: 53

000

<210> SEQ ID NO 54

<400> SEQUENCE: 54

000

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Ser Asp His Leu Ser Gln
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Asn Ala His Arg Ile Thr
1               5

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
accacaactc ctaatttatt ttctccg                                     27

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
aaggctggat actaaagggt                                             20

<210> SEQ ID NO 59
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
taagtactgc cccaatgtga g                                              21

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ttgggttcgc tttgtgagt                                                 19

<210> SEQ ID NO 61

<400> SEQUENCE: 61

000

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Ser Glu Val Ala Gly Phe Ala Gly Glu Glu Gln Leu Gly Gln Ala
1               5                   10                  15

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
atactgcccc aaaccact                                                  18

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
actatccctc aacacatcca gaa                                            23

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 65
cgtagctttt aacctttcct c                                          21

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ataaaggctg tccaatccc                                             19

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
caatatgata agcaacccag                                            20

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ttagacaaga agacgcgca                                             19

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gcgtcttctt gtctaattc                                             19

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cttgagaaaa taatgggagg                                            20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
```

```
cggttctaag cagttagttt                                              20

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tgacgtccag tgtctttgt                                               19

<210> SEQ ID NO 73
<211> LENGTH: 41
<212> TYPE: DNA
<213> ORGANISM: Solanum lycopersicum

<400> SEQUENCE: 73
agcatcctat gtatctcgcc gtggattcgc atcgggatcc g                      41

<210> SEQ ID NO 74
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
agcatcctat gtatctcgga ttcgcatcgg gatccg                            36

<210> SEQ ID NO 75
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
agcatcctat gtatctcgcg attcgcatcg ggatccg                           37

<210> SEQ ID NO 76
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
agcatcctat gtatctcgcc gattcgcatc gggatccg                          38

<210> SEQ ID NO 77
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
agcatcctat gtatctcgcc ggattcgcat cgggatccg                         39
```

<210> SEQ ID NO 78
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 78
agcatcctat gtatctcgcc gcatcgggat ccg            33

<210> SEQ ID NO 79
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 79
agcatcctat gtatctcgat tcgcatcggg atccg          35

<210> SEQ ID NO 80
<211> LENGTH: 39
<212> TYPE: DNA
<213> ORGANISM: Solanum lycopersicum

<400> SEQUENCE: 80
ctctttggag ttaccatgct tgatgtggtt agggccaag      39

<210> SEQ ID NO 81
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 81
ctctttggag ttaccatgat gtggttaggg ccaag          35

<210> SEQ ID NO 82
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 82
ctctttggag ttaccaggtt agggccaag                 29

<210> SEQ ID NO 83
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83
ctctttggag ttaccattga tgtggttagg gccaag         36

<210> SEQ ID NO 84
<211> LENGTH: 37
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 84
ctctttggag ttaccatttg atgtggttag ggccaag                              37

<210> SEQ ID NO 85
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ctctttggag ttacgatgtg gttagggcca ag                                   32

<210> SEQ ID NO 86
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ctctttggag ttaccagatg tggttagggc caag                                 34

<210> SEQ ID NO 87
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ctctttggag ttaccattgc ttgatgtggt tagggccaa                            39

<210> SEQ ID NO 88
<211> LENGTH: 45
<212> TYPE: DNA
<213> ORGANISM: Solanum lycopersicum

<400> SEQUENCE: 88
ttcagaggtc aatctcccag tagttggtgg tcatgctggc ataac                     45

<210> SEQ ID NO 89
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ttcagaggtc aatctcccag tggtggtcat gctggcataa c                         41

<210> SEQ ID NO 90
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 90
ttcagaggtc aatcttggtg gtcatgctgg cataac                36

<210> SEQ ID NO 91
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ttcagaggtc aatctcccag tttggtggtc atgctggcat aac                43

<210> SEQ ID NO 92
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ttcagaggtc aatctcccat ggtggtcatg ctggcataac                40

<210> SEQ ID NO 93
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ttcagaggtc aatctcccag tagtcatgct ggcataac                38

<210> SEQ ID NO 94
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ttcagaggtc aatctcccag tggtcatgct ggcataac                38

<210> SEQ ID NO 95
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ttcagaggtc aatctcccag tagtttggtg gtcatgctgg cataa                45

<210> SEQ ID NO 96
<211> LENGTH: 38
<212> TYPE: DNA
<213> ORGANISM: Solanum lycopersicum

<400> SEQUENCE: 96
caccgagctt cccttcttcg catccaaggt aataagcc                38

<210> SEQ ID NO 97
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gtcaccgagc ttcccttctt tccaaggtaa taagcc                                36

<210> SEQ ID NO 98
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gtcaccgagc ttcccttctt ccaaggtaat aagcc                                 35

<210> SEQ ID NO 99
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
agcatcctat gtatctggat tcgcatcggg atccg                                 35

<210> SEQ ID NO 100
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
agcatcctat gtatctcgcc ggattcgcat cgggatccg                             39

<210> SEQ ID NO 101
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
agcatcctat gtatctgtgg attcgcatcg ggatccg                               37

<210> SEQ ID NO 102
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
agcatcctat gtatggattc gcatcgggat ccg                                   33

```
<210> SEQ ID NO 103
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ctctttggag ttaccatgct cttgatgtgg ttagggccaa g                    41

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
ctctttggag ttgatgtggt tagggccaag                                 30

<210> SEQ ID NO 105
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ctctttggag ttaccatgtg gttagggcca ag                              32

<210> SEQ ID NO 106
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
ctctttggag ttaccattga tgtggttagg gccaag                          36

<210> SEQ ID NO 107
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ctctttggag ttaccattga tgtggttagg gccaag                          36

<210> SEQ ID NO 108
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
ctctttggag ttaccattga tgtggttagg gccaag                          36

<210> SEQ ID NO 109
```

```
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ctctttggag ttaccatgct gtggttaggg ccaag                         35

<210> SEQ ID NO 110
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
ctctttggag ttaccattga tgtggttagg gccaag                        36

<210> SEQ ID NO 111
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ctctttggag ttaccatgat gtggttaggg ccaag                         35

<210> SEQ ID NO 112
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ctctttggag ttaccatgat gtggttaggg ccaag                         35

<210> SEQ ID NO 113
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ctctttggag ttaccttgat gtggttaggg ccaag                         35

<210> SEQ ID NO 114
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ctctttggag ttaccatgat gtggttaggg ccaag                         35

<210> SEQ ID NO 115
<211> LENGTH: 38
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ctctttggag ttaccatctt gatgtggtta gggccaag                                38

<210> SEQ ID NO 116
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ctctttggag ttaccatgat gtggttaggg ccaag                                   35

<210> SEQ ID NO 117
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ctctttggag ttaccatgcg atgtggttag ggccaag                                 37

<210> SEQ ID NO 118
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ctctttggag ttaccatgct gtggttaggg ccaag                                   35

<210> SEQ ID NO 119
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ctctttggag ttaccttgat gtggttaggg ccaag                                   35

<210> SEQ ID NO 120
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
ctctttggag ttaccattga tgtggttagg gccaag                                  36

<210> SEQ ID NO 121
<211> LENGTH: 36
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 121
ctctttggag ttaccattga tgtggttagg gccaag                                36

<210> SEQ ID NO 122
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
caccgagctt ccctt                                                       15

<210> SEQ ID NO 123
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
caccgagctt cccttcccaa ggtaataagc c                                     31

<210> SEQ ID NO 124
<211> LENGTH: 1041
<212> TYPE: DNA
<213> ORGANISM: Solanum lycopersicum
<220> FEATURE:
<221> NAME/KEY: modified_base
<222> LOCATION: (766)..(766)
<223> OTHER INFORMATION: a, c, t, g, unknown or other

<400> SEQUENCE: 124
atgtcaagga cctccatgtt gaaatccatc gtccgccgga gctccactgc cggagcatcc      60
tatgtatctc gccgtggatt cgcatcggga tccgcgccgg agaggaaagt tgcagttttg     120
ggggcagccg gagggattgg acagccttta tctcttctaa tgaagcttaa ccctttagta     180
tccagccttt cactctacga tatcgccggt actcccggtg ttgccgccga tgttagtcac     240
atcaacacca gatctgaggt tgccggtttt gcaggagaag agcagctagg caggcactg      300 gaaggagctg atgttgttat cattcctgct ggtgtgcccc gaaagcctgg tacccgagat     360
gatctgttca acattaatgc gggtattgtt aaatctctat gcacggccat tgctaagtac     420
tgccccaatg ctctggtcaa tatgataagc aacccagtga actccactgt ccctattgct     480
gctgaggtgt ttaagaaagc tggaacttat gatgaaaaga agctctttgg agttaccatg     540
cttgatgtgg ttagggccaa gacattttat gctggaaaag ctaaagtaaa tgttgctgag     600
gtcaatctcc cagtagttgg tggtcatgct ggcataacta tcctcccatt attttctcaa     660
gccactccaa aggcaaatct atcatatgag gaaattgttg cactcacaaa gcgaacccaa     720
gatggtggga cagaagttgt agaagccaaa gctgaaaggg ttcanccac cctctcaata     780 gcctatgctg ggctattttt tgccgatgct tgcttgaagg ggttgaatgg agttcccgat     840
gttgttgaat gtgcttttgt gcagtccaat gtcaccgagc ttcccttctt cgcatccaag     900
gtaagacttg ggaaaaatgg agtggaggaa gtcctagggt tgggtccact taacgactac     960

```
gagaagcaag gacttgaggc tcttaagcca gagctgctct cctccattga aaagggaatc    1020
aagtttgcca agaaaacta a                                              1041
```

<210> SEQ ID NO 125
<211> LENGTH: 378
<212> TYPE: PRT
<213> ORGANISM: Glycine max

<400> SEQUENCE: 125

```
Met Lys Pro Ser Met Leu Arg Ser Leu His Ser Ala Ala Thr Arg Gly
1               5                   10                  15

Ala Ser His Leu Ser Arg Arg Gly Tyr Ala Ser Glu Pro Val Pro Glu
            20                  25                  30

Arg Lys Val Ala Val Leu Gly Ala Ala Gly Gly Ile Gly Gln Pro Leu
        35                  40                  45

Ser Leu Leu Met Lys Leu Asn Pro Leu Val Ser Ser Leu Ser Leu Tyr
    50                  55                  60

Asp Ile Ala Gly Thr Pro Gly Val Ala Ala Asp Val Ser His Ile Asn
65                  70                  75                  80

Thr Gly Ser Glu Val Val Gly Tyr Gln Gly Asp Glu Glu Leu Gly Lys
                85                  90                  95

Ala Leu Glu Gly Ala Asp Val Val Ile Ile Pro Ala Gly Val Pro Arg
            100                 105                 110

Lys Pro Gly Met Thr Arg Asp Asp Leu Phe Asn Ile Asn Ala Gly Ile
        115                 120                 125

Val Glu Thr Leu Cys Thr Ala Ile Ala Lys Tyr Cys Pro His Ala Leu
    130                 135                 140

Val Asn Met Ile Ser Asn Pro Val Asn Ser Thr Val Pro Ile Ala Ala
145                 150                 155                 160

Glu Val Phe Lys Lys Ala Gly Thr Tyr Asp Glu Lys Arg Leu Phe Gly
                165                 170                 175

Val Thr Thr Leu Asp Val Val Arg Ala Lys Thr Phe Tyr Ala Gly Lys
            180                 185                 190

Ala Asn Val Pro Val Ala Gly Val Asn Val Pro Val Val Gly Gly His
        195                 200                 205

Ala Gly Ile Thr Ile Leu Pro Leu Phe Ser Gln Ala Thr Pro Lys Ala
    210                 215                 220

Asn Leu Asp Asp Asp Val Ile Lys Ala Leu Thr Lys Arg Thr Gln Asp
225                 230                 235                 240

Gly Gly Thr Glu Val Val Glu Ala Lys Ala Gly Lys Gly Ser Ala Thr
                245                 250                 255

Leu Ser Met Ala Tyr Ala Gly Ala Leu Phe Ala Asp Ala Cys Leu Lys
            260                 265                 270

Gly Leu Asn Gly Val Pro Asp Val Val Glu Cys Ser Phe Val Gln Ser
        275                 280                 285

Thr Val Thr Glu Leu Pro Tyr Phe Ala Ser Lys Val Arg Leu Gly Lys
    290                 295                 300

Asn Gly Val Glu Glu Val Leu Gly Leu Gly Pro Leu Ser Asp Phe Glu
305                 310                 315                 320

Gln Gln Gly Leu Glu Ser Leu Lys Pro Glu Leu Lys Ser Ser Ile Glu
                325                 330                 335

Lys Gly Ile Lys Phe Ala Asn Gln Leu Asn Met Leu Ser His Thr Cys
            340                 345                 350

Leu Val Gly Cys Cys Tyr Ser Phe Lys Asn Gln Ile Lys Phe Cys Asn
```

```
                    355                 360                 365
Leu Arg Thr Ile Val Leu Leu Pro Ala
        370                 375

<210> SEQ ID NO 126
<211> LENGTH: 419
<212> TYPE: PRT
<213> ORGANISM: Zea mays

<400> SEQUENCE: 126

Met Arg Pro Ser Leu Met Arg Ser Thr Ser Gln Leu Leu Arg Arg Arg
1               5                   10                  15

Ser Tyr Ser Ser Ala Ser Gly Gln Pro Glu Arg Lys Val Ala Ile Leu
            20                  25                  30

Gly Ala Ala Gly Gly Ile Gly Gln Pro Leu Ser Leu Leu Met Lys Leu
        35                  40                  45

Asn Pro Leu Val Ser Ser Leu Ser Leu Tyr Asp Ile Ala Gly Thr Pro
    50                  55                  60

Gly Val Ala Ala Asp Val Ser His Ile Asn Ser Pro Ala Leu Val Lys
65                  70                  75                  80

Gly Phe Met Gly Asp Glu Gln Leu Gly Glu Ala Leu Glu Gly Ser Asp
                85                  90                  95

Val Val Ile Ile Pro Ala Gly Val Pro Arg Lys Pro Gly Met Thr Arg
            100                 105                 110

Asp Asp Leu Phe Asn Ile Asn Ala Gly Ile Val Lys Asn Leu Ser Thr
        115                 120                 125

Ala Ile Ala Lys Tyr Cys Pro Asn Ala Leu Val Asn Met Ile Ser Asn
    130                 135                 140

Pro Val Asn Ser Thr Val Pro Ile Ala Ala Glu Val Phe Lys Lys Ala
145                 150                 155                 160

Gly Thr Tyr Asp Glu Lys Lys Leu Phe Gly Val Thr Thr Leu Asp Val
                165                 170                 175

Val Arg Ala Lys Thr Phe Tyr Ala Gly Lys Ala Asn Leu Pro Val Thr
            180                 185                 190

Asp Val Asn Val Pro Val Val Gly Gly His Ala Gly Ile Thr Ile Leu
        195                 200                 205

Pro Leu Phe Ser Gln Ala Thr Pro Ala Thr Asn Ala Leu Ser Asp Glu
    210                 215                 220

Asp Ile Lys Ala Leu Thr Lys Arg Thr Gln Asp Gly Gly Thr Glu Val
225                 230                 235                 240

Val Glu Ala Lys Ala Gly Lys Gly Ser Ala Thr Leu Ser Met Ala Tyr
                245                 250                 255

Ala Gly Ala Val Phe Ala Asp Ala Cys Leu Lys Gly Leu Asn Gly Val
            260                 265                 270

Pro Asp Ile Val Glu Cys Ser Phe Val Gln Ser Thr Val Thr Glu Leu
        275                 280                 285

Pro Phe Phe Ala Ser Lys Val Arg Leu Gly Lys Asn Gly Val Glu Glu
    290                 295                 300

Val Leu Gly Leu Gly Glu Leu Ser Asp Phe Glu Lys Glu Gly Leu Glu
305                 310                 315                 320

Lys Leu Lys Ser Glu Leu Lys Ser Ser Ile Glu Lys Gly Ile Lys Phe
                325                 330                 335

Ala Asn Asp Asn Ile Arg Pro Phe Cys Arg Leu Gln Gln Leu Lys Pro
            340                 345                 350
```

Leu Val Ala Ile Glu Thr Phe Ser Cys Gly Ile Phe His Ser Thr
            355                 360                 365

Leu Phe Cys Pro Phe Leu Gly Ser Gly Arg Tyr Tyr Asn Lys Pro
    370                 375                 380

Asp Gly Gln Ser Leu Gln Glu Gly Phe Ile Pro Ala Gly Arg His Ile
385                 390                 395                 400

Thr Tyr Val Lys Phe Cys Thr Glu Pro Val Val Tyr Glu Leu Ser Ala
                405                 410                 415

Ala Phe Tyr

<210> SEQ ID NO 127
<211> LENGTH: 13
<212> TYPE: PRT
<213> ORGANISM: Solanum lycopersicum

<400> SEQUENCE: 127

Leu Phe Gly Val Thr Met Leu Asp Val Val Arg Ala Lys
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Leu Phe Gly Val Thr Ile Asp Val Val Arg Ala Lys
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Leu Phe Gly Val Asp Val Val Arg Ala Lys
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Leu Phe Gly Val Thr Ile Val Val Arg Ala Lys
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Leu Phe Gly Val Thr Ile Asp Val Val Arg Ala Lys

<210> SEQ ID NO 132
<211> LENGTH: 1021
<212> TYPE: DNA
<213> ORGANISM: Zea mays

<400> SEQUENCE: 132

| | | |
|---|---|---|
| atgaaggccg tcgctgatga gatccacctc ccagctcctc cgccgccgga gctactcctc | 60 |
| cgcatccggg cagcccgagc ggaaggtggc catcctcggg gcggcggggg gcatcgggca | 120 |
| gccgctgtcg ctgctcatga agcttaaccc actcgtctcc tccctctcgc tctacgatat | 180 |
| cgccggcacc ccaggtgtcg cggccgacgt ctcccacatc aactcccccg ccctggtgaa | 240 |
| gggtttcatg ggtgatgagc agcttgggga agcgctagag ggctcggacg tggtgatcat | 300 |
| accggccggc gtcccgagga agcccggcat gaccagggac gacctattca atatcaacgc | 360 |
| tggcatcgtt aagaacctca gcaccgccat cgccaagtac tgccccaatg cccttgtcaa | 420 |
| catgatcagc aaccctgtga actcaactgt accgattgct gctgaggttt tcaagaaggc | 480 |
| tgggacatat gatgagaaga agttgtttgg cgtgaccact gatgttgttc gtgctaagac | 540 |
| tttctatgct gggaaggcta atttaccagt taccgatgtg aatgtccctg ttgttggtgg | 600 |
| tcatgcgggt atcactatcc tgccgttgtt ctcacaggcc acccctgcaa ccaacgcatt | 660 |
| gtctgatgaa gacatcaagg ctctcaccaa gaggacacag gatggtggaa ctgaagttgt | 720 |
| cgaggcaaag gctgggaagg gctctgcaac cttgtccatg gcgtatgctg gtgctgtttt | 780 |
| tgcagatgca tgcttgaagg gtctcaatgg agttccggat attgttgagt gctcttttgt | 840 |
| tcaatcaact gtaacagagc ttccattctt tgcatctaag gtaaggcttg ggaagaatgg | 900 |
| agttgaggaa gtgcttggat taggtgagct gtccggacttt gagaaagaag ggttggagaa | 960 |
| gctcaagagc gagctcaagt cttcgattga gaagggtatc aagtttgcaa atgataacta | 1020 |
| g | 1021 |

<210> SEQ ID NO 133
<211> LENGTH: 1015
<212> TYPE: DNA
<213> ORGANISM: Zea mays

<400> SEQUENCE: 133

| | | |
|---|---|---|
| atgaaggccg tcgctgatga gatccacctc ccagctcctc cgccgccgga gctactcctc | 60 |
| cgcatccggg cagcccgagc ggaaggtggc catcctcggg gcggcggggg gcatcgggca | 120 |
| gccgctgtcg ctgctcatga agcttaaccc actcgtctcc tccctctcgc tctacgatat | 180 |
| cgccggcacc ccaggtgtcg cggccgacgt ctcccacatc aactcccccg ccctggtgaa | 240 |
| gggtttcatg ggtgatgagc agcttgggga agcgctagag ggctcggacg tggtgatcat | 300 |
| accggccggc gtcccgagga agcccggcat gaccagggac gacctattca atatcaacgc | 360 |
| tggcatcgtt aagaacctca gcaccgccat cgccaagtac tgccccaatg cccttgtcaa | 420 |
| catgatcagc aaccctgtga actcaactgt accgattgct gctgaggttt tcaagaaggc | 480 |
| tgggacatat gatgagaaga agttgtttgg cgtgaccatt gttcgtgcta agactttcta | 540 |
| tgctgggaag gctaatttac cagttaccga tgtgaatgtc cctgttgttg gtggtcatgc | 600 |
| gggtatcact atcctgccgt tgttctcaca ggccacccct gcaaccaacg cattgtctga | 660 |
| tgaagacatc aaggctctca ccaagaggac acaggatggt ggaactgaag ttgtcgaggc | 720 |
| aaaggctggg aagggctctg caaccttgtc catggcgtat gctggtgctg tttttgcaga | 780 |

| | |
|---|---|
| tgcatgcttg aagggtctca atggagttcc ggatattgtt gagtgctctt ttgttcaatc | 840 |
| aactgtaaca gagcttccat tctttgcatc taaggtaagg cttgggaaga atggagttga | 900 |
| ggaagtgctt ggattaggtg agctgtcgga ctttgagaaa aagggttgg agaagctcaa | 960 |
| gagcgagctc aagtcttcga ttgagaaggg tatcaagttt gcaaatgata actag | 1015 |

<210> SEQ ID NO 134
<211> LENGTH: 1032
<212> TYPE: DNA
<213> ORGANISM: Glycine max

<400> SEQUENCE: 134

| | |
|---|---|
| atgaagccat cgatgctcag atctcttcac tctgccgcca cccgcggcgc ctcccacctc | 60 |
| tcccgccgtg gctacgcctc cgagccggtg ccggagcgca aggtggccgt tctaggtgcc | 120 |
| gccggcggga tcgggcaacc cctctcccett ctcatgaagc tcaacccct cgtttccagc | 180 |
| ctctccctct acgatatcgc cggaactccc ggtgtcgccg ccgatgtcag ccacatcaac | 240 |
| accggatctg aggtagtggg gtaccaaggt gacgaagagc tcggaaaagc tttggagggt | 300 |
| gcagatgttg ttataattcc tgctggtgtg cccagaaagc ctggaatgac tcgtgatgat | 360 |
| cttttttaaca tcaatgctgg cattgttgag acactgtgta ctgctattgc taagtactgc | 420 |
| cctcatgccc ttgttaacat gataagcaat cctgtgaact ccactgttcc tattgctgct | 480 |
| gaagttttca agaaggcagg aacgtatgat gagaagagat tgtttggtgt taccactgat | 540 |
| gttgttaggg caaaaacttt ctatgctggg aaagccaatg ttccagttgc tggtgttaat | 600 |
| gtacctgttg tgggtggcca tgcaggcatt actattctgc cattattttc tcaagccaca | 660 |
| ccaaaagcca atcttgatga tgatgtcatt aaggctctta caagaggac acaagatgga | 720 |
| ggaacagaag ttgtagaagc taaggctgga aagggttctg caactttgtc aatggcctat | 780 |
| gctggtgccc tatttgctga tgcttgcctt aagggcctca atggagtccc agatgttgtg | 840 |
| gagtgctcat tcgtgcaatc cactgttact gaacttccct actttgcttc caaggtgagg | 900 |
| cttgggaaga atggagtgga ggaagttctg ggcttaggac ctctctcaga ttttgagcaa | 960 |
| caaggcctcg aaagccttaa gcctgaactc aaatcatcaa ttgagaaggg aatcaaattt | 1020 |
| gccaaccagt aa | 1032 |

<210> SEQ ID NO 135
<211> LENGTH: 1026
<212> TYPE: DNA
<213> ORGANISM: Glycine max

<400> SEQUENCE: 135

| | |
|---|---|
| atgaagccat cgatgctcag atctcttcac tctgccgcca cccgcggcgc ctcccacctc | 60 |
| tcccgccgtg gctacgcctc cgagccggtg ccggagcgca aggtggccgt tctaggtgcc | 120 |
| gccggcggga tcgggcaacc cctctcccett ctcatgaagc tcaacccct cgtttccagc | 180 |
| ctctccctct acgatatcgc cggaactccc ggtgtcgccg ccgatgtcag ccacatcaac | 240 |
| accggatctg aggtagtggg gtaccaaggt gacgaagagc tcggaaaagc tttggagggt | 300 |
| gcagatgttg ttataattcc tgctggtgtg cccagaaagc ctggaatgac tcgtgatgat | 360 |
| cttttttaaca tcaatgctgg cattgttgag acactgtgta ctgctattgc taagtactgc | 420 |
| cctcatgccc ttgttaacat gataagcaat cctgtgaact ccactgttcc tattgctgct | 480 |
| gaagttttca agaaggcagg aacgtatgat gagaagagat tgtttggtgt taccattgtt | 540 |

| | |
|---|---|
| agggcaaaaa ctttctatgc tgggaaagcc aatgttccag ttgctggtgt taatgtacct | 600 |
| gttgtgggtg gccatgcagg cattactatt ctgccattat tttctcaagc cacaccaaaa | 660 |
| gccaatcttg atgatgatgt cattaaggct cttacaaaga ggacacaaga tggaggaaca | 720 |
| gaagttgtag aagctaaggc tggaaagggt tctgcaactt tgtcaatggc ctatgctggt | 780 |
| gccctatttg ctgatgcttg ccttaagggc ctcaatggag tcccagatgt tgtggagtgc | 840 |
| tcattcgtgc aatccactgt tactgaactt ccctactttg cttccaaggt gaggcttggg | 900 |
| aagaatggag tggaggaagt tctgggctta ggacctctct cagattttga gcaacaaggc | 960 |
| ctcgaaagcc ttaagcctga actcaaatca tcaattgaga agggaatcaa atttgccaac | 1020 |
| cagtaa | 1026 |

<210> SEQ ID NO 136
<211> LENGTH: 1041
<212> TYPE: DNA
<213> ORGANISM: Solanum lycopersicum

<400> SEQUENCE: 136

| | |
|---|---|
| atgtcaagga cctccatgtt gaaatccatc gtccgccgga gctccactgc cggagcatcc | 60 |
| tatgtatctc gccgtggatt cgcatcggga tccgcgccgg agaggaaagt tgcagttttg | 120 |
| ggggcagccg agggattgg acagccttta tctcttctaa tgaagcttaa ccctttagta | 180 |
| tccagccttt cactctacga tatcgccggt actcccggtg ttgccgccga tgttagtcac | 240 |
| atcaacacca gatctgaggt tgccggtttt gcaggagaag agcagctagg gcaggcactg | 300 |
| gaaggagctg atgttgttat cattcctgct ggtgtgcccc gaaagcctgg tatgacccga | 360 |
| gatgatctgt tcaacattaa tgcgggtatt gttaaatctc tatgcacggc cattgctaag | 420 |
| tactgcccca atgctctggt caatatgata agcaacccag tgaattccac tgtccctatt | 480 |
| gctgctgagg tgtttaagaa agctggaact tatgatgaaa agaagctctt tggagttacc | 540 |
| attgatgtgt taagggccaa gacattttat gctggaaaag ctaaagtaaa tgttgctgag | 600 |
| gtcaatctcc cagtagttgg tggtcatgct ggcataacta tcctcccatt attttctcaa | 660 |
| gccactccaa aggcaaatct atcatatgag gaaattgttg cactcacaaa gcgaacccaa | 720 |
| gatggtggga cagaagttgt agaagccaaa gctggaaagg gttcagccac cctctcaata | 780 |
| gcctatgctg gggctatttt tgccgatgct tgcttgaagg ggttgaatgg agttcccgat | 840 |
| gttgttgaat gtgcttttgt gcagtccaat gtcaccgagc ttcccttctt cgcatccaag | 900 |
| gtaagacttg ggaaaatgg agtggaggaa gtcctagggt tgggtccact taacgactac | 960 |
| gagaagcaag gacttgaggc tcttaagcca gagctgctct cctccattga aagggaatc | 1020 |
| aagtttgcca agaaaacta a | 1041 |

<210> SEQ ID NO 137
<211> LENGTH: 1035
<212> TYPE: DNA
<213> ORGANISM: Solanum lycopersicum

<400> SEQUENCE: 137

| | |
|---|---|
| atgtcaagga cctccatgtt gaaatccatc gtccgccgga gctccactgc cggagcatcc | 60 |
| tatgtatctc gccgtggatt cgcatcggga tccgcgccgg agaggaaagt tgcagttttg | 120 |
| ggggcagccg agggattgg acagccttta tctcttctaa tgaagcttaa ccctttagta | 180 |
| tccagccttt cactctacga tatcgccggt actcccggtg ttgccgccga tgttagtcac | 240 |
| atcaacacca gatctgaggt tgccggtttt gcaggagaag agcagctagg gcaggcactg | 300 |

```
gaaggagctg atgttgttat cattcctgct ggtgtgcccc gaaagcctgg tatgacccga    360
gatgatctgt tcaacattaa tgcgggtatt gttaaatctc tatgcacggc cattgctaag    420
tactgcccca atgctctggt caatatgata agcaacccag tgaattccac tgtccctatt    480
gctgctgagg tgtttaagaa agctggaact tatgatgaaa agaagctctt tggagttacc    540
atggttaggg ccaagacatt ttatgctgga aaagctaaag taaatgttgc tgaggtcaat    600
ctcccagtag ttggtggtca tgctggcata actatcctcc cattattttc tcaagccact    660
ccaaaggcaa atctatcata tgaggaaatt gttgcactca caaagcgaac ccaagatggt    720
gggacagaag ttgtagaagc caaagctgga aagggttcag ccaccctctc aatagcctat    780 gctgggcta tttttgccga tgcttgcttg aaggggttga atggagttcc cgatgttgtt    840
gaatgtgctt ttgtgcagtc caatgtcacc gagcttccct tcttcgcatc caaggtaaga    900
cttgggaaaa atggagtgga ggaagtccta gggttgggtc cacttaacga ctacgagaag    960
caaggacttg aggctcttaa gccagagctg ctctcctcca ttgaaaaggg aatcaagttt   1020
gccaaagaaa actaa                                                    1035

<210> SEQ ID NO 138
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 138

His His His His His His
1               5
```

TARGETED MODIFICATION OF MALATE DEHYDROGENASE

CROSS-REFERENCE TO RELATED APPLICATIONS

The present application is a continuation of U.S. patent application Ser. No. 13/875,992, filed May 2, 2013 which claims the benefit of U.S. Provisional Application No. 61/641,776, filed May 2, 2012 and U.S. Provisional Application No. 61/780,512, filed Mar. 13, 2013, the disclosures of which are hereby incorporated by reference in their entireties.

STATEMENT OF RIGHTS TO INVENTIONS MADE UNDER FEDERALLY SPONSORED RESEARCH

Not applicable.

TECHNICAL FIELD

The present disclosure is in the field of genomic engineering, particularly altered expression and/or targeted modification of an endogenous plant malate dehydrogenase (MDH) gene.

BACKGROUND

Biotechnology has emerged as an essential tool in efforts to meet the challenge of increasing global demand for food production. Conventional approaches to improving agricultural productivity, e.g. enhanced yield or engineered pest resistance, rely on either mutation breeding or introduction of novel genes into the genomes of crop species by transformation. Both processes are inherently nonspecific and relatively inefficient. For example, conventional plant transformation methods deliver exogenous DNA that integrates into the genome at random locations. Thus, in order to identify and isolate transgenic lines with desirable attributes, it is necessary to generate thousands of unique random-integration events and subsequently screen for the desired event. As a result, conventional plant trait engineering is a laborious, time-consuming, and unpredictable undertaking. Furthermore the random nature of these integrations makes it difficult to predict whether pleiotropic effects due to unintended genome disruption have occurred. As a result, the generation, isolation and characterization of plant lines with engineered transgenes or traits has been an extremely labor and cost-intensive process with a low probability of success.

Targeted gene modification overcomes the logistical challenges of conventional practices in plant systems, and as such has been a long-standing but elusive goal in both basic plant biology research and agricultural biotechnology. However, with the exception of "gene targeting" via positive-negative drug selection in rice or the use of pre-engineered restriction sites, targeted genome modification in all plant species, both model and crop, has until recently proven very difficult. Terada et al. (2002) *Nat Biotechnol* 20(10):1030; Terada et al. (2007) *Plant Physiol* 144(2):846; D'Halluin et al. (2008) *Plant Biotechnology J.* 6(1):93.

Recently, methods and compositions for targeted cleavage of genomic DNA have been described. Such targeted cleavage events can be used, for example, to induce targeted mutagenesis, induce targeted mutations (e.g., deletions, substitutions and/or insertions) of cellular DNA sequences, and facilitate targeted recombination and integration at a predetermined chromosomal locus. See, for example, Urnov et al. (2010) *Nature* 435(7042):646-51; United States Patent Publications 20030232410; 20050208489; 20050026157; 20050064474; 20060188987; 20090263900; 20090117617; 20100047805; 20110207221; 20110301073; 2011089775 and International Publication WO 2007/014275, the disclosures of which are incorporated by reference in their entireties for all purposes. Cleavage can occur through the use of specific nucleases such as engineered zinc finger nucleases (ZFNs), transcription-activator like effector nucleases (TALENs), homing endonucleases, or using the CRISPR/Cas system with an engineered crRNA/tracr RNA ('single guide RNA') to guide specific cleavage. U.S. Patent Publication No. 20080182332 describes the use of non-canonical zinc finger nucleases (ZFNs) for targeted modification of plant genomes; U.S. Patent Publication No. 20090205083 describes ZFN-mediated targeted modification of a plant EPSPS locus; U.S. Patent Publication No. 20100199389 describes targeted modification of a plant Zp15 locus and U.S. Patent Publication No. 20110167521 describes targeted modification of plant genes involved in fatty acid biosynthesis. In addition, Moehle et al. (2007) *Proc. Natl. Acad, Sci. USA* 104(9):3055-3060 describes using designed ZFNs for targeted gene addition at a specified locus.

Carbon assimilation is central to the metabolic functioning of all living organisms. The ability to synthesize ATP and utilize its energy for homeostasis, growth and reproduction is conserved across kingdoms and impacts a majority of known biological processes. A fundamental component of ATP synthesis in eukaryotes is the tricarboxylic acid (TCA) cycle, also known as the citric acid or Krebs cycle, which moves electrons from organic acids to the oxidized redox cofactors NAD+ and FAD, forming NADH, FADH2 and carbon dioxide. The TCA cycle takes place within mitochondria; in plants, intermediates produced during its reactions serve as substrates for numerous biosynthetic pathways; primary inputs for the production of aspartate, glutamate, nucleic acids, porphyrins and fatty acids originate from the TCA cycle. In addition, TCA cycle intermediates play a key role in the energetic processes of photorespiration and photosynthesis. Therefore, the TCA cycle is thought to act as a link between chloroplastic, mitochondrial and cytosolic redox functions.

Malate is one of the intermediates of the TCA cycle and acts as a substrate for both malic enzyme, which generates pyruvate, and malate dehydrogenase (MDH). MDH catalyzes the reversible reduction of oxaloacetate (OAA) to malate via NADH and is involved in the malate/aspartate shuttle. Most plants contain multiple isoforms of MDH, including mitochondrial and cytosolic enzymes, which are encoded by nuclear genes. The plant mitochondrial MDH (mMDH) participates in 3 types of reactions: conversion of malate to OAA, reduction of OAA to malate, and C4-pathway reduction of OAA. In maize (a C4 grass), there are 5 distinct MDH loci on 5 independent chromosomes, 2 of which encode cytosolic isoforms while the other 3 encode mitochondrial enzymes. Using classical mutant analyses, it was demonstrated that complete loss of function of the 2 cytosolic forms of MDH had no deleterious effects on plant growth and reproduction—the cytosolic function appeared to be dispensable. In contrast, complete loss of the 3 mitochondrial enzymes resulted in lethality—the plants needed at least one functional allele in order to be viable (Goodman et al. (1981) *Proc. Nat. Acad. Sci. USA* 78:1783-1785). Similarly, observations of naturally occurring spontaneous null alleles of mitochondrial MDH-1 (Mdh1-n) in soybean showed that there was no obvious plant phenotype as long as the mitochondrial Mdh2 gene remained stable (Imsande et al. (2001) *J. Heredity* 92:333-338).

Despite its fundamental role in plant metabolism, the functions of malate in the TCA cycle are still not completely understood. MDH-mutant plants exhibit slower growth rates and altered photorespiratory characteristics. See, e.g., Tomaz et al. (2010) *Plant Physiol.* 154(3):1143-1157. Antisense and RNAi studies in whole plants or fruit have shown contradictory results, including plants with increased dry (not fresh) fruit weights as well as plants having higher ascorbate levels in their leaves than wild-type controls but, when grown under short-day light conditions (which favor photorespiration), the plants displayed a dwarf phenotype and had reduced biomass in leaves, stems and roots. Nunes-Nesi et al. (2005) Plant Physiol. 137: 611-622); Nunes-Nesi et al. (2007) *Physiol. Plant.* 129:45-56); Nunes-Nesi (2008) *J. Exp. Bot.* 59:1675-1684; Finkmeier and Sweetlove (2009) *F1000 Biology Reports* 1:47; doi:10.3410/B1-47. Furthermore, mMDH anti-sense lines with reduced mMDH expression exhibited reduced activity (39% of wildtype) of this enzyme resulted in decreased root area and stunted root growth. Van der Merwe et al. (2009) *Plant Physiol.* 149: 653-669); Van Der Merwe et al. (2010) *Plant Physiol.* 153:611-621). Furthermore, mMDH anti-sense lines showed an increase in fruit desiccation (more $H_2O$ loss) and increased susceptibility to fungal infection. Centeno et al. (2011) *Plant Cell* 23:162-184. U.S. Patent Publication No. 20090123626 describes the use of MDH RNAi to reduce asparagine levels, which in turn lowers the level of acrylamide that accumulates upon processing-associated heating of the plant and plant products.

Thus, there remain needs for compositions and methods for altering expression of MDH genes, for example by targeted genomic modification of MDH genes, in plants for establishing stable, heritable genetic modifications in the plant and its progeny.

SUMMARY

The present disclosure provides methods and compositions for targeted modification of MDH gene(s) as well as cells (e.g., seeds), cell lines, organisms (e.g., plants), etc. comprising one or more targeted mutations in MDH. The MDH gene, may be, for example, a mitochondrial MDH gene (mMDH). As noted above, studies showing reduction of MDH enzymatic function by anti-sense and RNA-interference technology provide conflicting results on the effect(s) of MDH inhibition, for example on fruit yield. Based on these studies it would be expected that inhibition of TCA cycle flux would be have a negative effect on photosynthesis. Thus, it is surprising and unexpected that the present inventors have shown that plants (and plant cells) comprising targeted mutations in MDH that reduce MDH function (activity) result in increased crop yield from plants including the MDH-modified cells. Increased yield can include, for example, increased amount of fruit yield, increased biomass of the plant (or fruit of the plant), higher content of fruit flesh, larger plants, increased dry weight, increased solids context, higher total weight at harvest, enhanced intensity and/or uniformity of color of the crop, altered chemical (e.g., oil, fatty acid, carbohydrate, protein) characteristics, etc.

Thus, in one aspect, disclosed herein are plants comprising plant cells in which expression of an endogenous MDH gene is modified such that expression of MDH is reduced and in which the plant exhibits increased crop yield. In certain embodiments, expression of the endogenous MDH gene is altered using a fusion protein comprising a DNA-binding protein (e.g., zinc finger protein, TAL effector domain) and a functional domain. In certain embodiments, the plant cells contain a targeted modification of an MDH gene (e.g., mMDH), wherein the targeted modification that reduces MDH expression is induced by a nuclease, for example fusion protein comprising a DNA-binding domain and a functional domain (e.g., a zinc finger nuclease) that cleaves the endogenous gene and reduces its expression. The modification (e.g., deletion, substitution and/or insertion) may be, for example, to one or more amino acids in a NADH binding region of the MDH gene (e.g., first and/or second NADH binding regions of the gene). In certain embodiments, the modification comprises changing one or more amino acids in the first and/or second NADH binding region of an endogenous MDH gene in a plant cell, for example one or more amino acids at positions 104-136 and/or 171-220, numbered relative and aligned (e.g., FIG. 10) to a wild-type MDH amino acid sequence (e.g., SEQ ID NO:1 (wild-type tomato MDH sequence), SEQ ID NO:126 (wild-type corn MDH sequence) and/or SEQ ID NO:125 (wild-type soybean MDH sequence)).

The zinc finger protein may include the recognition helix regions show in a single row of Table 1A and/or bind to a target sequence as shown in Table 1B. In other embodiments, the nuclease comprises a TAL effector domain, a homing endonuclease and/or a Crispr/Cas single guide RNA. The targeted alteration of MDH expression (e.g., targeted genomic modification) may enhance or reduce MDH activity, for example reducing MDH activity by making a mutation that results in aberrant transcription of the gene product (e.g., via a frame-shift, novel stop codon or other mutation). In certain embodiments, the targeted modification using a nuclease comprises a small insertion and/or deletion, also known as an indel, for example an indel as shown in Table 4. The modification in the cell may be to one or more alleles (e.g., homozygotes, heterozygotes, in paralogous genes). Any of the plant cells described herein may be within a plant or plant part (e.g., seeds, flower, fruit), for example, any variety of: tomato (e.g., M82 or Moneymaker), soy, maize, potato, alfalfa or the like.

In another aspect, described herein is a DNA-binding domain (e.g., zinc finger protein (ZFP)) that specifically binds to an MDH gene. The zinc finger protein can comprise one or more zinc fingers (e.g., 2, 3, 4, 5, 6, 7, 8, 9 or more zinc fingers), and can be engineered to bind to any sequence within any MDH gene. Any of the zinc finger proteins described herein may bind to a target site within the coding sequence of MDH or within adjacent sequences (e.g., promoter or other expression elements), so long as modification of MDH expression is achieved. In certain embodiments, the zinc finger protein binds to a target site in an mMDH gene, for example, a target sequence as shown in Table 1B. In other embodiments, the recognition helix regions of the component zinc fingers are ordered finger 1 to finger 5 (F1 to F5) or finger 1 to finger 6 (F1 to F6) as shown in a single row of Table 1A. One or more of the component zinc finger binding domains of the zinc finger protein can be a canonical (C2H2) zinc finger or a non-canonical (e.g., C3H) zinc finger (e.g., the N-terminal and/or C-terminal zinc finger can be a non-canonical finger).

In another aspect, disclosed herein are fusion proteins, each fusion protein comprising a DNA-binding domain (e.g., a zinc finger protein) that specifically binds to one or more MDH genes. In certain embodiments, the proteins are fusion proteins comprising a MDH-binding zinc finger protein and a functional domain, for example a transcriptional activation domain, a transcriptional repression domain and/or a cleavage domain (or cleavage half-domain). In certain embodiments, the fusion protein is a zinc finger nuclease (ZFN). Cleavage domains and cleavage half domains can be obtained, for example, from various restriction endonucleases and/or homing endonucleases. In one embodiment, the cleavage half-domains are derived from a Type IIS restriction endonuclease (e.g., Fok I).

In other aspects, provided herein are polynucleotides encoding any of the DNA-binding domains (e.g., zinc finger proteins) and/or fusion proteins described herein. In certain embodiments, described herein is a ZFP expression vector comprising a polynucleotide, encoding one or more ZFPs described herein, operably linked to a promoter. In one embodiment, one or more of the ZFPs are ZFNs.

The ZFPs and fusion proteins comprising these ZFPs may bind to and/or cleave one or more MDH genes (e.g., an mMDH gene) within the coding region of the gene or in a non-coding sequence within or adjacent to the gene, such as, for example, a leader sequence, trailer sequence or intron, or promoter sequence, or within a non-transcribed region, either upstream or downstream of the coding region. In certain embodiments, the ZFPs or ZFNs bind to and/or cleave a coding sequence or a regulatory sequence of an MDH gene.

In another aspect, described herein are compositions comprising one or more proteins, fusion proteins and/or polynucleotides as described herein. Plant cells may contain one unique MDH gene target or multiple paralogous MDH targets. Thus, compositions described herein may comprise one or more ZFP-containing proteins (and polynucleotides encoding same) that target one or more MDH genes in a plant cell. The ZFPs may target all paralogous or homologous genes and selected particular paralogous or homologous genes in a plant cell or a combination of some paralogous and some homologous genes.

In another aspect, provided herein is a method for altering expression of one or more MDH genes (e.g., an endogenous mMDH gene) in a plant cell, the method comprising, expressing one or more DNA-binding domain containing proteins (e.g., zinc finger proteins) in the cell such that expression of MDH is altered. In certain embodiments, the methods comprise using a pair of zinc finger nucleases (proteins and/or polynucleotides encoding the proteins) to create a small insertion and/or deletion ("indel") that disrupts MDH expression. In other embodiments, the methods comprise using a pair of zinc finger nucleases to enhance MDH expression, for example via targeted insertion of a transgene or expression enhancing element. In other embodiments, the methods of altering MDH expression comprise using one or more zinc finger transcription factors (fusion proteins comprising MDH-binding zinc finger proteins and a functional domain that is a transcriptional regulatory domain, such as an activation or repression domain). In certain embodiments, the altered MDH expression/function results in increased photosynthesis within plant cells. In certain embodiments, the altered MDH expression/function results in modifications to the citric acid cycle within plant cells. In certain embodiments, the altered MDH expression/function results in higher levels of malate in the plant cell. In other embodiments, the altered expression/function of MDH results in reduced OAA levels in the cell. In one embodiment, the altered MDH expression/function in plant cells results in plants having increased yield. In certain embodiments, the increase in yield results in greater fresh weight of each fruit obtained and the total fresh weigh of all fruit harvested from the first truss of the mutant plants.

In another aspect, provided herein are nucleic acids and antibodies, and methods of using the same, for detecting and/or measuring altered expression of and modifications to MDH genes.

In another aspect, described herein is a method for modifying one or more MDH genes in a cell. In certain embodiments, the method comprising: (a) introducing, into the plant cell, one or more nucleases in protein form and/or one or more expression vectors encoding one or more nucleases (e.g., ZFNs) that bind to a target site in the one or more MDH genes under conditions such that the nucleases (e.g., ZFN(s)) is (are) expressed and the one or more MDH genes are cleaved, thereby modifying the one or more MDH genes. In certain embodiments, at least one target site is in an mMDH gene. In other embodiments, more than one MDH gene is cleaved. Furthermore, in any of the methods described herein, cleavage of the one or more genes may result in deletion, addition and/or substitution of nucleotides in the cleaved region, for example such that MDH activity is altered (e.g., enhanced or reduced).

In yet another aspect, described herein is a method for introducing an exogenous sequence (transgene) into the genome of a plant cell such that MDH activity in the plant cell is altered, the method comprising the steps of: (a) contacting the cell with an exogenous sequence (donor vector); and (b) expressing one or more nucleases (e.g., zinc finger nucleases) as described herein in the cell, wherein the one or more nucleases cleave chromosomal DNA; such that cleavage of chromosomal DNA in step (b) stimulates incorporation of the donor vector into the genome by homologous recombination. In certain embodiments, the exogenous sequence is introduced within an MDH gene. In other embodiments, the exogenous sequence is introduced near an MDH gene. MDH activity may be increased or reduced. In any of the methods described herein, the one or more nucleases may be fusions between the cleavage domain of a Type IIs restriction endonuclease and an engineered zinc finger binding domain. In other embodiments, the nuclease comprises a homing endonuclease, for example a homing endonuclease with a modified DNA-binding domain. In any of the methods described herein, the exogenous sequence may encode a protein product.

In a still further aspect, a plant cell obtained according to any of the methods described herein is also provided.

In another aspect, provided herein is a plant comprising a plant cell as described herein.

In another aspect, provided herein is a seed from a plant comprising the plant cell that is obtained as described herein.

In another aspect, provided herein is fruit obtained from a plant comprising plant cell obtained as described herein.

In any of the compositions (cells or plants) or methods described herein, the plant cell can comprise a monocotyledonous or dicotyledonous plant cell. In certain embodiments, the plant cell is a crop plant, for example, tomato (or other fruit crop), potato, maize, soy, alfalfa, etc.

BRIEF DESCRIPTION OF THE DRAWINGS

FIG. 1 is a schematic depicting various structural elements of the mitochondrial MDH (mMDH) gene from *Solanum lyocpersicum* (v. M82).

FIGS. 2A and 2B depict the genomic organization and sequence of the tomato mitochondrial malate dehydrogenase (mMDH) gene. FIG. 2A shows the target sites for the ZFNs (short left and right pointing arrows above exons) in exons 1, 3, 4 and 6. The labeled ZFN binding sequence number of FIG. 2A corresponds with the ZFN number described in Table 1; 107830L in Table 1 is described in FIG. 2A as 830L, 107830R in Table 1 is described in FIG. 2A as 830R, 107832L in Table 1 is described in FIG. 2A as 832L, 107832R in Table 1 is described in FIG. 2A as 832R, 107833L in Table 1 is described in FIG. 2A as 833L, 107833R in Table 1 is described in FIG. 2A as 833R, 107835L in Table 1 is described in FIG. 2A as 835L, 107835R in Table 1 is described in FIG. 2A as 835R. FIG. 2B (SEQ ID NO:2) shows the sequence of the mMDH locus; the exons are underlined and the ZFN target sites are indicated in bold type.

FIG. 7 depicts sequence analysis of small insertions or deletions ("indels") induced in the tomato mMDH gene by ZFN activity in protoplasts. The ZFNs were expressed transiently in tomato protoplasts and indels detected using HRM analysis. The mMDH target sites of each ZFN are shown with the binding sites underlined. Amplified products containing deletions (shown as −) or insertions (bold) are shown under each target sequence.

FIG. 8A is a graph which shows the measurement of mMDH activity in F2 plants derived from the line 107832_9-6 (−3 bps indel). "126 9-6 WT" identifies the biochemical assay results of F2 plant lacking the indel mutation, "115 9-6 M" identifies the F2 plants homozygous for the indel mutation, and "132 9-6 H" identifies F2 plant heterozygous for the indel mutation. FIG. 8B is a graph which shows the measurement of mMDH activity in F2 plants derived from the line 107832_10-2 (−2 bps indel). WT48 identifies F2 plants lacking the indel mutation, "M60" identifies F2 plants homozygous for the indel mutation, and "H 32" identifies F2 plant heterozygous for the indel mutation.

FIG. 10 is a sequence alignment of the soybean (SEQ ID NO:125), corn (SEQ ID NO:126), and tomato (SEQ ID NO:1) mMDH enzymes.

DETAILED DESCRIPTION

Figure 2A:
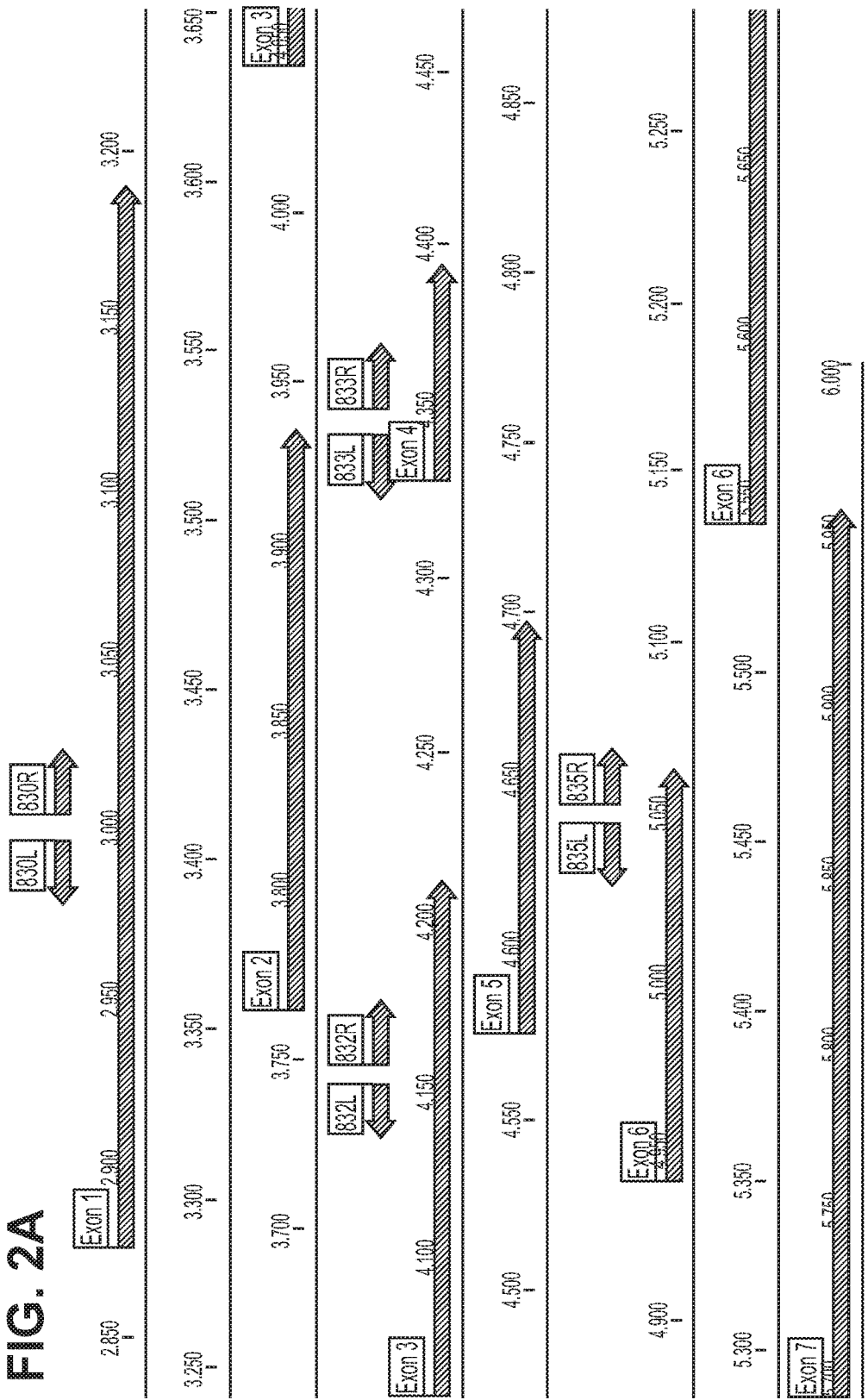
Figure 3:
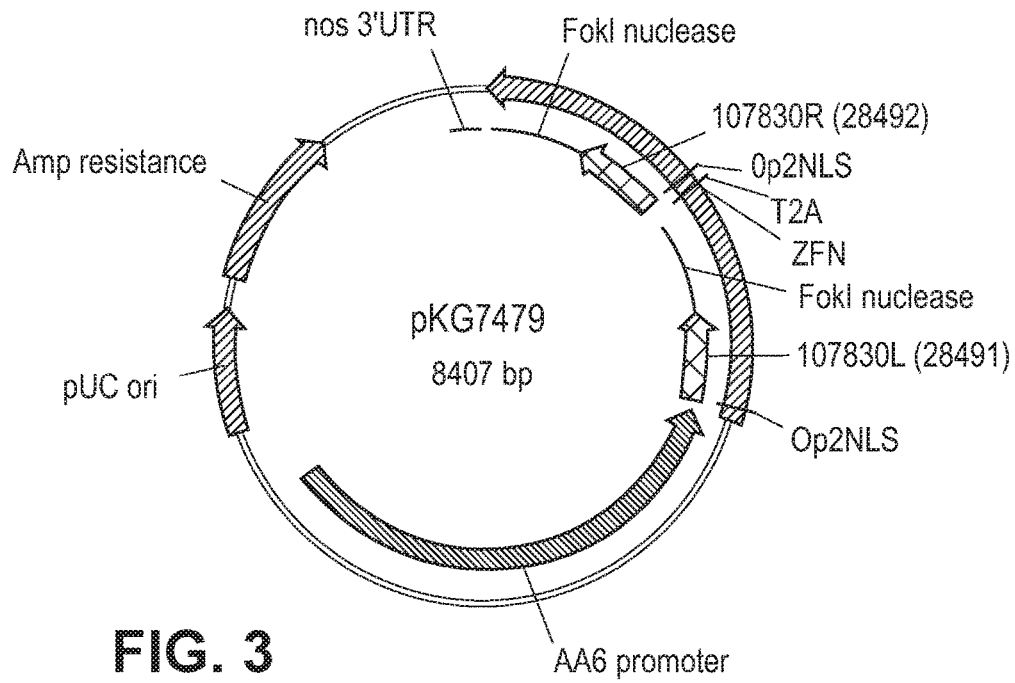
FIG. 3 is a schematic of showing a plasmid map of pKG7479.
Figure 4:
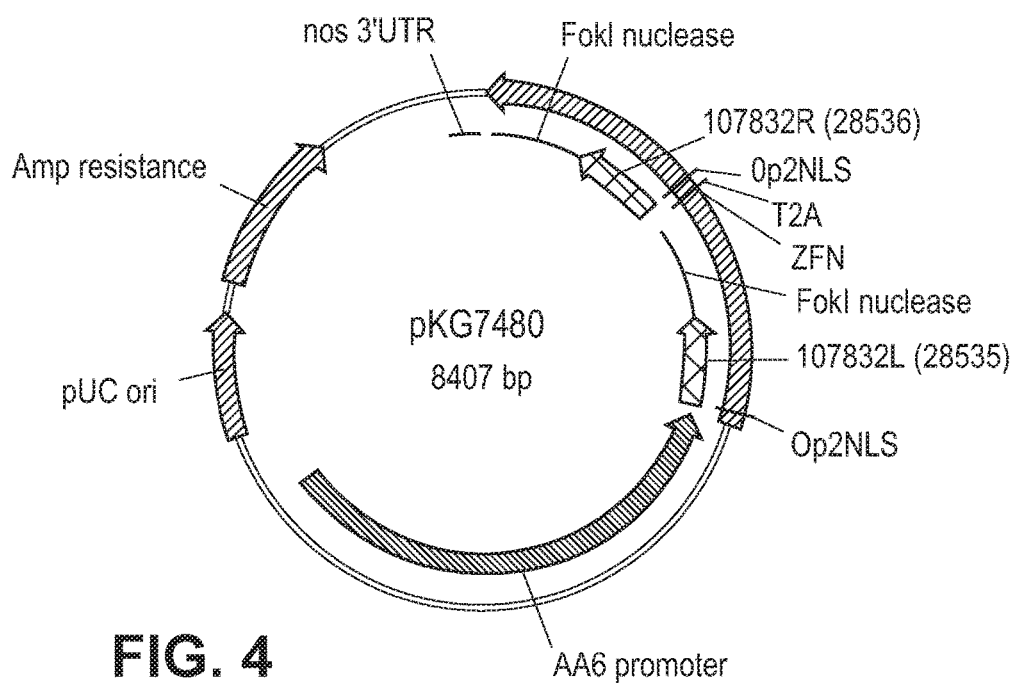
FIG. 4 is a schematic of showing a plasmid map of pKG7480.
Figure 5:
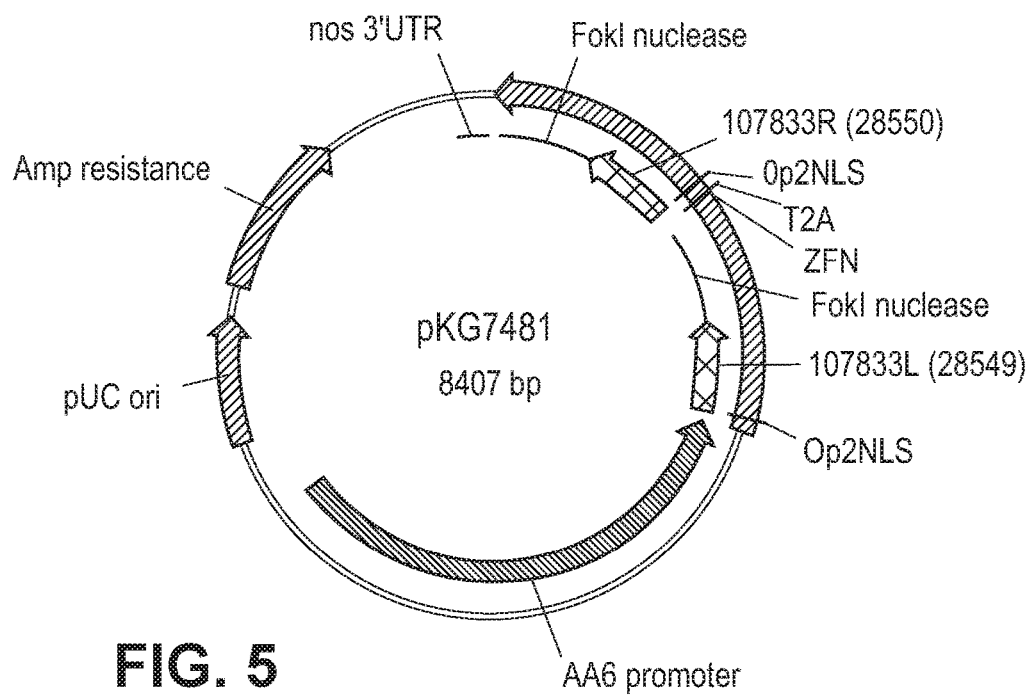
FIG. 5 is a schematic of showing a plasmid map of pKG7481.
Figure 6:
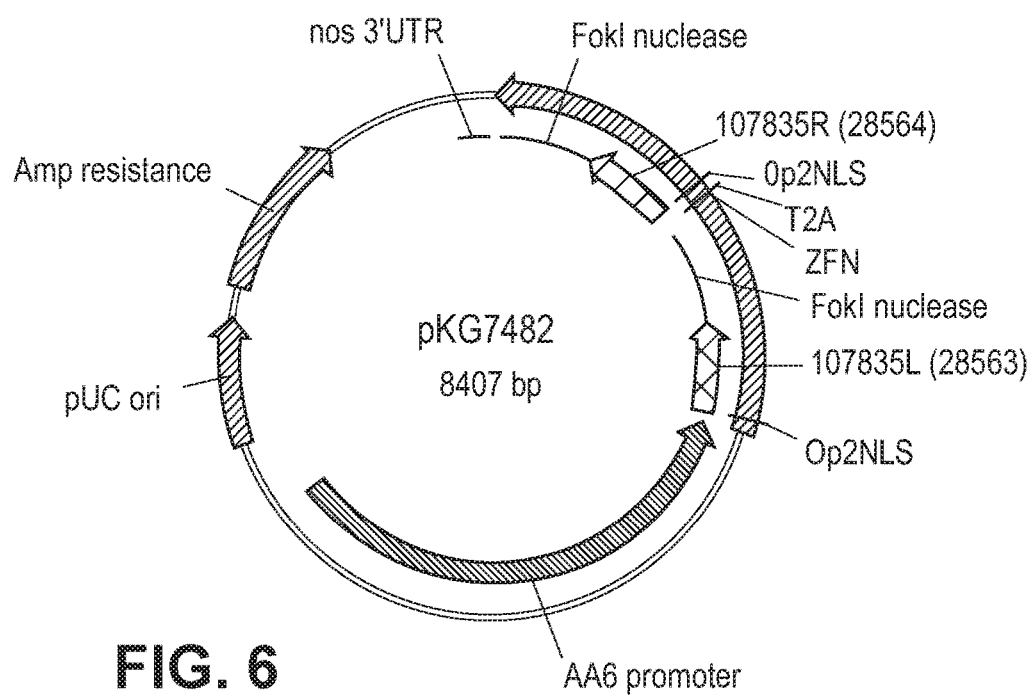
FIG. 6 is a schematic of showing a plasmid map of pKG7482.

The present disclosure relates to methods and compositions for altered expression of one or more malate dehydrogenase (MDH) genes in a plant cell or plant, for example targeted genomic modification of a MDH gene such as a mitochondrial malate dehydrogenase (mMDH) gene in a plant cell (e.g., maize, tomato, soy, etc.). In particular, expression of MDH is altered via use of fusion proteins comprising a DNA-binding domain (e.g., zinc finger protein) and functional domain (e.g., transcriptional regulatory domain and/or nuclease). In certain embodiments, targeted modification is achieved by cleaving an MDH gene using one or more nucleases (e.g., ZFNs) to produce modifications (e.g., mutations) at the MDH locus. Cleavage is targeted through the use of fusion proteins comprising a DNA-binding domain, such as a meganuclease DNA-binding domain, a leucine zipper DNA-binding domain, a TAL DNA-binding domain, a zinc finger protein (ZFP), a Crispr/Cas system or chimeric combinations of the aforementioned. In certain embodiments, the modification comprises mutation (substitutions, deletions and/or insertions) of the MDH gene such that one or more amino acids in the first and/or second NADH binding region of an endogenous MDH gene are altered, for example one or more amino acids at positions 104-136 and/or 171-220, numbered relative and aligned to SEQ ID NO:1 (wild-type tomato MDH sequence), SEQ ID NO:125 (wild-type corn MDH sequence) and/or SEQ ID NO:126 (wild-type soybean MDH sequence).

In certain embodiments, the nuclease(s) comprise one or more ZFNs. ZFNs typically comprise a cleavage domain (or a cleavage half-domain) and a zinc finger binding domain that binds to a target site in the endogenous MDH gene. The ZFNs may be introduced as proteins, as polynucleotides encoding these proteins and/or as combinations of polypeptides and polypeptide-encoding polynucleotides. Zinc finger nucleases typically function as dimeric proteins following dimerization of the cleavage half-domains and may form homodimers and/or heterodimers. Obligate heterodimeric ZFNs, in which the ZFN monomers bind to the "left" and "right" recognition domains can associate to form an active nuclease have been described. See, e.g., U.S. Patent Publication No. 2008/0131962. Thus, given the appropriate target sites, a "left" monomer could form an active ZF nuclease with any "right" monomer. This significantly increases the number of useful nuclease sites based on proven left and right domains that can be used in various combinations. For example, recombining the binding sites of 4 homodimeric ZF nucleases yields an additional 12 heterodimeric ZF nucleases. More importantly, it enables a systematic approach to transgenic design such that every new introduced exogenous sequence (transgene) becomes flanked with a unique ZFN site that can be used to excise the gene back out or to target additional genes next to it. Additionally, this method can simplify strategies of stacking into a single locus that is driven by ZFN-dependent double-strand breaks.

A zinc finger binding domain can be a canonical (C2H2) zinc finger or a non-canonical (e.g., C3H) zinc finger. Furthermore, the zinc finger binding domain can comprise one or more zinc fingers (e.g., 2, 3, 4, 5, 6, 7, 8, 9 or more zinc fingers), and can be engineered to bind to any sequence within any MDH gene. The recognition helix regions of exemplary MDH-binding zinc finger proteins for use in binding to an MDH gene are shown in Table 1A and exemplary target sites within an MDH gene are shown in Table 1B. The presence of such a fusion protein (or proteins) and/or polynucleotides encoding these fusion proteins) in a cell results in binding of the fusion protein(s) to its (their) binding site(s) and cleavage within the MDH gene(s).

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. Suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the internet. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is known to those with skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the probe sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, that uses a "donor" molecule to template repair of a "target" molecule (i.e., the one that experienced the double-strand break), and is variously known as "non-crossover gene conversion" or "short tract gene conversion,"

because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage domain" comprises one or more polypeptide sequences which possesses catalytic activity for DNA cleavage. A cleavage domain can be contained in a single polypeptide chain or cleavage activity can result from the association of two (or more) polypeptides.

A "cleavage half-domain" is a polypeptide sequence which, in conjunction with a second polypeptide (either identical or different) forms a complex having cleavage activity (preferably double-strand cleavage activity).

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528 and 2008/0131962, incorporated herein by reference in their entireties.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present in cells only during the early stages of development of a flower is an exogenous molecule with respect to the cells of a fully developed flower. Similarly, a molecule induced by heat shock is an exogenous molecule with respect to a non-heat-shocked cell. An exogenous molecule can comprise, for example, a coding sequence for any polypeptide or fragment thereof, a functioning version of a malfunctioning endogenous molecule or a malfunctioning version of a normally-functioning endogenous molecule. Additionally, an exogenous molecule can comprise a coding sequence from another species that is an ortholog of an endogenous gene in the host cell.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases. Thus, the term includes "transgenes" or "genes of interest" which are exogenous sequences introduced into a plant cell, e.g., into an MDH gene in a plant cell.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, protoplast transformation, silicon carbide (e.g., WHISKERS™), *Agrobacterium*-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soy, canola (rapeseed), and alfalfa. Plant cells may be from any part of the plant and/or from any stage of plant development.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

DNA-Binding Domains

Any DNA-binding domain can be used in the methods disclosed herein. In certain embodiments, the DNA binding domain comprises a zinc finger protein. A zinc finger binding domain comprises one or more zinc fingers. Miller et al. (1985) *EMBO J.* 4:1609-1614; Rhodes (1993) *Scientific*

American February: 56-65; U.S. Pat. No. 6,453,242. The zinc finger binding domains described herein generally include 2, 3, 4, 5, 6 or even more zinc fingers.

Typically, a single zinc finger domain is about 30 amino acids in length. Structural studies have demonstrated that each zinc finger domain (motif) contains two beta sheets (held in a beta turn which contains the two invariant cysteine residues) and an alpha helix (containing the two invariant histidine residues), which are held in a particular conformation through coordination of a zinc atom by the two cysteines and the two histidines.

Zinc fingers include both canonical $C_2H_2$ zinc fingers (i.e., those in which the zinc ion is coordinated by two cysteine and two histidine residues) and non-canonical zinc fingers such as, for example, $C_3H$ zinc fingers (those in which the zinc ion is coordinated by three cysteine residues and one histidine residue) and $C_4$ zinc fingers (those in which the zinc ion is coordinated by four cysteine residues). See also WO 02/057293 and also U.S. Patent Publication No. 20080182332 regarding non-canonical ZFPs for use in plants.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Enhancement of binding specificity for zinc finger binding domains has been described, for example, in WO 02/077227.

Since an individual zinc finger binds to a three-nucleotide (i.e., triplet) sequence (or a four-nucleotide sequence which can overlap, by one nucleotide, with the four-nucleotide binding site of an adjacent zinc finger), the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. As noted herein, binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain.

In a multi-finger zinc finger binding domain, adjacent zinc fingers can be separated by amino acid linker sequences of approximately 5 amino acids (so-called "canonical" inter-finger linkers) or, alternatively, by one or more non-canonical linkers. See, e.g., U.S. Pat. Nos. 6,453,242 and 6,534,261. For engineered zinc finger binding domains comprising more than three fingers, insertion of longer ("non-canonical") inter-finger linkers between certain of the zinc fingers may be desirable in some instances as it may increase the affinity and/or specificity of binding by the binding domain. See, for example, U.S. Pat. No. 6,479,626 and WO 01/53480. Accordingly, multi-finger zinc finger binding domains can also be characterized with respect to the presence and location of non-canonical inter-finger linkers. For example, a six-finger zinc finger binding domain comprising three fingers (joined by two canonical inter-finger linkers), a long linker and three additional fingers (joined by two canonical inter-finger linkers) is denoted a 2×3 configuration. Similarly, a binding domain comprising two fingers (with a canonical linker therebetween), a long linker and two additional fingers (joined by a canonical linker) is denoted a 2×2 configuration. A protein comprising three two-finger units (in each of which the two fingers are joined by a canonical linker), and in which each two-finger unit is joined to the adjacent two finger unit by a long linker, is referred to as a 3×2 configuration.

The presence of a long or non-canonical inter-finger linker between two adjacent zinc fingers in a multi-finger binding domain often allows the two fingers to bind to subsites which are not immediately contiguous in the target sequence. Accordingly, there can be gaps of one or more nucleotides between subsites in a target site; i.e., a target site can contain one or more nucleotides that are not contacted by a zinc finger. For example, a 2×2 zinc finger binding domain can bind to two six-nucleotide sequences separated by one nucleotide, i.e., it binds to a 13-nucleotide target site. See also Moore et al. (2001a) Proc. Natl. Acad. Sci. USA 98:1432-1436; Moore et al. (2001b) Proc. Natl. Acad. Sci. USA 98:1437-1441 and WO 01/53480.

As discussed previously, a target subsite is a three- or four-nucleotide sequence that is bound by a single zinc finger. For certain purposes, a two-finger unit is denoted a "binding module." A binding module can be obtained by, for example, selecting for two adjacent fingers in the context of a multi-finger protein (generally three fingers) which bind a particular six-nucleotide target sequence. Alternatively, modules can be constructed by assembly of individual zinc fingers. See also WO 98/53057 and WO 01/53480.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996)J. Mol. Biol. 263:163-180; Argast et al. (1998)J. Mol. Biol. 280:345-353 and the New England Biolabs catalogue. In addition, the DNA-binding specificity of homing endonucleases and meganucleases can be engineered to bind non-natural target sites. See, for example, Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66; U.S. Patent Publication No. 20070117128.

As another alternative, the DNA-binding domain may be derived from a leucine zipper protein. Leucine zippers are a class of proteins that are involved in protein-protein interactions in many eukaryotic regulatory proteins that are important transcriptional factors associated with gene expression. The leucine zipper refers to a common structural motif shared in these transcriptional factors across several kingdoms including animals, plants, yeasts, etc. The leucine zipper is formed by two polypeptides (homodimer or heterodimer) that bind to specific DNA sequences in a manner where the leucine residues are evenly spaced through an α-helix, such that the leucine residues of the two polypeptides end up on the same face of the helix. The DNA binding specificity of leucine zippers can be utilized in the DNA-binding domains disclosed herein.

In some embodiments, the DNA-binding domain is an engineered domain from a TAL effector derived from the plant pathogen *Xanthomonas* (see, Miller et al. (2011) *Nature Biotechnology* 29(2):143-8; Boch et al, (2009) *Science* 29 Oct. 2009 (10.1126/science.117881) and Moscou and Bogdanove, (2009) *Science* 29 Oct. 2009 (10.1126/science.1178817; and U.S. Patent Publication Nos. 20110239315, 20110145940 and 20110301073), incorporated by reference in their entireties herein.

The CRISPR (Clustered Regularly Interspaced Short Palindromic Repeats)/Cas (CRISPR Associated) nuclease system is a recently engineered nuclease system based on a bacterial system that can be used for genome engineering. It is based on part of the adaptive immune response of many bacteria and Archea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer". Cas9 cleaves the DNA to generate blunt ends at the DSB at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et at (2012) *Science* 337, p. 816-821, Jinek et al, (2013), *eLife* 2:e00471, and David Segal, (2013) *eLife* 2:e00563). Thus, the CRISPR/Cas system can be engineered to create a double-stranded break (DSB) at a desired target in a genome, and repair of the DSB can be influenced by the use of repair inhibitors to cause an increase in error prone repair.

Cleavage Domains

As noted above, the DNA-binding domain may be associated with a cleavage (nuclease) domain. For example, homing endonucleases may be modified in their DNA-binding specificity while retaining nuclease function. In addition, zinc finger proteins may also be fused to a cleavage domain to form a zinc finger nuclease (ZFN). The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). Non limiting examples of homing endonucleases and meganucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J Mol. Biol.* 263:163-180; Argast et al. (1998) *J Mol. Biol.* 280:345-353 and the New England Biolabs catalogue. One or more of these enzymes (or functional fragments thereof) can be used as a source of cleavage domains and cleavage half-domains.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI. This particular enzyme is active as a dimer. Bitinaite et al. (1998) *Proc. Natl. Acad. Sci. USA* 95: 10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-FokI fusions, two fusion proteins, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 2007/014275, incorporated by reference herein in its entirety.

To enhance cleavage specificity, cleavage domains may also be modified. In certain embodiments, variants of the cleavage half-domain are employed these variants minimize or prevent homodimerization of the cleavage half-domains. Non-limiting examples of such modified cleavage half-domains are described in detail in WO 2007/014275, incorporated by reference in its entirety herein. See, also, Examples. In certain embodiments, the cleavage domain comprises an engineered cleavage half-domain (also referred to as dimerization domain mutants) that minimize or prevent homodimerization are known to those of skill the art and described for example in U.S. Patent Publication Nos. 20050064474; 20060188987; 20070305346 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Additional engineered cleavage half-domains of FokI that form obligate heterodimers can also be used in the ZFNs described herein. Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055). In other embodiments, the engineered cleavage half domain comprises the "Sharkey" and/or "Sharkey'" mutations (see Guo et al, (2010) *J. Mol. Biol.* 400(1):96-107).

Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

Fusion Proteins

Methods for design and construction of fusion proteins (and polynucleotides encoding same) are known to those of skill in the art. For example, methods for the design and construction of fusion proteins comprising DNA-binding domains (e.g., zinc finger domains) and regulatory or cleavage domains (or cleavage half-domains), and polynucleotides encoding such fusion proteins, are described in U.S. Pat. Nos. 6,453,242 and 6,534,261 and U.S. Patent Publication Nos 2007/0134796; 2005/0064474; 20080182332; 20090205083; 20100199389; 20110167521, 20110239315, 20110145940 and 20110301073. herein incorporated by reference in their entireties. In certain embodiments, polynucleotides encoding the fusion proteins are constructed. These polynucleotides can be inserted into a vector and the vector can be introduced into a cell (see below for additional disclosure regarding vectors and methods for introducing polynucleotides into cells).

In certain embodiments of the methods described herein, a zinc finger nuclease comprises a fusion protein comprising a zinc finger binding domain and a cleavage half-domain from the FokI restriction enzyme, and two such fusion proteins are expressed in a cell. Expression of two fusion proteins in a cell can result from delivery of the two proteins to the cell; delivery of one protein and one nucleic acid encoding one of the proteins to the cell; delivery of two nucleic acids, each encoding one of the proteins, to the cell; or by delivery of a single nucleic acid, encoding both proteins, to the cell. In additional embodiments, a fusion protein comprises a single polypeptide chain comprising two cleavage half domains and a zinc finger binding domain. In this case, a single fusion protein is expressed in a cell and, without wishing to be bound by theory, is believed to cleave DNA as a result of formation of an intramolecular dimer of the cleavage half-domains.

In certain embodiments, the components of the fusion proteins (e.g., ZFP-FokI fusions) are arranged such that the zinc finger domain is nearest the amino terminus of the fusion protein, and the cleavage half-domain is nearest the carboxy-terminus. This mirrors the relative orientation of the cleavage domain in naturally-occurring dimerizing cleavage domains such as those derived from the FokI enzyme, in which the DNA-binding domain is nearest the amino terminus and the cleavage half-domain is nearest the carboxy terminus. In these embodiments, dimerization of the cleavage half-domains to form a functional nuclease is brought about by binding of the fusion proteins to sites on opposite DNA strands, with the 5' ends of the binding sites being proximal to each other.

In additional embodiments, the components of the fusion proteins (e.g., ZFP-FokI fusions) are arranged such that the cleavage half-domain is nearest the amino terminus of the fusion protein, and the zinc finger domain is nearest the carboxy-terminus. In these embodiments, dimerization of the cleavage half-domains to form a functional nuclease is brought about by binding of the fusion proteins to sites on opposite DNA strands, with the 3' ends of the binding sites being proximal to each other.

In yet additional embodiments, a first fusion protein contains the cleavage half-domain nearest the amino terminus of the fusion protein, and the zinc finger domain nearest the carboxy-terminus, and a second fusion protein is arranged such that the zinc finger domain is nearest the amino terminus of the fusion protein, and the cleavage half-domain is nearest the carboxy-terminus. In these embodiments, both fusion proteins bind to the same DNA strand, with the binding site of the first fusion protein containing the zinc finger domain nearest the carboxy terminus located to the 5' side of the binding site of the second fusion protein containing the zinc finger domain nearest the amino terminus.

In certain embodiments of the disclosed fusion proteins, the amino acid sequence between the zinc finger domain and the cleavage domain (or cleavage half-domain) is denoted the "ZC linker." The ZC linker is to be distinguished from the inter-finger linkers discussed above. See, e.g., U.S. Patent Publications 20050064474 and 20030232410, and International Patent Publication WO05/084190, for details on obtaining ZC linkers that optimize cleavage.

In one embodiment, the disclosure provides a nuclease (e.g., ZFN) comprising a zinc finger protein having one or more of the recognition helix amino acid sequences shown in Table 1A (e.g., a zinc finger protein made up of component zinc finger domains with the recognition helices as shown in a single row of Table 1A). In another embodiment, provided herein is a ZFP expression vector comprising a nucleotide sequence encoding a ZFP having one or more recognition helices shown in Table 1A, for example a ZFP having the recognition helix regions ordered and shown in a single row of Table 1A. In another embodiment, provided herein is a DNA-binding domain (e.g., ZFP) that binds to a target site as shown in Table 1B or a polynucleotide encoding a DNA-binding domain (e.g., ZFP) that binds to a target site shown in Table 1B.

Target Sites

The disclosed methods and compositions include fusion proteins comprising a DNA-binding domain (e.g., ZFP) and a regulatory domain or cleavage (e.g., nuclease) domain (or a cleavage half-domain), in which the DNA-binding domain (e.g., zinc finger domain), by binding to a sequence in cellular chromatin in one or more plant MDH genes, directs the activity of the transcriptional regulatory domain or cleavage domain (or cleavage half-domain) to the vicinity of the sequence and, hence, modulates transcription or induces cleavage in the vicinity of the target sequence.

As set forth elsewhere in this disclosure, a DNA-binding domain such as zinc finger domain can be engineered to bind to virtually any desired sequence. Accordingly, after identifying a region of interest containing a sequence at which gene regulation, cleavage, or recombination is desired, one or more zinc finger binding domains can be engineered to bind to one or more sequences in the region of interest. In certain embodiments, the ZFPs as described herein bind to a target site as shown in Table 1B.

Selection of a target site in a genomic region of interest in cellular chromatin of any MDH gene for binding by a DNA-binding domain (e.g., a target site) can be accomplished, for example, according to the methods disclosed in U.S. Pat. No. 6,453,242 and/or U.S. Patent Publication Nos. 20110239315, 20110145940 and 20110301073, which also discloses methods for designing ZFPs to bind to a selected sequence. It will be clear to those skilled in the art that simple visual inspection of a nucleotide sequence can also be used for selection of a target site. Accordingly, any means for target site selection can be used in the claimed methods.

Target sites are generally composed of a plurality of adjacent target subsites. A target subsite refers to the sequence (usually either a nucleotide triplet, or a nucleotide quadruplet that can overlap by one nucleotide with an adjacent quadruplet) bound by an individual zinc finger. See, for example, WO 02/077227. If the strand with which a zinc finger protein makes most contacts is designated the target strand "primary recognition strand," or "primary contact strand," some zinc finger proteins bind to a three base triplet in the target strand and a fourth base on the non-target strand. For zinc finger proteins, a target site generally has a length of at least 9 nucleotides and, accordingly, is bound by a zinc finger binding domain comprising at least three zinc fingers. However binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also possible.

It is not necessary for a target site to be a multiple of three nucleotides. For example, in cases in which cross-strand interactions occur (see, e.g., U.S. Pat. No. 6,453,242 and WO 02/077227), one or more of the individual zinc fingers of a multi-finger binding domain can bind to overlapping quadruplet subsites. As a result, a three-finger protein can bind a 10-nucleotide sequence, wherein the tenth nucleotide is part of a quadruplet bound by a terminal finger, a four-finger protein can bind a 13-nucleotide sequence, wherein the thirteenth nucleotide is part of a quadruplet bound by a terminal finger, etc.

The length and nature of amino acid linker sequences between individual zinc fingers in a multi-finger binding domain also affects binding to a target sequence. For example, the presence of a so-called "non-canonical linker," "long linker" or "structured linker" between adjacent zinc fingers in a multi-finger binding domain can allow those fingers to bind subsites which are not immediately adjacent. Non-limiting examples of such linkers are described, for example, in U.S. Pat. No. 6,479,626 and WO 01/53480. Accordingly, one or more subsites, in a target site for a zinc finger binding domain, can be separated from each other by 1, 2, 3, 4, 5 or more nucleotides. To provide but one example, a four-finger binding domain can bind to a 13-nucleotide target site comprising, in sequence, two contiguous 3-nucleotide subsites, an intervening nucleotide, and two contiguous triplet subsites. See, also, U.S. Patent Publication No. 20090305419 for compositions and methods for linking artificial nucleases to bind to target sites separated by different numbers of nucleotides. Distance between sequences (e.g., target sites) refers to the number of nucleotides or nucleotide pairs intervening between two sequences, as measured from the edges of the sequences nearest each other.

In certain embodiments, ZFPs with transcription factor function are designed, for example by constructing fusion proteins comprising a ZFP and a transcriptional regulatory domain (e.g., activation or repression domain). Non-limiting examples of suitable transcriptional regulatory domains that can be fused to DNA-binding domains for modulation of gene expression are described, for example, in U.S. Pat. Nos. 6,534,261; 6,824,978; 6,933,113 and 8,399,218 and U.S. Patent Publication No. 20080182332. For transcription factor function, simple binding and sufficient proximity to the promoter are all that is generally needed. Exact positioning relative to the promoter, orientation, and within limits, distance does not matter greatly. This feature allows considerable flexibility in choosing target sites for constructing artificial transcription factors. The target site recognized by the ZFP therefore can be any suitable site in the target gene that will allow activation or repression of gene expression by a ZFP, optionally linked to a regulatory domain. Preferred target sites include regions adjacent to, downstream, or upstream of the transcription start site. In addition, target sites that are located in enhancer regions, repressor sites, RNA polymerase pause sites, and specific regulatory sites (e.g., SP-1 sites, hypoxia response elements, nuclear receptor recognition elements, p53 binding sites), sites in the cDNA encoding region or in an expressed sequence tag (EST) coding region.

In other embodiments, \ nucleases are designed, for example ZFNs and/or TALENs. Expression of a nuclease comprising a fusion protein comprising a DNA-binding domain and a cleavage domain (or of two fusion proteins, each comprising a zinc finger binding domain and a cleavage half-domain), in a cell, effects cleavage in the vicinity of the target sequence. In certain embodiments, cleavage depends on the binding of two zinc finger domain/cleavage half-domain fusion molecules to separate target sites. The two target sites can be on opposite DNA strands, or alternatively, both target sites can be on the same DNA strand.

Regulation of Gene Expression

A variety of assays can be used to determine whether a DNA-binding protein such as a ZFP modulates gene expression. The activity of a particular protein can be assessed using a variety of in vitro and in vivo assays, by measuring, e.g., protein or mRNA levels, product levels, enzyme activity, transcriptional activation or repression of a reporter gene, using, e.g., immunoassays (e.g., ELISA and immunohistochemical assays with antibodies), hybridization assays (e.g., RNase protection, northerns, in situ hybridization, oligonucleotide array studies), colorimetric assays, amplification assays, enzyme activity assays, phenotypic assays, and the like.

DNA-binding proteins are typically first tested for activity in vitro using ELISA assays and then using a yeast expression system. For example, the ZFP is often first tested using a transient expression system with a reporter gene, and then regulation of the target endogenous gene is tested in cells and in whole plants, both in vivo and ex vivo. The DNA-binding protein can be recombinantly expressed in a cell, recombinantly expressed in cells transplanted into a plant, or recombinantly expressed in a transgenic plant, as well as administered as a protein to plant or cell using delivery vehicles described below. The cells can be immobilized, be in solution, be injected into a plant, or be naturally occurring in a transgenic or non-transgenic plant.

Modulation of gene expression is tested using one of the in vitro or in vivo assays described herein. Samples or assays are treated with a DNA-binding protein (e.g., ZFP) and compared to control samples without the test compound, to examine the extent of modulation. For regulation of endogenous gene expression, the DNA-binding protein typically has a $K_d$ of 200 nM or less, more preferably 100 nM or less, more preferably 50 nM, most preferably 25 nM or less.

The effects of the binding proteins can be measured by examining any of the parameters described above. Any suitable gene expression, phenotypic, or physiological change can be used to assess the influence of a DNA-binding protein (e.g., ZFP). When the functional consequences are determined using intact cells or plants, one can also measure a variety of effects such as plant growth, transcriptional changes to both known and uncharacterized genetic markers (e.g., northern blots or oligonucleotide array studies), changes in cell metabolism such as cell growth or pH changes, and changes in intracellular second messengers such as cGMP.

Preferred assays for regulation of endogenous gene expression can be performed in vitro. In one preferred in vitro assay format, ZFP regulation of endogenous gene expression in cultured cells is measured by examining protein production using an ELISA assay. The test sample is compared to control cells treated with an empty vector or an unrelated ZFP that is targeted to another gene.

In another embodiment, regulation of endogenous gene expression is determined in vitro by measuring the level of target gene mRNA expression. The level of gene expression is measured using amplification, e.g., using PCR (such as real-time PCR), LCR, or hybridization assays, e.g., northern hybridization, RNase protection, dot blotting. RNase protection is used in one embodiment. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using the target gene promoter operably linked to a reporter gene such as luciferase, green fluorescent protein, CAT, or β-gal. The reporter construct is typically co-transfected into a cultured cell. After treatment with the DNA-binding protein (e.g., ZFP) of choice, the amount of reporter gene transcription, translation, or activity is measured according to standard techniques known to those of skill in the art.

Transgenic and non-transgenic plants are also used as a preferred embodiment for examining regulation of endogenous gene expression in vivo. Transgenic plants can stably express the DNA-binding protein (e.g., ZFP) of choice. Alternatively, plants that transiently express the ZFP of choice, or to which the ZFP has been administered in a delivery vehicle, can be used. Regulation of endogenous gene expression is tested using any one of the assays described herein.

Methods for Targeted Cleavage

The disclosed methods and compositions can be used to cleave DNA at a region of interest in cellular chromatin (e.g., at a desired or predetermined site in a genome, for example, within or adjacent to a MDH gene). For such targeted DNA cleavage, a DNA-binding domain such as zinc finger binding domain is engineered to bind a target site at or near the predetermined cleavage site, and a fusion protein comprising the engineered DNA-binding domain and a cleavage domain is introduced and/or expressed from a polynucleotide in a cell. Upon binding of the zinc finger portion of the fusion protein to the target site, the DNA is cleaved near the target site by the cleavage domain.

Alternatively, two fusion proteins, each comprising a zinc finger binding domain and a cleavage half-domain, are expressed in a cell, and bind to target sites which are juxtaposed in such a way that a functional cleavage domain is reconstituted and DNA is cleaved in the vicinity of the target sites. In one embodiment, cleavage occurs between the target sites of the two zinc finger binding domains. One or both of the zinc finger binding domains can be engineered.

For targeted cleavage using a zinc finger binding domain-cleavage domain fusion polypeptide, the binding site can encompass the cleavage site, or the near edge of the binding site can be 1, 2, 3, 4, 5, 6, 10, 25, 50 or more nucleotides (or any integral value between 1 and 50 nucleotides) from the cleavage site. The exact location of the binding site, with respect to the cleavage site, will depend upon the particular cleavage domain, and the length of the ZC linker. For methods in which two fusion polypeptides, each comprising a zinc finger binding domain and a cleavage half-domain, are used, the binding sites generally straddle the cleavage site. Thus the near edge of the first binding site can be 1, 2, 3, 4, 5, 6, 10, 25 or more nucleotides (or any integral value between 1 and 50 nucleotides) on one side of the cleavage site, and the near edge of the second binding site can be 1, 2, 3, 4, 5, 6, 10, 25 or more nucleotides (or any integral value between 1 and 50 nucleotides) on the other side of the cleavage site. Methods for mapping cleavage sites in vitro and in vivo are known to those of skill in the art.

Thus, the methods described herein can employ an engineered zinc finger binding domain fused to a cleavage domain. In these cases, the binding domain is engineered to bind to a target sequence, at or near where cleavage is desired. The fusion protein, or a polynucleotide encoding same, is introduced into a plant cell. Once introduced into, or expressed in, the cell, the fusion protein binds to the target sequence and cleaves at or near the target sequence. The exact site of cleavage depends on the nature of the cleavage domain and/or the presence and/or nature of linker sequences between the binding and cleavage domains. In cases where two fusion proteins, each comprising a cleavage half-domain, are used, the distance between the near edges of the binding sites can be 1, 2, 3, 4, 5, 6, 7, 8, 9, 10, 25 or more nucleotides (or any integral value between 1 and 50 nucleotides). Optimal levels of cleavage can also depend on both the distance between the binding sites of the two fusion proteins (see, for example, Smith et al. (2000) *Nucleic Acids Res.* 28:3361-3369; Bibikova et al. (2001) *Mol. Cell. Biol.* 21:289-297) and the length of the ZC linker in each fusion protein. See, also, U.S. Pat. No. 7,888,121; U.S. Patent Publication 20050064474 and International Patent Publications WO05/084190, WO05/014791 and WO03/080809.

In certain embodiments, the cleavage domain comprises two cleavage half-domains, both of which are part of a single polypeptide comprising a binding domain, a first cleavage half-domain and a second cleavage half-domain. The cleavage half-domains can have the same amino acid sequence or different amino acid sequences, so long as they function to cleave the DNA.

Cleavage half-domains may also be provided in separate molecules. For example, two fusion polypeptides may be introduced into a cell, wherein each polypeptide comprises a binding domain and a cleavage half-domain. The cleavage half-domains can have the same amino acid sequence or different amino acid sequences, so long as they function to cleave the DNA. Further, the binding domains bind to target sequences which are typically disposed in such a way that, upon binding of the fusion polypeptides, the two cleavage half-domains are presented in a spatial orientation to each other that allows reconstitution of a cleavage domain (e.g., by dimerization of the half-domains), thereby positioning the half-domains relative to each other to form a functional cleavage domain, resulting in cleavage of cellular chromatin in a region of interest. Generally, cleavage by the reconstituted cleavage domain occurs at a site located between the two target sequences. One or both of the proteins can be engineered to bind to its target site.

The two fusion proteins can bind in the region of interest in the same or opposite polarity, and their binding sites (i.e., target sites) can be separated by any number of nucleotides, e.g., from 0 to 200 nucleotides or any integral value therebetween. In certain embodiments, the binding sites for two fusion proteins, each comprising a zinc finger binding domain and a cleavage half-domain, can be located between 5 and 18 nucleotides apart, for example, 5-8 nucleotides apart, or 15-18 nucleotides apart, or 6 nucleotides apart, or 16 nucleotides apart, as measured from the edge of each binding site nearest the other binding site, and cleavage occurs between the binding sites.

The site at which the DNA is cleaved generally lies between the binding sites for the two fusion proteins. Double-strand breakage of DNA often results from two single-strand breaks, or "nicks," offset by 1, 2, 3, 4, 5, 6 or more nucleotides, (for example, cleavage of double-stranded DNA by native Fok I results from single-strand breaks offset by 4 nucleotides). Thus, cleavage does not necessarily occur at exactly opposite sites on each DNA strand. In addition, the structure of the fusion proteins and the distance between the target sites can influence whether cleavage occurs adjacent a single nucleotide pair, or whether cleavage occurs at several sites. However, for many applications, including targeted recombination and targeted mutagenesis (see infra) cleavage within a range of nucleotides is generally sufficient, and cleavage between particular base pairs is not required.

As noted above, the fusion protein(s) as described herein can be introduced as polypeptides and/or polynucleotides. For example, two polynucleotides, each comprising sequences encoding one of the aforementioned polypeptides, can be introduced into a cell, and when the polypeptides are expressed and each binds to its target sequence, cleavage occurs at or near the target sequence. Alternatively, a single polynucleotide comprising sequences encoding both fusion polypeptides is introduced into a cell. Polynucleotides can be DNA, RNA or any modified forms or analogues or DNA and/or RNA.

To enhance cleavage specificity, additional compositions may also be employed in the methods described herein. For example, single cleavage half-domains can exhibit limited double-stranded cleavage activity. In methods in which two fusion proteins, each containing a three-finger zinc finger domain and a cleavage half-domain, are introduced into the cell, either protein specifies an approximately 9-nucleotide target site. Although the aggregate target sequence of 18 nucleotides is likely to be unique in a mammalian and plant genomes, any given 9-nucleotide target site occurs, on average, approximately 23,000 times in the human genome. Thus, non-specific cleavage, due to the site-specific binding of a single half-domain, may occur. Accordingly, the methods described herein contemplate the use of a dominant-negative mutant of a cleavage half-domain such as Fok I (or a nucleic acid encoding same) that is expressed in a cell along with the two fusion proteins. The dominant-negative mutant is capable of dimerizing but is unable to cleave, and also blocks the cleavage activity of a half-domain to which it is dimerized. By providing the dominant-negative mutant in molar excess to the fusion proteins, only regions in which both fusion proteins are bound will have a high enough local concentration of functional cleavage half-domains for dimerization and cleavage to occur. At sites where only one of the two fusion proteins is bound, its cleavage half-domain forms a dimer with the dominant negative mutant half-domain, and undesirable, non-specific cleavage does not occur.

Expression Vectors

A nucleic acid encoding one or more fusion proteins (e.g., ZFNs) as described herein can be cloned into a vector for transformation into prokaryotic or eukaryotic cells for replication and/or expression. Vectors can be prokaryotic vectors (e.g., plasmids, or shuttle vectors, insect vectors) or eukaryotic vectors. A nucleic acid encoding a fusion protein can also be cloned into an expression vector, for administration to a cell.

To express the fusion proteins (e.g., ZFNs), sequences encoding the fusion proteins are typically subcloned into an expression vector that contains a promoter to direct transcription. Suitable prokaryotic and eukaryotic promoters are well known in the art and described, e.g., in Sambrook et al., *Molecular Cloning, A Laboratory Manual* (2nd ed. 1989; 3$^{rd}$ ed., 2001); Kriegler, *Gene Transfer and Expression: A Laboratory Manual* (1990); and *Current Protocols in Molecular Biology* (Ausubel et al., supra. Bacterial expression systems for expressing the proteins are available in, e.g., *E. coli, Bacillus* sp., and *Salmonella* (Palva et al., *Gene* 22:229-235 (1983)). Kits for such expression systems are commercially available. Eukaryotic expression systems for mammalian cells, yeast, and insect cells are well known by those of skill in the art and are also commercially available.

The promoter used to direct expression of a fusion protein-encoding nucleic acid depends on the particular application. For example, a strong constitutive promoter suited to the host cell is typically used for expression and purification of fusion proteins.

In contrast, when a fusion protein is administered in vivo for regulation of a plant gene (see, "Nucleic Acid Delivery to Plant Cells" section below), either a constitutive, regulated (e.g., during development, by tissue or cell type, or by the environment) or an inducible promoter is used, depending on the particular use of the fusion protein. Non-limiting examples of plant promoters include promoter sequences derived from *A. thaliana* ubiquitin-3 (ubi-3) (Callis, et al., 1990, *J. Biol. Chem.* 265-12486-12493); *A. tumifaciens* mannopine synthase (Δmas) (Petolino et al., U.S. Pat. No. 6,730,824); and/or Cassava Vein Mosaic Virus (CsVMV) (Verdaguer et al., 1996, *Plant Molecular Biology* 31:1129-1139). See, also, Examples.

In addition to the promoter, the expression vector typically contains a transcription unit or expression cassette that contains all the additional elements required for the expression of the nucleic acid in host cells, either prokaryotic or eukaryotic. A typical expression cassette thus contains a promoter (comprising ribosome binding sites) operably linked, e.g., to a nucleic acid sequence encoding the fusion protein, and signals required, e.g., for efficient polyadenylation of the transcript, transcriptional termination, or translation termination. Additional elements of the cassette may include, e.g., enhancers, heterologous splicing signals, the 2A sequence from *Thosea asigna* virus (Mattion et al. (1996) *J. Virol.* 70:8124-8127), and/or a nuclear localization signal (NLS).

The particular expression vector used to transport the genetic information into the cell is selected with regard to the intended use of the fusion proteins, e.g., expression in plants, animals, bacteria, fungus, protozoa, etc. (see expression vectors described below). Standard bacterial and animal expression vectors are known in the art and are described in detail, for example, U.S. Patent Publication 20050064474A1 and International Patent Publications WO05/084190, WO05/014791 and WO03/080809.

Standard transfection methods can be used to produce bacterial, plant, mammalian, yeast or insect cell lines that express large quantities of protein, which can then be purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds., 1983).

Any of the well-known procedures for introducing foreign nucleotide sequences into such host cells may be used. These include the use of calcium phosphate transfection, polybrene, protoplast fusion, electroporation, ultrasonic methods (e.g., sonoporation), liposomes, microinjection, naked DNA, plasmid vectors, viral vectors, *Agrobacterium*-mediated transformation, silicon carbide (e.g., WHISKERS™) mediated transformation, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Nucleic Acid Delivery to Plant Cells

As noted above, DNA constructs may be introduced into (e.g., into the genome of) a desired plant host by a variety of conventional techniques. For reviews of such techniques see, for example, Weissbach & Weissbach *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9. See, also, U.S. Patent Publication Nos. 20090205083; 20100199389; 20110167521 and 20110189775, incorporated herein by reference in their entireties.

For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al. (1987) *Nature* 327:70-73). Alternatively, the DNA construct can be introduced into the plant cell via nanoparticle transformation (see, e.g., U.S. Patent Publication No. 20090104700, which is incorporated herein by reference in its entirety). Alternatively, the DNA constructs may be combined with suitable T-DNA border/flanking regions and introduced into a conventional *Agrobacterium tumefaciens* host vector. *Agrobacterium tumefaciens*-mediated transformation techniques, including disarming of oncogenes and the development and use of binary vectors, are well described in the scientific literature. See, for example Horsch et al. (1984) *Science* 233:496-498, and Fraley et al. (1983) *Proc. Nat'l. Acad. Sci. USA* 80:4803.

In addition, gene transfer may be achieved using non-*Agrobacterium* bacteria or viruses such as *Rhizobium* sp. NGR234, *Sinorhizoboium meliloti, Mesorhizobium loti*, potato virus X, cauliflower mosaic virus and cassava vein mosaic virus and/or tobacco mosaic virus, See, e.g., Chung et al. (2006) *Trends Plant Sci.* 11(1):1-4.

The virulence functions of the *Agrobacterium tumefaciens* host will direct the insertion of a T-strand containing the construct and adjacent marker into the plant cell DNA when the cell is infected by the bacteria using binary T-DNA vector (Bevan (1984) *Nuc. Acid Res.* 12:8711-8721) or the co-cultivation procedure (Horsch et al. (1985) *Science* 227: 1229-1231). Generally, the *Agrobacterium* transformation system is used to engineer dicotyledonous plants (Bevan et al. (1982) *Ann. Rev. Genet* 16:357-384; Rogers et al. (1986) *Methods Enzymol.* 118:627-641). The *Agrobacterium* transformation system may also be used to transform, as well as transfer, DNA to monocotyledonous plants and plant cells. See U.S. Pat. No. 5,591,616; Hernalsteen et al. (1984)

EMBO J 3:3039-3041; Hooykass-Van Slogteren et al. (1984) Nature 311:763-764; Grimsley et al. (1987) Nature 325:1677-179; Boulton et al. (1989) Plant Mol. Biol. 12:31-40; and Gould et al. (1991) Plant Physiol. 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) EMBO J 3:2717-2722, Potrykus et al. (1985) Molec. Gen. Genet. 199:169-177; Fromm et al. (1985) Proc. Nat. Acad. Sci. USA 82:5824-5828; and Shimamoto (1989) Nature 338:274-276) and electroporation of plant tissues (D'Halluin et al. (1992) Plant Cell 4:1495-1505). Additional methods for plant cell transformation include microinjection, silicon carbide (e.g., WHISKERS™) mediated DNA uptake (Kaeppler et al. (1990) Plant Cell Reporter 9:415-418), and microprojectile bombardment (see Klein et al. (1988) Proc. Nat. Acad. Sci. USA 85:4305-4309; and Gordon-Kamm et al. (1990) Plant Cell 2:603-618).

The disclosed methods and compositions can be used to insert exogenous sequences into an MDH gene. This is useful inasmuch as expression of an introduced transgene into a plant genome depends critically on its integration site. Accordingly, genes encoding, e.g., herbicide tolerance, insect resistance, nutrients, antibiotics or therapeutic molecules can be inserted, by targeted recombination, into regions of a plant genome favorable to their expression.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al. (1987) Ann. Rev. of Plant Phys. 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., *petunia*, rose, *chrysanthemum*), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna,* and *Zea.*

The introduction of nucleic acids introduced into a plant cell can be used to confer desired traits on essentially any plant. In certain embodiments, the altered MDH expression/function in plant cells results in plants having increased amount of fruit yield, increased biomass of plant (or fruit of the plant), higher content of fruit flesh, concentrated fruit set, larger plants, increased fresh weight, increased dry weight, increased solids context, higher total weight at harvest, enhanced intensity and/or uniformity of color of the crop, altered chemical (e.g., oil, fatty acid, carbohydrate, protein) characteristics, etc.

One with skill in the art will recognize that an exogenous sequence can be transiently incorporated into a plant cell. The introduction of an exogenous polynucleotide sequence can utilize the cell machinery of the plant cell in which the sequence has been introduced. The expression of an exogenous polynucleotide sequence comprising a ZFN that is transiently incorporated into a plant cell can be assayed by analyzing the genomic DNA of the target sequence to identify and determine any indels, inversions, or insertions. These types of rearrangements result from the cleavage of the target site within the genomic DNA sequence, and the subsequent DNA repair. In addition, the expression of an exogenous polynucleotide sequence can be assayed using methods which allow for the testing of marker gene expression known to those of ordinary skill in the art. Transient expression of marker genes has been reported using a variety of plants, tissues, and DNA delivery systems. Transient analyses systems include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present disclosure encompasses the use of any transient expression system to evaluate a site specific endonuclease (e.g., ZFN) and to introduce mutations within an MDH target gene. Examples of plant tissues envisioned to test in transients via an appropriate delivery system would include but are not limited to leaf base tissues, callus, cotyledons, roots, endosperm, embryos, floral tissue, pollen, and epidermal tissue.

One of skill in the art will recognize that an exogenous polynucleotide sequence can be stably incorporated in transgenic plants. Once the exogenous polynucleotide sequence is confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing stably inserted gene constructs, or plant cell containing target gene altered genomic DNA which results from the transient expression of a site-specific endonuclease (e.g., ZFN). These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays (ELISA), where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the mRNA is present or the amount of mRNA has increased, it can be assumed that the corresponding transgene is being expressed. Other methods of measuring gene and/or encoded polypeptide activity can be used. Different types of enzymatic assays can be used, depending on the substrate used and the method of detecting the increase or decrease of a reaction product or by-product. In addition, the levels of polypeptide expressed can be measured immunochemically, i.e., ELISA, RIA, EIA and other antibody based assays well known to those of skill in the art, such as by electrophoretic detection assays (either with staining or western blotting). As one non-limiting example, the detection of the AAD-1 and PAT proteins using an ELISA assay is described in U.S. Patent Publication No. 20090093366, which reference is hereby incorporated by reference in its entirety herein. A transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

Fusion proteins (e.g., ZFNs) and expression vectors encoding fusion proteins can be administered directly to the plant for gene regulation, targeted cleavage, and/or recombination. In certain embodiments, the plant contains multiple paralogous MDH target genes. Thus, one or more different fusion proteins or expression vectors encoding fusion proteins may be administered to a plant in order to target one or more of these paralogous genes in the plant.

Administration of effective amounts is by any of the routes normally used for introducing fusion proteins into ultimate contact with the plant cell to be treated. The ZFPs are administered in any suitable manner, preferably with acceptable carriers. Suitable methods of administering such modulators are available and well known to those of skill in the art, and, although more than one route can be used to administer a particular composition, a particular route can often provide a more immediate and more effective reaction than another route.

Carriers may also be used and are determined in part by the particular composition being administered, as well as by the particular method used to administer the composition. Accordingly, there is a wide variety of suitable formulations of carriers that are available.

EXAMPLES

Example 1: Characterization of the Mitochondrial Malate Dehydrogenase (mMDH) Target Gene from Tomato (*Solanum lycopersicum*)

The malate dehydrogenase (MDH) gene is commonly present as multiple paralogous copies within an organism. Despite the presence of similar paralogous malate dehydrogenase gene sequences within an organism, a single mitochondrial malate dehydrogenase (mMDH) gene sequence was identified and isolated from *Solanum lycopersicum*. Initially, the mitochondrial malate dehydrogenase (mMDH) gene sequence was identified from several polynucleotide sequence databases by comparing portions of known malate dehydrogenase gene sequences, which were described in the literature, with the many different polynucleotide sequences contained in the polynucleotide sequence databases. After numerous comparisons of sequence alignments, the complete sequences of two different malate dehydrogenase gene sequences were identified; the mMDH sequence (described below) and the glycosomal MDH (gMDH) sequence (Accession Number: AY725476). The sequence database screening efforts identified the mMDH locus as Accession Number: Solyc07g062650 (SEQ ID NO:1) from the tomato genomic sequence database available online at Solgenomics (see, also, Bombarely et al. (2011) *Nuc Acids Res.* (Database issue):D 1149-55).

The mMDH gene sequence identified in silico was used to confirm the mMDH gene sequence from two distinct tomato genotypes, M82 and Moneymaker. Polymerase Chain Reaction (PCR) primers were designed based on the identified in silico mMDH gene sequence. A PCR fragment of approximately 6 kb was isolated from each tomato genotype, cloned and sequenced. Surprisingly, as minor differences are typically expected, the sequenced mMDH genes from the tomato genotypes showed no difference with the mMDH locus which was originally identified and isolated in silico.

The isolated novel mMDH gene sequences were used for further zinc finger reagent design.

Example 2: Production of Zinc Finger Proteins Designed to Bind the Mitochondrial Malate Dehydrogenase (mMDH) Gene Zinc finger proteins directed against DNA sequences encoding various functional domains in the *S. lycopersicum* v. M82 mMDH gene coding region (see, FIG. 1) were designed as previously described. See, e.g., Urnov et al. (2005) Nature 435:646-651. Exemplary target sequence and recognition helices are shown in Tables 1A (recognition helix regions designs) and Table 1B (target sites). In Table 1B, nucleotides in the target site that are contacted by the ZFP recognition helices are indicated in uppercase letters; non-contacted nucleotides indicated in lowercase.

TABLE 1A

Tomato mMDH-binding zinc finger designs

| ZFN Number/ subunit | Finger 1 (F1) | Finger 2 (F2) | Finger 3 (F3) | Finger 4 (F4) | Finger 5 (F5) | Finger 6 (F6) |
|---|---|---|---|---|---|---|
| 107830R/ 28492 | RSDDLSE (SEQ ID NO: 11) | TNSNRKR (SEQ ID NO: 12) | RSDHLST (SEQ ID NO: 13) | TNSNRIT (SEQ ID NO: 14) | RREDLIT (SEQ ID NO: 15) | TSSNLSR (SEQ ID NO: 16) |
| 107830L/ 28491 | QSSDLSR (SEQ ID NO: 17) | TSGNLTR (SEQ ID NO: 18) | RSDYLSK (SEQ ID NO: 19) | TSSVRTT (SEQ ID NO: 20) | TSGNLTR (SEQ ID NO: 18) | QRSHLSD (SEQ ID NO: 22) |
| 107832R/ 28536 | RSDTLSV (SEQ ID NO: 23) | DNSTRIK (SEQ ID NO: 24) | RSDHLSE (SEQ ID NO: 25) | TSGSLTR (SEQ ID NO: 26) | RSDALSR (SEQ ID NO: 27) | TSGNLTR (SEQ ID NO: 18) |
| 107832L/ 28535 | RSDNLAR (SEQ ID NO: 29) | QRGNRNT (SEQ ID NO: 30) | DSSDRKK (SEQ ID NO: 31) | DRSNLSR (SEQ ID NO: 32) | LRHHLTR (SEQ ID NO: 33) | — |
| 107833R/ 28550 | DRSNLSR (SEQ ID NO: 32) | LRQNLIM (SEQ ID NO: 35) | RSDALSE (SEQ ID NO: 36) | RSSTRKT (SEQ ID NO: 37) | DRSALSR (SEQ ID NO: 38) | RSDALAR (SEQ ID NO: 39) |
| 107833L/ 28549 | QSGNLAR (SEQ ID NO: 40) | SEQ ID NO: 41 NRYDLHK | DRSNLSR (SEQ ID NO: 32) | LRFARDA (SEQ ID NO: 43) | RSDNLAR (SEQ ID NO: 29) | RSDHLTQ (SEQ ID NO: 45) |
| 107835R/ 28564 | DRSDLSR (SEQ ID NO: 46) | QAGNLKK (SEQ ID NO: 47) | QSGSLTR (SEQ ID NO: 48) | RSDNLRE (SEQ ID NO: 49) | DSSDRKK (SEQ ID NO: 31) | — |
| 107835L/ 28563 | DRSNLSR (SEQ ID NO: 32) | LKQHLTR (SEQ ID NO: 52) | QSSDLSR (SEQ ID NO: 17) | QSGNLAR (SEQ ID NO: 40) | RSDHLSQ (SEQ ID NO: 55) | QNAHRIT (SEQ ID NO: 56) |

TABLE 1B

Target Sequences for zinc finger proteins

| Zinc Finger Number | Target Sequence |
|---|---|
| 107830R | agcatcctatgtatctcgccgtgGATTCGCATCGGGATCCG (SEQ ID NO: 3) |
| 107830L | cggatcccgatgcgaatccacggCGAGATACATAGGATGCT (SEQ ID NO: 4)* |
| 107832R | ctctaggagttaccatgcttGATGTGGTTAGGGCCAAG (SEQ ID NO: 5) |
| 107832L | cttggccctaaccacatcaagcatGGTAACTCCAAAGAG (SEQ ID NO: 6)* |
| 107833R | ttcagaggtcaatctcccagtagttgGTGGTCATGCTGgCAT AAC (SEQ ID NO: 7) |
| 107833L | gttatgccagcatgaccaccaactacTGGGAGATTGACcTCT GAA (SEQ ID NO: 8)* |
| 107835R | gtcaccgagcttcccttcttcgcaTCCAAGGTAaTAAGCC (SEQ ID NO: 9) |
| 107835L | ggcttattaccttggatgcgaAGAAGGGAAGCTcGGTGAC (SEQ ID NO: 10)* |

*indicates the binding sequences of the complement or reverse orientation of SEQ ID NO: 2

The mMDH zinc finger designs were incorporated into vectors encoding a protein having at least one finger with a CCHC structure. See, U.S. Patent Publication No. 2008/ 0182332. In particular, the last finger in each protein had a CCHC backbone for the recognition helix. The non-canonical zinc finger-encoding sequences were fused to the nuclease domain of the type IIS restriction enzyme FokI (amino acids 384-579 of the sequence of Wah et al. (1998) Proc. Natl. Acad. Sci. USA 95:10564-10569) via a four amino acid ZC linker and an opaque-2 nuclear localization signal derived from *Zea mays* to form mMDH zinc-finger nucleases (ZFNs). Expression of the fusion proteins in a bicistronic expression construct utilizing a 2A ribosomal stuttering signal as described in Shukla et al. (2009) *Nature* 459:437-441, and was driven by a relatively strong, constitutive and ectopic promoter such as the CsVMV promoter or a promoter derived from the *Solanum lycopersicum* AA6 (AA6) promoter.

The optimal zinc fingers were verified for cleavage activity using a budding yeast based system previously shown to identify active nucleases. See, e.g., U.S. Patent Publication No. 20090111119; Doyon et al. (2008) *Nat Biotechnol.* 26:702-708; Geurts et al. (2009) *Science* 325:433. Zinc fingers for the various functional domains were selected for in-vivo use. Of the numerous ZFNs that were designed, produced and tested to bind to the putative mMDH genomic polynucleotide target sites, four ZFNs were identified as having in vivo activity at high levels, and selected for further experimentation. See, Table 1A. These four ZFNs were characterized as being capable of efficiently binding and cleaving the four unique mMDH genomic polynucleotide target sites in planta.

FIGS. 2A and 2B (SEQ ID NO:2) show the genomic organization of the mMDH locus in relation to the ZFN polynucleotide binding/target sites of the four ZFN pairs. The first ZFN pair (107830L/107830R; referred to respectively as "830L" and "830R" in FIG. 2A) binds within exon 1, the second ZFN pair (107832L/107832R; referred to respectively as "832L" and "832R" in FIG. 2A) binds within exon 3, the third ZFN pair (107833L/107833R; referred to respectively as "833L" and "833R" in FIG. 2A) binds within exon 4, and the fourth ZFN pair (107835L/107835R; referred to respectively as "835L" and "835R" in FIG. 2A) binds within exon 6.

Example 3: Zinc Finger Nuclease Constructs for Expression in Tomato

Plasmid vectors containing ZFN expression constructs of the four exemplary zinc finger nucleases, which were identified using the yeast assay, and described in Example 2, were designed and completed using skills and techniques commonly known in the art. Each zinc finger-encoding sequence was fused to a sequence encoding an opaque-2 nuclear localization signal (Maddaloni et al. (1989) *Nuc. Acids Res.* 17(18):7532), that was positioned upstream of the zinc finger nuclease.

Next, the opaque-2 nuclear localization signal::zinc finger nuclease fusion sequence was paired with the complementary opaque-2 nuclear localization signal::zinc finger nuclease fusion sequence. As such, each construct included a single open reading frame comprised of two opaque-2 nuclear localization signal::zinc finger nuclease fusion sequences separated by the 2A sequence from *Thosea asigna* virus (Mattion et al. (1996) *J. Virol.* 70:8124-8127). Expression of the ZFN coding sequence was driven by the highly expressing constitutive AA6 promoter (U.S. Patent Publication No. 2009/0328248) and flanked by the nos 3' polyA untranslated region (Bevan et al. (1983) *Nucl. Acid Res.* 11:369-385).

The resulting four plasmid constructs, pKG7479 (containing the ZFN 107830L/R construct), pKG7480 (containing the ZFN 107832L/R construct), pKG7481 (containing the ZFN 107833L/R construct) and pKG7482 (containing the ZFN 107835L/R construct) were confirmed via restriction enzyme digestion and via DNA sequencing. See, FIGS. 3 to 6.

Example 4: Large Scale Plasmid Isolation

A large scale plasmid DNA isolation protocol was utilized to produce large quantities of DNA for protoplast transfection using the following protocol. First, 250 mL of LB medium containing 100 µg/mL of carbenicillin was inoculated with a strain of *Escherichia coli* TOP10 (Invitrogen, Carlsbad, Calif.) containing one of the zinc finger nuclease constructs described above in Example 3 at 37° C. overnight. The culture was then centrifuged at 6,000 rpm for 15 minutes and the resulting pellet was resuspended in 20 mL of sterile GTE buffer (per liter: 10 g glucose, 25 mL of 1M tris at pH 8.0, and 20 mL of 0.5M EDTA at pH 8.0) and 20 mg lysozyme (Duchefa, St. Louis, Mo.). Next, 30 mL of NaOH-SDS buffer (200 mM NaOH, 1% SDS (w/v)) was added, mixed thoroughly without vortexing and incubated on ice for 3 minutes. Finally, 22.5 mL of potassium acetate buffer (294.5 g/L) was added and the sample was incubated for 10 minutes on ice. The resulting slurry was centrifuged (6,000 rpm for 25 minutes at 5° C.) and the supernatant was collected after passing it through sterile filter paper.

Next, 60 mL of isopropanol (1 volume) was added to the filtrate supernatant and incubated at room temperature for 10 minutes. The mixture was then centrifuged (6,000 rpm for 30 minutes at room temperature), the supernatant discarded and the pellet washed in 70% ethanol. After a second round of centrifugation (6,000 rpm for 5 minutes at room temperature) the supernatant was removed and the pellet was dissolved in 4 mL of TE (10 mM Tris, 1 mM EDTA at pH 8.0), 4 µl of RNase solution was added and the solution was incubated for 20 minutes at room temperature. The samples were then transferred to a 12 mL tube and 400 µl of 3M NaOAc at pH 5.2, and 4 mL phenol was added, vortexed, and then centrifuged (4,000 rpm for 10 minutes at room temperature). The upper phase of the centrifuged sample was collected in a new tube and 4 mL of chloroform/isoamyl alcohol (24:1) was added, vortexed and centrifuged (4,000 rpm for 10 minutes at room temperature). Again, the upper phase of the centrifuged sample was collected, and 8 mL of absolute ethanol was added and incubated for 30 minutes at −20° C.

After a further round of centrifugation, (4,000 rpm for 30 minutes at 5° C.) the pellet was rinsed with 70% ethanol and centrifuged (4,000 rpm for 5 minutes at room temperature) and then air dried in a flow cabinet. The pellet was dissolved in 4 mL of MILLI-Q™ purified water and aliquoted into 1.5 mL eppendorf tubes. Next, 0.5 mL of a PEG solution (40% polyethylene glycol 6,000 (w/v), MgCl2:6H2O, filter (0.2 µm)) was added and after a 30 minute incubation at room temperature, the tubes were centrifuged (14,000 rpm for 10 minutes). The pellet was washed with 70% ethanol and then centrifuged (14,000 rpm for 5 minutes); this step was repeated twice. The supernatant was discarded and the pellet was dissolved in a final volume of 0.5 mL of MILLI-Q™ water. The plasmid DNA concentration was determined using a NANO DROP™ apparatus (Thermo Scientific, Wilmington, Del.).

Example 5: Tomato Protoplast Isolation and Transfection

Isolation and regeneration of tomato leaf protoplasts has been previously described (Shahin (1985) *Theor. Appl. Genet.* 69:235-240; Tan et al. (1987) *Theor. Appl. Genet.* 75:105-108; Tan et al. (1987) *Plant Cell Rep.* 6:172-175) and exemplary solutions and medium that can be utilized for this protocol are found in these publications. Briefly, *Solanum lycopersicum* seeds were sterilized with 0.1% sodium-hypochlorite and grown in vitro on sterile MS20 medium with a photoperiod of 16/8 hours at 2,000 lux at 25° C. and 50-70% relative humidity. Next, 1 g of freshly harvested leaves was placed in a dish with 5 mL of CPW9M liquid medium. Using a scalpel blade the harvested leaves were cut perpendicular to the main stem. Sections of leaf were ~1 mm in width.

The leaf sections were transferred to a fresh plate containing 25 mL enzyme solution (CPW9M containing 2% cellulose ONOZUKA RS™, 0.4% macerozyme ONOZUKA R10™, 2,4-D (2 mg/mL), NAA (2 mg/mL), BAP (2 mg/mL) at pH5.8) and digestion proceeded overnight at 25° C. in the dark. The protoplasts were then freed by placing them on an orbital shaker (40-50 rpm) for 1 hour. Protoplasts were separated from cellular debris by passing them through a 50 µm sieve, and washing the sieve twice with CPW9M. Next, the protoplasts were centrifuged at 85 times gravity (×g), the supernatant discarded, and the pellet was taken up in half the volume of CPW9M solution.

Finally, the protoplasts were taken up in 3 mL of CPW9M solution, and 3 ml of CPW18S was then added carefully so that a layered interface was created and there was no mixing between the two solutions. The protoplasts were spun at 85 times gravity for 10 minutes and the viable protoplasts floating at the interphase layer were collected using a long Pasteur pipette. The protoplast volume was increased to 10 mL by adding more CPW9M medium and the number of recovered protoplasts was determined in a haemocytometer. The protoplast suspension was centrifuged at 85 times gravity for 10 minutes at 5° C. The supernatant was discarded and the protoplast pellet was resuspended to a final concentration of 106. mL-1 in CPW9M wash medium.

Transfection of the isolated protoplasts with ZFN constructs was then performed. In a 10 mL tube, 250 µL of protoplast suspension, and plasmid DNA (used at concentrations of 20 µg or 30 µg), and 250 µl of PEG solution (40% PEG4000, 0.1M Ca(NO3)2, 0.4M mannitol) were gently, but thoroughly mixed. After 20 minutes of incubation at room temperature, 5 mL of cold 0.275 M Ca(NO3)2 was added dropwise. The protoplast suspension was centrifuged for 10 minutes at 85 times gravity at 4° C. After the centrifugation, the supernatant was discarded and the protoplasts were resuspended in 4 mL of liquid K8p medium. The protoplasts were incubated for 48 hours at 28° C. in the dark and then harvested by centrifugation for genomic DNA isolation.

The activity of the ZFNs in tomato cell protoplasts was tested by transfecting the tomato protoplasts using the above described protocol. The tomato protoplasts were isolated in large numbers and plasmid DNA was introduced into the cell of the protoplast using the PEG mediated transfection protocol. Typically, when using reporter constructs, such as a reporter construct which contains the green fluorescent protein (GFP) gene, transfection rates of up to 80% are observed. The large numbers of plasmid copies introduced into the tomato cells produce a large amount of the protein encoded by the plasmid. Resultantly, tomato cell expressed GFP protein is detectable up to 48 hours after transfection. However, the expression of the introduced construct is transient as within 48 hours the plasmid DNA in the cell is eliminated.

Example 6: ZFN Activity in Tomato Protoplasts

To measure the expression of the ZFN constructs in tomato protoplasts and the activity of the ZFNs to cleave the mMDH locus of the tomato genomic DNA, a footprint analysis was completed as follows. Tomato protoplasts were isolated and transfected with plasmid DNA carrying one of the four exemplary ZFN constructs; pKG7479 (containing the ZFN 107830L/R construct); pKG7480 (containing the ZFN 107832L/R construct); pKG7481 (containing the ZFN 107833L/R construct); or pKG7482 (containing the ZFN 107835L/R construct). After being introduced inside the cell, the ZFN was expressed and the ZFN enzyme induced DNA double strand breaks (DSB) at the specific mMDH target site. The DNA DSB was repaired by proteins involved in the non-homologous end joining (NHEJ) pathway, this repair process is sometimes error prone and results in small insertions or deletions ("indels") at the DSB induction site. After ZFN treatment the mMDH target sites were PCR amplified and the resulting indels were detected and quantified using high resolution melting (HRM) curve analysis and/or sequencing.

Protoplasts (~250,000) from the tomato M82 variety were isolated and transfected with varying concentrations (20 or 30 µg) of the pKG7479, pKG7480, pKG7481 and pKG7482 plasmids and the cells were collected after 48 hours. As a negative control, a tomato protoplast transfection was performed using a plasmid containing the AA6::GFP construct. Genomic DNA was then isolated from each sample using the DNEASY MINI KIT™ (Qiagen, Valencia, Calif.) and the DNA concentration determined. The relevant target sites, which correspond with the introduced ZFN construct, were amplified using the HERCULASE II FUSION KIT™ per manufacturer's instructions (Agilent Technologies, Santa Clara, Calif.) from each transfected protoplast sample. All of the target sites were amplified from the negative control sample that had been transfected with the GFP control construct using the HERCULASE II FUSION KIT™ per manufacturer's instructions. The primers used for the PCR amplifications are described in Tables 2A (PCR analysis) and 2B (HRM analysis).

TABLE 2A

Target site specific primers for the PCR analysis

| amplifies target site in: | Primer Sequence | fragment size |
|---|---|---|
| Exon 1 | 08G384 ACCACAACTCCTAATTTATTTTCTCCG (SEQ ID NO: 57)<br>10A493 AAGGCTGGATACTAAAGGGT (SEQ ID NO: 58) | 312 bps |
| Exon 3 | 10Q441 TAAGTACTGCCCCAATGTGAG (SEQ ID NO: 59)<br>10Q442 TTGGGTTCGCTTTGTGAGT (SEQ ID NO: 60) | 714 bps |
| Exon 4 | 10Q441 TAAGTACTGCCCCAATGTGAG (SEQ ID NO: 59)<br>10Q442 TTGGGTTCGCTTTGTGAGT (SEQ ID NO: 60) | 714 bps |
| Exon 6 | 10R044 ATACTGCCCCAAACCACT (SEQ ID NO: 63)<br>10R045 ACTATCCCTCAACACATCCAGAA (SEQ ID NO: 64) | 391 bps |

TABLE 2B

Primers used for the HRM analysis

| Target site | HRM Primer Sequence |
|---|---|
| Exon 1 | 10Q445 CGTAGCTTTTACCTTTTCCTC (SEQ ID NO: 65)<br>10Q446 ATAAAGGCTGTCCAATCCC (SEQ ID NO: 66) |
| Exon 3 | 10Q443 CAATATGATAAGCAACCCAG (SEQ ID NO: 67)<br>10Q444 TTAGACAAGAAGACGCGCA (SEQ ID NO: 68) |
| Exon 4 | 10Q451 GCGTCTTCTTGTCTAATTC (SEQ ID NO: 69)<br>10Q452 CTTGAGAAAATAATGGGAGG (SEQ ID NO: 70) |
| Exon 6 | 10Q459 CGGTTCTAAGCAGTTAGTTT (SEQ ID NO: 71)<br>10Q460 TGACGTCCAGTGTCTTTGT (SEQ ID NO: 72) |

The PCR amplified products were purified using the PCR PURIFICATION KIT™ (Qiagen) and 50 ng of purified DNA was used for cloning into the ZERO BLUNT CLONING KIT™ (Invitrogen) as per the manufacturer's instructions. Next, 2 μl of the ligation mix was transformed into Escherichia coli ONE-SHOT TOP10 competent cells (Invitrogen) and colonies were selected on LB medium supplemented with 100 μg/mL of kanamycin. A HERCULASE II FUSION KIT™ PCR reaction (50 μl final volume) was performed per the manufacturer's directions using the HRM primers described in Table 2. Each set or PCR primers amplified a fragment of approximately 200 bps. The resulting PCR products were used for the HRM analysis.

Completion of the HRM analysis was performed using art recognized procedures. Briefly, the PCR products were mixed at a 1:1 ratio with a wild type PCR product generated using the same primers on untreated (no ZFNs) genomic DNA. SYBR®-Green dye was added and a melting curve profile of the PCR products was measured in a ROCHE LIGHT CYCLER™ (Roche Diagnostics, Indianapolis, Ind.). PCR products with melting curves that were significantly different from the wild type untreated PCR product were identified and saved. A PCR reaction using M13F and M13R primers was then completed directly on the bacterial clones which were identified using the HRM procedure, and the resulting PCR product was purified and sequenced. The results of this analysis are shown in Table 3 and FIG. 7.

TABLE 3

Summary of the HRM and sequence analysis

| Construct Number | ZFN Number | Total clones analyzed | INDEL clones | % INDEL clones |
|---|---|---|---|---|
| pKG7479 | 107830 | 288 | 12 | 4.1 |
| pKG7480 | 107832 | 288 | 16 | 5.5 |
| pKG7481 | 107833 | 288 | 6 | 2.0 |
| pKG7482 | 107835 | 288 | 2 | 0.7 |

As shown, the formation of indels was detected at all of the ZFN target sites, demonstrating that all four ZFNs are active in tomato protoplasts. An estimation of the efficiency of a given ZFN construct can be made by calculating the number of PCR products produced by a treatment that contain indels. The ZFNs 107830 and 107832 gave the highest number of indel PCR products (4.1% and 5.5%, respectively). Whereas, for ZFNs 107833 and 107835 the number of indel PCR products was significantly lower (2% and 0.7%, respectively). There was no detection of any indels in the PCR products derived from the control tomato protoplasts treated with the GFP plasmid.

Example 7: Isolation of Plants Containing Mutations at the mMDH Locus

Tomato protoplasts were isolated from the tomato varieties, M82 and Moneymaker, and transfections with pKG7479, pKG7480, pKG7481 and pKG7482 were performed as described previously. For regeneration of tomato plants from the transfection the protoplasts were finally resuspended in 2 mL of alginate solution (mannitol 90 g/L, CaCl2.2H2O 140 mg/L, alginate-Na 20 g/L (Sigma-Aldrich, St. Louis, Mo.)) and were mixed thoroughly by inversion. From this resuspension, 1 mL of the cells were layered evenly on a Ca-agar plate (72.5 g/L mannitol, 7.35 g/L CaCl2.2H2O, 8 g/L agar) and allowed to polymerize. The alginate discs were then transferred to 4 cm Petri dishes containing 4 mL of K8p culture medium and grown at 28° C. in the dark for 7 days. After the allotted incubation time, the alginate discs were sliced into thin strips and placed on plates containing GM-ZG medium for 3 weeks at 28° C. in the dark to promote callus development. After this period of incubation, individual calli were then picked from the strips and arrayed on fresh GM-ZG medium and grown at 25° C. in the light. After 3 weeks the calli were transferred to fresh GM-ZG medium. This step was repeated twice until the calli had reached approximately 2 cm in size.

Next, the calli were transferred to medium to promote shoot formation (MS20-ZI; MS20+2 mg/L zeatin+0.1 mg/L IAA) and the transfer was repeated until shoots formed. One leaf from each shoot was then removed for DNA isolation and the relevant mMDH target sites were amplified using the primers described in Table 2 and the PCR reactions previously described. The PCR products were then purified and sequenced to identify shoots that contained mutations in the mMDH locus. These shoots were transferred to rooting medium (MS20+0.5 mg/1 IBA) and finally to the greenhouse.

A summary of the mutations which were produced in the genome of the tomato plants for these experiments is shown in Table 4. The ZFN binding sites are underlined and the deleted nucleotides (−) are indicated. The plant identification numbers marked with an asterisk indicate plants that had identical mutations in both copies of mMDH and were determined to be homozygous for the described mutations.

TABLE 4

Summary of ZFN-induced mutations in mMDH

| Plant | Fertile | Mutation | SEQ ID NO: | mMDH sequence |
|---|---|---|---|---|
| 107830 16-6 | − | −6 | − | (Deletion upstream ZFN binding site) |
| 107830 13-4 | − | −6 | 99 | AGCATCCTATGTATCT------<br>GGATTCGCATCGGGATCCG |
| 107830 60-7 | + | −2 | 100 | AGCATCCTATGTATCTCGCC--<br>GGATTCGCATCGGGATCCG |
| 107830 86-4 | − | −4 | 101 | AGCATCCTATGTATCT----<br>GTGGATTCGCATCGGGATCCG |
| 107830 60-3 | − | −8 | 102 | AGCATCCTATGTA--------<br>TGGATTCGCATCGGGATCCG |

TABLE 4-continued

Summary of ZFN-induced mutations in mMDH

| Plant | Fertile | Mutation | SEQ ID NO: | mMDH sequence |
|---|---|---|---|---|
| 107832 12-6 | + | +2 | 103 | CTCTTTGGAGTTACCATGCTCTTGATGTGGTTAGGGCCAAG |
| 107832 76-5 | + | -9 | 104 | CTCTTTGGAGTT---------GATGTGGTTAGGGCCAAG |
| 107832 8-3 | + | -9 | 105 | CTCTTTGGAGTTACCA---------TGTGGTTAGGGCCAAG |
| 107832 3-8 | + | -3 | 106 | CTCTTTGGAGTTACCAT---TGATGTGGTTAGGGCCAAG |
| 107832 34-3* | + | -3 | 107 | CTCTTTGGAGTTACCAT---TGATGTGGTTAGGGCCAAG |
| 107832 3-6 | - | -3 | 108 | CTCTTTGGAGTTACCAT---TGATGTGGTTAGGGCCAAG |
| 107832 17-5 | + | -4 | 109 | CTCTTTGGAGTTACCATGCT----GTGGTTAGGGCCAAG |
| 107832 9-6 | + | -3 | 110 | CTCTTTGGAGTTACCAT---TGATGTGGTTAGGGCCAAG |
| 107832 76-6 | + | -4 | 111 | CTCTTTGGAGTTACCA----TGATGTGGTTAGGGCCAAG |
| 107832 16-3 | - | -4 | 112 | CTCTTTGGAGTTACCA----TGATGTGGTTAGGGCCAAG |
| 107832 28-1 | + | -4 | 113 | CTCTTTGGAGTTACC----TTGATGTGGTTAGGGCCAAG |
| 107832 53-1 | + | -5 | 114 | CTCTTTGGAGTTACCATG------ATGTGGTTAGGGCCAAG |
| 107832 10-8 | - | -1 | 115 | CTCTTTGGAGTTACCAT-CTTGATGTGGTTAGGGCCAAG |
| 107832 2-7* | - | -4 | 116 | CTCTTTGGAGTTACCATG----ATGTGGTTAGGGCCAAG |
| 107832 10-2 | + | -2 | 117 | CTCTTTGGAGTTACCATGC--GATGTGGTTAGGGCCAAG |
| 107832 44-3 | - | -4 | 118 | CTCTTTGGAGTTACCATGCT----GTGGTTAGGGCCAAG |
| 107832 32-3 | + | -4 | 119 | CTCTTTGGAGTTAC----CTTGATGTGGTTAGGGCCAAG |
| 107832 9-8 | + | -3 | 120 | CTCTTTGGAGTTACCAT---TGATGTGGTTAGGGCCAAG |
| 107832 9-7 | + | -3 | 121 | CTCTTTGGAGTTACCA---TTGATGTGGTTAGGGCCAAG |
| 107835 20-5 | + | -22 | 122 | CACCGAGCTTCCCTT---------------------- |
| 107835 33-1 | + | -7 | 123 | CACCGAGCTTCCCTTC-------CCAAGGTAATAAGCC |

The mutant plant lines that were fertile were then crossed to the parent plants and the F1 seed was collected. The F1 seedlings were screened to detect the indel mutation that was present in the parent mutant plant and these plants were grown to maturity and self-fertilized to produce F2 seed. The tomato plants which are grown from the F2 seed can be used to determine the effects of the mutations on tomato yield.

Example 8: Molecular and Biochemical Confirmation of Mutations at the mMDH Locus F2 seed from each mutant plant line was germinated and 12 seedlings were genotyped by amplifying the mutation site and sequencing the PCR products to determine whether the seedling possessed the wild type sequence, or was either heterozygous or homozygous for the indel mutation. Two seedlings of each type (6 in total) were then allowed to grow to maturity and set fruit. Tissues samples were collected from each plant and the effects of the various mutations on mMDH protein levels and mMDH activity were measured. mMDH protein levels were measured semi-quantitatively using Western blotting, and the mMDH activity was measured by determining the tomato plant fruit yield.

To determine the mMDH protein levels, a polyclonal anti-mMDH antibody produced through inoculation of rabbits with an mMDH epitope (RSEVAGFAGEEQLGQA, SEQ ID NO:62) and tested using recombinant mMDH protein overexpressed in E. coli was used for detection of the plant derived proteins. mMDH was detected in leaf samples obtained from transgenic and control plants. Plant extracts from transgenic and control plants were assayed with mMDH protein standards which were incubated with NUPAGE® LDS sample buffer (Invitrogen, Carlsbad, Calif.) containing DTT at 90° C. for 10 minutes and electrophoretically separated in an acrylamide precast gel with MES running buffer (Invitrogen). Proteins were then electro-transferred onto nitrocellulose membrane using the Invitrogen manufacturer's protocol. After blocking with the Superblock® Blocking Mix (Invitrogen) and washing with 0.1% PBST, the mMDH protein was detected by anti-mMDH antiserum followed by goat anti-rabbit phosphatase. The detected protein was visualized via chemiluminescence using the SuperSignal West Pico Luminol Enhancer™ and Stable Peroxide Solution™ mixed at equal volumes (Pierce, Rockford, Ill.).

A Western blot assay was completed on the F2 mutant plant families to detect the presence and determine the molecular weight of the mMDH protein. The full length mMDH protein could be detected in F2 control plants lacking an indel mutation, and F2 plants heterozyogous for the indel mutations. However, no signal for the mMDH protein could be detected in F2 plants that were homozygous for an indel mutation which disrupted the mMDH open reading frame. The F2 plants which contained a homozygous indel produced a truncated mMDH protein sequence. The mMDH protein sequence was truncated by introducing premature stop codons or shortening the mMDH protein. The truncated mMDH proteins were expected to be present on the Western blot as a band with a lower molecular weight. However, no such smaller bands were detected. These results suggest that the truncated proteins were degraded in the cell. F2 mutant plants, 107832_8-3 and 107832_9-6, that contained homozygous indel mutations which resulted in a deletion or alteration of one, two or more amino acids (i.e., the mMDH protein was not truncated) within the conserved NAD binding domain produced a full length mMDH protein as indicated via the Western blot assay.

Figure 8A:
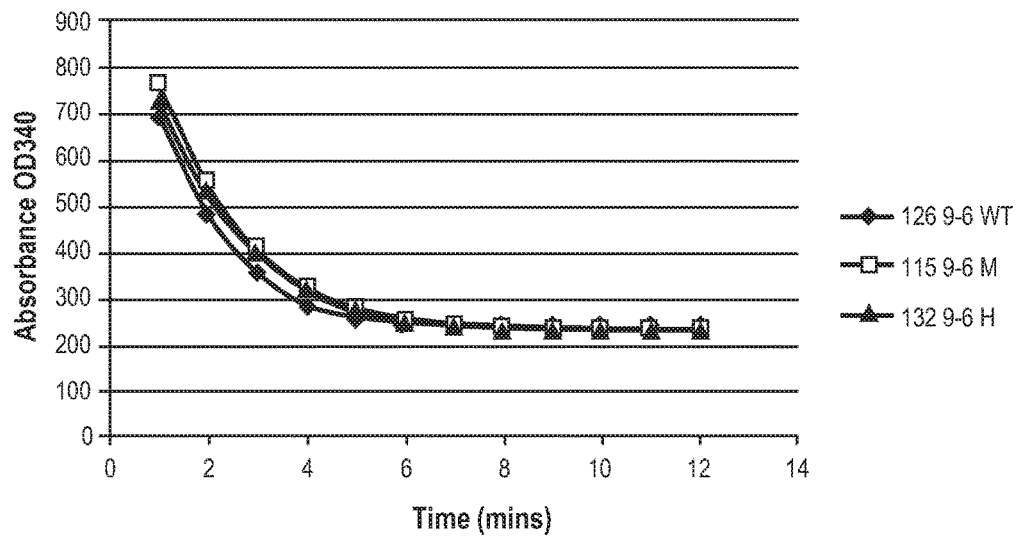
FIGS. 8A and 8B are graphs showing mMDH activity in F2 plants.
Figure 8B:
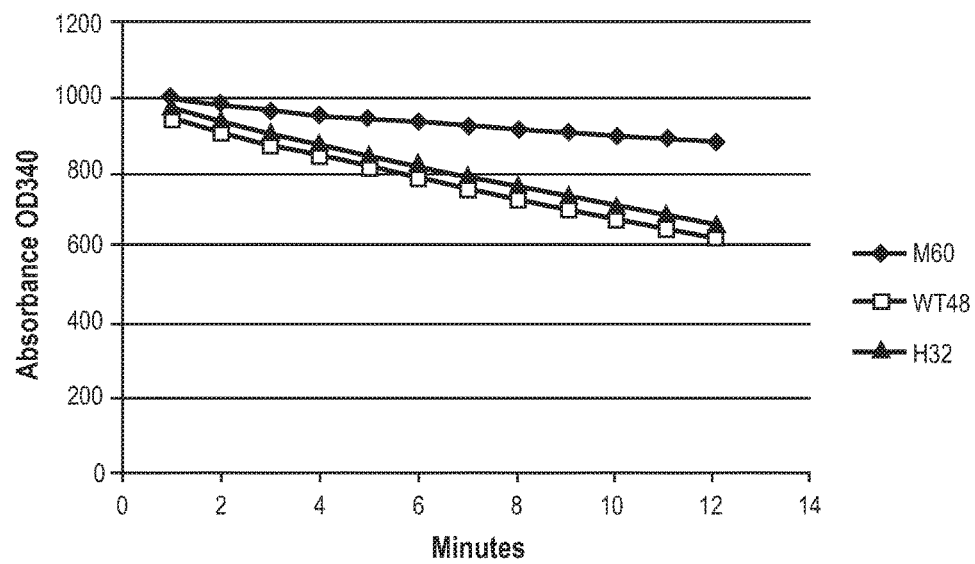

A biochemical assay was completed to measure the mMDH activity in the F2 plants. The mMDH protein catalyzes the conversion of malate and NAD+ into oxaloacetate and NADH and vice versa. The converted NADH exhibits an absorbance maxima at O.D. 340 nm, whereas at this wavelength NAD+ has negligible absorbance. Hence, the mMDH activity of a sample can be measured by following the conversion rate of NADH to NAD+ in the presence of oxaloacetate. Five leaf punches of about 2 cm in diameter were taken from young leaves of individual F2 plants and crushed in extraction buffer (50 mM imidazole-HCl buffer containing 10 mM dithiothreitol, 20 mM $MgCl_2$ and 2 mM EDTA) at 4° C. The leaf extract was centrifuged at 10,000 g for 20 minutes in a refrigerated centrifuge; the supernatant was decanted and placed on ice until the enzyme preparation was utilized in the assay. For the assay, 1.5 ml of assay buffer (50 mM Tris-HCl pH8.0, 1 mM EDTA) was pipetted into a tube, 100 µl of the enzyme extract was added and incubated at 37° C. in a water bath for 5 minutes. The cocktail was poured into a quartz cuvette and 50 µl of NADH was added (6 mM NADH in Tris-HCl, pH 8.0) and placed in a spectrophotometer set at 340 nm. The initial reading and the following decrease in absorbance was recorded at 15 second intervals up to 3 minutes and these readings served as the control. Next, 50 µl of oxaloacetate was added (0.3M oxaloacetate freshly prepared in distilled water) and the absorbance was recorded for 3 minutes. The mMDH activity in F2 lines segregating for both in frame and null indel mutations are shown in FIG. 8.

The F2 plants derived from line 107832_9-6 that segregated for the indel mutation (−3 bps) produced a full length mMDH protein on the Western blot. In the biochemical assay the mMDH activity was similar in all plants tested. The results of the biochemical assay followed the same trend for all plants tested. The tested plants included null, heterozygous, and homozygous plants which contained the indel mutation and which produced an mMDH protein lacking a single amino acid. Therefore, the loss of the amino acid did not negatively impact mMDH activity in the biochemical assay. Nevertheless, the biochemical efficiency may still be slightly compromised as the biochemical assay may not be sensitive enough to detect a moderate decrease in mMDH activity. F2 plants derived from line 107832_10-2 and segregating for the indel mutation (−2 bps) were also tested using the biochemical assay. The plants that were null and heterozygous for this indel mutation resulted in similar levels of mMDH activity. The plants that were homozygous for the indel mutation showed significantly reduced mMDH activity. The Western blot for the mMDH protein was not detected in these plants.

Example 9: Effect of Mutations at the mMDH Locus on Tomato Fruit Yield

To determine the effect of the previously described mutations on tomato fruit yield, all the fruits of the first tomato truss were harvested and the number of tomatoes and the fresh weight of each tomato was determined using the method described in Centeno et al. (2011) *Plant Cell* 23:162-184.

Figure 9:
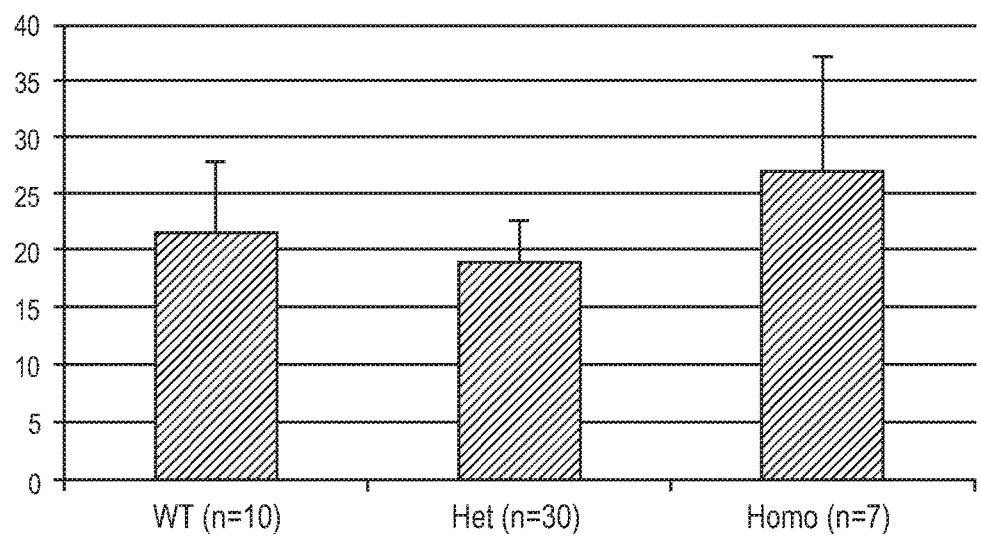
FIG. 9 is a graph depicting tomato fruit yield of line 107832 9-6. The average tomato weight (g) is shown on the Y axis for the 3 classes of F2 plants segregating for the −3 bps mutation in the mMDH locus. "WT" indicates the F2 plants lacking the indel, "Het" indicates the F2 plants heterozygous for the indel, and "Homo" indicates the F2 plants homozygous for the indel.

In F2 plants derived from the indel mutant 107832_9-6 (−3 bps) the average fresh weight of each tomato obtained and the total fresh weigh of all tomatoes harvested from the first truss of the mutant plants (heterozygous or homozygous) was measured. The fresh weights of tomatoes obtained from the homozygous 107832_9-6 tomato plants were greater than the fresh weights of tomatoes obtained from the control plants (which do not contain the mutation). See, FIG. 9. The mutations which were produced at the mMDH locus in the 107832_9-6 tomato plants resulted in reduced protein activity that increased fruit yield. In contrast, tomato plants that were heterozygous for any indel mutation that led to disruption of the mMDH open reading frame showed reduced growth and a lower total fruit yield. Therefore, a decrease in mMDH activity which was measured in plants homozygous for the indel mutation resulting in an increase in total tomato fruit yield.

Example 10: Effect of Mutations at the mMDH Locus on Enzyme Rates and Activity

The mutations to the mMDH enzyme in the tomato genome which resulted from ZFN cleavage as previously described are introduced into isolated polynucleotide sequences which encode the native mMDH enzymes from tomato (SEQ ID NO:1), soybean (SEQ ID NO:125), and corn (SEQ ID NO:126).

Figures 11, 12:
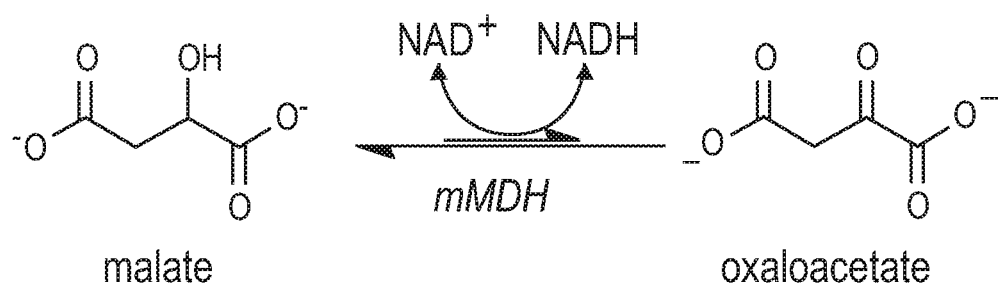
FIG. 11 is a sequence alignment of mMDH mutations occurring in the tomato genome.
FIG. 12 is a schematic showing the biochemical reaction catalyzed by the mMDH enzyme.

An alignment of the native versions of these enzymes is shown in FIG. 10, which illustrates mMDH enzymes from different plant species share high levels of sequence similarity and conserved protein motifs. The mutations which resulted in the tomato mMDH enzyme from ZFN cleavage are illustrated in FIG. 11, these peptide sequences correspond with the cleaved DNA sequences shown in Table 4.

Further included as an embodiment of this disclosure are novel mutations which are incorporated throughout the isolated polynucleotide sequence which encodes the mMDH enzymes. Both the first and second NADH binding sites contain the majority of the introduced mutations. Exemplary mutations (e.g., deletions and/or insertions) of one or more amino acids, numbered relative to the wild-type (native) sequences include, but are not limited to mutations at one or more amino acid residues: 104-136, numbered and aligned relative to the tomato MDH sequence shown in SEQ ID NO:1 (V, V, I, I, P, A, G, V, P, R, K, P, G, M, T, R, D, D, L, F, N, I, N, A, G, I, V, K, S, L, C, T, A) and/or amino acid residues 171-220, numbered relative to the tomato MDH sequence shown in SEQ ID NO:1 (D, E, K, K, L, F, G, V, T, M, L, D, V, V, R, A, K, T, F, Y, A, G, K, A, K, V, N, V, A, E, V, N, L, P, V, V, G, G, H, A, G, I, T, I, L, P, L, F, S, Q); one or more mutations at amino acid residues 104-136 (V, V, I, I, P, A, G, V, P, R, K, P, G, M, T, R, D, D, L, F, N, I, N, A, G, I, V, K N, L, S, T, A) and/or amino acid residues 171-220 (D, E, K, K, L, F, G, V, T, T, L, D, V, V, R, A, K, T, F, Y, A, G, K, A, N, L, P, V, T, D, V, N, V, P, V, V, G, G, H, A, G, I, T, I, L, P, L, F, S, Q), numbered relative to the corn MDH sequence shown in SEQ ID NO:126 and aligned to SEQ ID NO:1; and mutations at one or more amino acid residues 104-136 (V, V, I, I, P, A, G, V, P, R, K, P, G, M, T, R, D, D, L, F, N, I, N, A, G, I, V, E, T, L, C, T, A) and/or amino acid residues 171-220 (D, E, K, R, L, F, G, V, T, T, L, D, V, V, R, A, K, T, F, Y, A, G, K, A, N, V, P, V, A, G, V, N, V, P, V, V, G, G, H, A, G, I, T, I, L, P, L, F, S, Q), numbered relative to the soybean MDH sequence shown in SEQ ID NO:125 and aligned to SEQ ID NO:1.

Polynucleotide sequences encoding such mutations in MDH are shown below (SEQ ID NO:132-137 and SEQ ID NO:124):

```
Corn mMDH mutation #1 (3 nucleotide deletion)
(SEQ ID NO: 132)
ATGAAGGCCGTCGCTGATGAGATCCACCTCCCAGCTCCTCCGCCGCCGGA

GCTACTCCTCCGCATCCGGGCAGCCCGAGCGGAAGGTGGCCATCCTCGGG

GCGGCGGGGGGCATCGGGCAGCCGCTGTCGCTGCTCATGAAGCTTAACCC

ACTCGTCTCCTCCCTCTCGCTCTACGATATCGCCGGCACCCCAGGTGTCG

CGGCCGACGTCTCCCACATCAACTCCCCCGCCCTGGTGAAGGGTTTCATG

GGTGATGAGCAGCTTGGGGAAGCGCTAGAGGGCTCGGACGTGGTGATCAT

ACCGGCCGGCGTCCCGAGGAAGCCCGGCATGACCAGGGACGACCTATTCA

ATATCAACGCTGGCATCGTTAAGAACCTCAGCACCGCCATCGCCAAGTAC

TGCCCCAATGCCCTTGTCAACATGATCAGCAACCCTGTGAACTCAACTGT

ACCGATTGCTGCTGAGGTTTTCAAGAAGGCTGGGACATATGATGAGAAGA

AGTTGTTTGGCGTGACCACTGATGTTGTTCGTGCTAAGACTTTCTATGCT
```

```
GGGAAGGCTAATTTACCAGTTACCGATGTGAATGTCCCTGTTGTTGGTGG

TCATGCGGGTATCACTATCCTGCCGTTGTTCTCACAGGCCACCCCTGCAA

CCAACGCATTGTCTGATGAAGACATCAAGGCTCTCACCAAGAGGACACAG

GATGGTGGAACTGAAGTTGTCGAGGCAAAGGCTGGGAAGGGCTCTGCAAC

CTTGTCCATGGCGTATGCTGGTGCTGTTTTTGCAGATGCATGCTTGAAGG

GTCTCAATGGAGTTCCGGATATTGTTGAGTGCTCTTTTGTTCAATCAACT

GTAACAGAGCTTCCATTCTTTGCATCTAAGGTAAGGCTTGGGAAGAATGG

AGTTGAGGAAGTGCTTGGATTAGGTGAGCTGTCGGACTTTGAGAAAGAAG

GGTTGGAGAAGCTCAAGAGCGAGCTCAAGTCTTCGATTGAGAAGGGTATC

AAGTTTGCAAATGATAACTAG

Corn mMDH mutation #2 (9 nucleotide deletion)
(SEQ ID NO: 133)
ATGAAGGCCGTCGCTGATGAGATCCACCTCCCAGCTCCTCCGCCGCCGGA

GCTACTCCTCCGCATCCGGGCAGCCCGAGCGGAAGGTGGCCATCCTCGGG

GCGGCGGGGGGCATCGGGCAGCCGCTGTCGCTGCTCATGAAGCTTAACCC

ACTCGTCTCCTCCCTCTCGCTCTACGATATCGCCGGCACCCCAGGTGTCG

CGGCCGACGTCTCCCACATCAACTCCCCCGCCCTGGTGAAGGGTTTCATG

GGTGATGAGCAGCTTGGGGAAGCGCTAGAGGGCTCGGACGTGGTGATCAT

ACCGGCCGGCGTCCCGAGGAAGCCCGGCATGACCAGGGACGACCTATTCA

ATATCAACGCTGGCATCGTTAAGAACCTCAGCACCGCCATCGCCAAGTAC

TGCCCCAATGCCCTTGTCAACATGATCAGCAACCCTGTGAACTCAACTGT

ACCGATTGCTGCTGAGGTTTTCAAGAAGGCTGGGACATATGATGAGAAGA

AGTTGTTTGGCGTGACCATTGTTCGTGCTAAGACTTTCTATGCTGGGAAG

GCTAATTTACCAGTTACCGATGTGAATGTCCCTGTTGTTGGTGGTCATGC

GGGTATCACTATCCTGCCGTTGTTCTCACAGGCCACCCCTGCAACCAACG

CATTGTCTGATGAAGACATCAAGGCTCTCACCAAGAGGACACAGGATGGT

GGAACTGAAGTTGTCGAGGCAAAGGCTGGGAAGGGCTCTGCAACCTTGTC

CATGGCGTATGCTGGTGCTGTTTTTGCAGATGCATGCTTGAAGGGTCTCA

ATGGAGTTCCGGATATTGTTGAGTGCTCTTTTGTTCAATCAACTGTAACA

GAGCTTCCATTCTTTGCATCTAAGGTAAGGCTTGGGAAGAATGGAGTTGA

GGAAGTGCTTGGATTAGGTGAGCTGTCGGACTTTGAGAAAGAAGGGTTGG

AGAAGCTCAAGAGCGAGCTCAAGTCTTCGATTGAGAAGGGTATCAAGTTT

GCAAATGATAACTAG

Soybean mMDH mutation #1 (3 nucleotide deletion)
(SEQ ID NO: 134)
ATGAAGCCATCGATGCTCAGATCTCTTCACTCTGCCGCCACCCGCGGCGC

CTCCCACCTCTCCCGCCGTGGCTACGCCTCCGAGCCGGTGCCGGAGCGCA

AGGTGGCCGTTCTAGGTGCCGCCGGCGGGATCGGGCAACCCCTCTCCCTT

CTCATGAAGCTCAACCCCCTCGTTTCCAGCCTCTCCCTCTACGATATCGC

CGGAACTCCCGGTGTCGCCGCCGATGTCAGCCACATCAACACCGGATCTG

AGGTAGTGGGGTACCAAGGTGACGAAGAGCTCGGAAAAGCTTTGGAGGGT

GCAGATGTTGTTATAATTCCTGCTGGTGTGCCCAGAAAGCCTGGAATGAC
```

```
TCGTGATGATCTTTTTAACATCAATGCTGGCATTGTTGAGACACTGTGTA
CTGCTATTGCTAAGTACTGCCCTCATGCCCTTGTTAACATGATAAGCAAT
CCTGTGAACTCCACTGTTCCTATTGCTGCTGAAGTTTTCAAGAAGGCAGG
AACGTATGATGAGAAGAGATTGTTTGGTGTTACCACTGATGTTGTTAGGG
CAAAAACTTTCTATGCTGGGAAAGCCAATGTTCCAGTTGCTGGTGTTAAT
GTACCTGTTGTGGGTGGCCATGCAGGCATTACTATTCTGCCATTATTTTC
TCAAGCCACACCAAAAGCCAATCTTGATGATGATGTCATTAAGGCTCTTA
CAAAGAGGACACAAGATGGAGGAACAGAAGTTGTAGAAGCTAAGGCTGGA
AAGGGTTCTGCAACTTTGTCAATGGCCTATGCTGGTGCCCTATTTGCTGA
TGCTTGCCTTAAGGGCCTCAATGGAGTCCCAGATGTTGTGGAGTGCTCAT
TCGTGCAATCCACTGTTACTGAACTTCCCTACTTTGCTTCCAAGGTGAGG
CTTGGGAAGAATGGAGTGGAGGAAGTTCTGGGCTTAGGACCTCTCTCAGA
TTTTGAGCAACAAGGCCTCGAAAGCCTTAAGCCTGAACTCAAATCATCAA
TTGAGAAGGGAATCAAATTTGCCAACCAGTAA
```

Soybean mMDH mutation #2 (9 nucleotide deletion) (SEQ ID NO: 135)
```
ATGAAGCCATCGATGCTCAGATCTCTTCACTCTGCCGCCACCCGCGGCGC
CTCCCACCTCTCCCGCCGTGGCTACGCCTCCGAGCCGGTGCCGGAGCGCA
AGGTGGCCGTTCTAGGTGCCGCCGGCGGGATCGGGCAACCCCTCTCCCTT
CTCATGAAGCTCAACCCCCTCGTTTCCAGCCTCTCCCTCTACGATATCGC
CGGAACTCCCGGTGTCGCCGCCGATGTCAGCCACATCAACACCGGATCTG
AGGTAGTGGGGTACCAAGGTGACGAAGAGCTCGGAAAAGCTTTGGAGGGT
GCAGATGTTGTTATAATTCCTGCTGGTGTGCCCAGAAAGCCTGGAATGAC
TCGTGATGATCTTTTTAACATCAATGCTGGCATTGTTGAGACACTGTGTA
CTGCTATTGCTAAGTACTGCCCTCATGCCCTTGTTAACATGATAAGCAAT
CCTGTGAACTCCACTGTTCCTATTGCTGCTGAAGTTTTCAAGAAGGCAGG
AACGTATGATGAGAAGAGATTGTTTGGTGTTACCATTGTTAGGGCAAAAA
CTTTCTATGCTGGGAAAGCCAATGTTCCAGTTGCTGGTGTTAATGTACCT
GTTGTGGGTGGCCATGCAGGCATTACTATTCTGCCATTATTTTCTCAAGC
CACACCAAAAGCCAATCTTGATGATGATGTCATTAAGGCTCTTACAAAGA
GGACACAAGATGGAGGAACAGAAGTTGTAGAAGCTAAGGCTGGAAAGGGT
TCTGCAACTTTGTCAATGGCCTATGCTGGTGCCCTATTTGCTGATGCTTG
CCTTAAGGGCCTCAATGGAGTCCCAGATGTTGTGGAGTGCTCATTCGTGC
AATCCACTGTTACTGAACTTCCCTACTTTGCTTCCAAGGTGAGGCTTGGG
AAGAATGGAGTGGAGGAAGTTCTGGGCTTAGGACCTCTCTCAGATTTTGA
GCAACAAGGCCTCGAAAGCCTTAAGCCTGAACTCAAATCATCAATTGAGA
AGGGAATCAAATTTGCCAACCAGTAA
```

Tomato mMDH del 3 (SEQ ID NO: 136):
```
ATGTCAAGGACCTCCATGTTGAAATCCATCGTCCGCCGGAGCTCCACTGC
CGGAGCATCCTATGTATCTCGCCGTGGATTCGCATCGGGATCCGCGCCGG
AGAGGAAAGTTGCAGTTTTGGGGGCAGCCGGAGGGATTGGACAGCCTTTA
TCTCTTCTAATGAAGCTTAACCCTTTAGTATCCAGCCTTTCACTCTACGA
TATCGCCGGTACTCCCGGTGTTGCCGCCGATGTTAGTCACATCAACACCA
GATCTGAGGTTGCCGGTTTTGCAGGAGAAGAGCAGCTAGGGCAGGCACTG
GAAGGAGCTGATGTTGTTATCATTCCTGCTGGTGTGCCCCGAAAGCCTGG
TATGACCCGAGATGATCTGTTCAACATTAATGCGGGTATTGTTAAATCTC
TATGCACGGCCATTGCTAAGTACTGCCCCAATGCTCTGGTCAATATGATA
AGCAACCCAGTGAATTCCACTGTCCCTATTGCTGCTGAGGTGTTTAAGAA
AGCTGGAACTTATGATGAAAAGAAGCTCTTTGGAGTTACCATTGATGTGG
TTAGGGCCAAGACATTTTATGCTGGAAAAGCTAAAGTAAATGTTGCTGAG
GTCAATCTCCCAGTAGTTGGTGGTCATGCTGGCATAACTATCCTCCCATT
ATTTTCTCAAGCCACTCCAAAGGCAAATCTATCATATGAGGAAATTGTTG
CACTCACAAAGCGAACCCAAGATGGTGGGACAGAAGTTGTAGAAGCCAAA
GCTGGAAAGGGTTCAGCCACCCTCTCAATAGCCTATGCTGGGGCTATTTT
TGCCGATGCTTGCTTGAAGGGGTTGAATGGAGTTCCCGATGTTGTTGAAT
GTGCTTTTGTGCAGTCCAATGTCACCGAGCTTCCCTTCTTCGCATCCAAG
GTAAGACTTGGGAAAAATGGAGTGGAGGAAGTCCTAGGGTTGGGTCCACT
TAACGACTACGAGAAGCAAGGACTTGAGGCTCTTAAGCCAGAGCTGCTCT
CCTCCATTGAAAAGGGAATCAAGTTTGCCAAAGAAAACTAA
```

Tomato mMDH del 9 (SEQ ID NO: 137)
```
ATGTCAAGGACCTCCATGTTGAAATCCATCGTCCGCCGGAGCTCCACTGC
CGGAGCATCCTATGTATCTCGCCGTGGATTCGCATCGGGATCCGCGCCGG
AGAGGAAAGTTGCAGTTTTGGGGGCAGCCGGAGGGATTGGACAGCCTTTA
TCTCTTCTAATGAAGCTTAACCCTTTAGTATCCAGCCTTTCACTCTACGA
TATCGCCGGTACTCCCGGTGTTGCCGCCGATGTTAGTCACATCAACACCA
GATCTGAGGTTGCCGGTTTTGCAGGAGAAGAGCAGCTAGGGCAGGCACTG
GAAGGAGCTGATGTTGTTATCATTCCTGCTGGTGTGCCCCGAAAGCCTGG
TATGACCCGAGATGATCTGTTCAACATTAATGCGGGTATTGTTAAATCTC
TATGCACGGCCATTGCTAAGTACTGCCCCAATGCTCTGGTCAATATGATA
AGCAACCCAGTGAATTCCACTGTCCCTATTGCTGCTGAGGTGTTTAAGAA
AGCTGGAACTTATGATGAAAAGAAGCTCTTTGGAGTTACCATGGTTAGGG
CCAAGACATTTTATGCTGGAAAAGCTAAAGTAAATGTTGCTGAGGTCAAT
CTCCCAGTAGTTGGTGGTCATGCTGGCATAACTATCCTCCCATTATTTTC
TCAAGCCACTCCAAAGGCAAATCTATCATATGAGGAAATTGTTGCACTCA
CAAAGCGAACCCAAGATGGTGGGACAGAAGTTGTAGAAGCCAAAGCTGGA
AAGGGTTCAGCCACCCTCTCAATAGCCTATGCTGGGGCTATTTTTGCCGA
TGCTTGCTTGAAGGGGTTGAATGGAGTTCCCGATGTTGTTGAATGTGCTT
TTGTGCAGTCCAATGTCACCGAGCTTCCCTTCTTCGCATCCAAGGTAAGA
CTTGGGAAAAATGGAGTGGAGGAAGTCCTAGGGTTGGGTCCACTTAACGA
CTACGAGAAGCAAGGACTTGAGGCTCTTAAGCCAGAGCTGCTCTCCTCCA
TTGAAAAGGGAATCAAGTTTGCCAAAGAAAACTAA
```

Tomato mMDH del in NADH binding domain 1 (SEQ ID NO: 124)
```
ATGTCAAGGACCTCCATGTTGAAATCCATCGTCCGCCGGAGCTCCACTGC
```

-continued
```
CGGAGCATCCTATGTATCTCGCCGTGGATTCGCATCGGGATCCGCGCCGG

AGAGGAAAGTTGCAGTTTTGGGGGCAGCCGGAGGGATTGGACAGCCTTTA

TCTCTTCTAATGAAGCTTAACCCTTTAGTATCCAGCCTTTCACTCTACGA

TATCGCCGGTACTCCCGGTGTTGCCGCCGATGTTAGTCACATCAACACCA

GATCTGAGGTTGCCGGTTTTGCAGGAGAAGAGCAGCTAGGGCAGGCACTG

GAAGGAGCTGATGTTGTTATCATTCCTGCTGGTGTGCCCCGAAAGCCTGG

TACCCGAGATGATCTGTTCAACATTAATGCGGGTATTGTTAAATCTCTAT

GCACGGCCATTGCTAAGTACTGCCCCAATGCTCTGGTCAATATGATAAGC

AACCCAGTGAACTCCACTGTCCCTATTGCTGCTGAGGTGTTTAAGAAAGC

TGGAACTTATGATGAAAAGAAGCTCTTTGGAGTTACCATGCTTGATGTGG

TTAGGGCCAAGACATTTTATGCTGGAAAAGCTAAAGTAAATGTTGCTGAG

GTCAATCTCCCAGTAGTTGGTGGTCATGCTGGCATAACTATCCTCCCATT

ATTTTCTCAAGCCACTCCAAAGGCAAATCTATCATATGAGGAAATTGTTG

CACTCACAAAGCGAACCCAAGATGGTGGGACAGAAGTTGTAGAAGCCAAA

GCTGGAAAGGGTTCANCCACCCTCTCAATAGCCTATGCTGGGGCTATTTT

TGCCGATGCTTGCTTGAAGGGGTTGAATGGAGTTCCCGATGTTGTTGAAT

GTGCTTTTGTGCAGTCCAATGTCACCGAGCTTCCCTTCTTCGCATCCAAG

GTAAGACTTGGGAAAAATGGAGTGGAGGAAGTCCTAGGGTTGGGTCCACT

TAACGACTACGAGAAGCAAGGACTTGAGGCTCTTAAGCCAGAGCTGCTCT

CCTCCATTGAAAAGGGAATCAAGTTTGCCAAAGAAAACTAA
```

Construction of Plasmids Containing the Mutant mMDH Open Reading Frames

The plasmid pKG7495 containing the tomato mMDH ORF fused to a 6× His tag was digested with HindIII and XhoI restriction enzymes and the 5.8 kbps vector band was isolated from an agarose gel using the QIAGEN GEL ISOLATION KIT™ (Qiagen, Carlsbad, Calif.). Portions of the tomato mMDH sequence were synthesized (GeneArt) flanked by HindIII/XhoI sites. These sequences were missing a 3 bp sequence (nucleotides 543 to 545 deleted; SEQ ID NO:136) in the second NADH binding domain and corresponding to the mutations that were produced in the tomato plants by ZFN cleavage at these genomic locations. A second tomato mMDH mutation was synthesized on a HindIII/XhoI fragment missing 3 bps (nucleotides 353 to 355; SEQ ID NO:124) in the first NADH binding domain. All fragments were ligated into the pKG7495 vector and the clones were confirmed by sequencing. These constructs results in a series of tomato mutant mMDH clones with in-frame deletions in both of the NADH binding domains which were over expressed in a heterologous production system in E. coli.

Overexpression and Purification of Mitochondrial Malate Dehydrogenase (mMDH)

Wild type and mutant mMDH constructs were cloned into an E. coli expression vector. Vector DNA was transformed into ONE SHOT® BL21(DE3) chemically competent cells (Invitrogen). Target genes were cloned such that, when overexpressed, the resulting enzymes contained N-terminal hexahistine tags. Colonies were grown overnight at 37° C. on LB plates containing 100 µg/mL carbenecillin. A single colony was used to inoculate a 50 mL LB seed culture of the same media. The culture was grown overnight at 37° C. and was subsequently used to inoculate 1.2 L LB containing 100 100 µg/mL carbenecillin. For the wild-type mMDH enzymes the culture was induced with 1 mM IPTG at $OD_{600}$ of 0.6. Induction was allowed to proceed at 37° C. for 4 hours at which time the cells were harvest via centrifugation at 8,000 rpm for 15 minutes. All variants were place in an ice bath for 10 minutes and then induced with 200 µM IPTG for 18 hours at low temperature (19° C.).

Cell pellets were resuspended in 15-20 mL Buffer A (50 mM Tris-HCl pH 8.2, 300 mM NaCl, 10 mM imidazole, and 5% glycerol). Once solubilized protease inhibitor (Roche Complete Mini tablets) and lysozyme (1 mg/mL) were added. The solutions were allowed to stir for 20 minutes at 4° C. and were sonicated 4×1 minute bursts while on ice. Cell debris was removed by centrifugation (16,500 rpm for 45 minutes) at which time the crude lysate was applied to a 1 mL His Trap FF column equilibrated in Buffer A. Protein targets were eluted using a linear gradient from 0-100% Buffer B (50 mM Tris-HCl pH 8.2, 300 mM NaCl, 10 mM imidazole, and 5% glycerol) over 20 column volumes. Fractions containing mMDH were identified by SDS-PAGE analysis and activity assays. Positive fractions were pooled together and concentrated with an Amicon Ultrafiltration device equipped with a 10 kDa molecular weight cutoff membrane. The concentrated fractions were exchanged into Buffer A lacking imidazole using a PD 10 gel filtration. Protein concentrations were determined by theoretical molar extinction coefficients calculated using the Expasy Bioinformatics Resource Portal ProtParam tool. The desalted enzymes were flash frozen in liquid nitrogen and stored at −80° C. until further use. SDS-PAGE analysis demonstrated the molecular weights of the purified proteins corresponded to their calculated weights of ~37 kDa.

Specific Activities of Wild-Type and Mutant mMDHs

Figure 13:
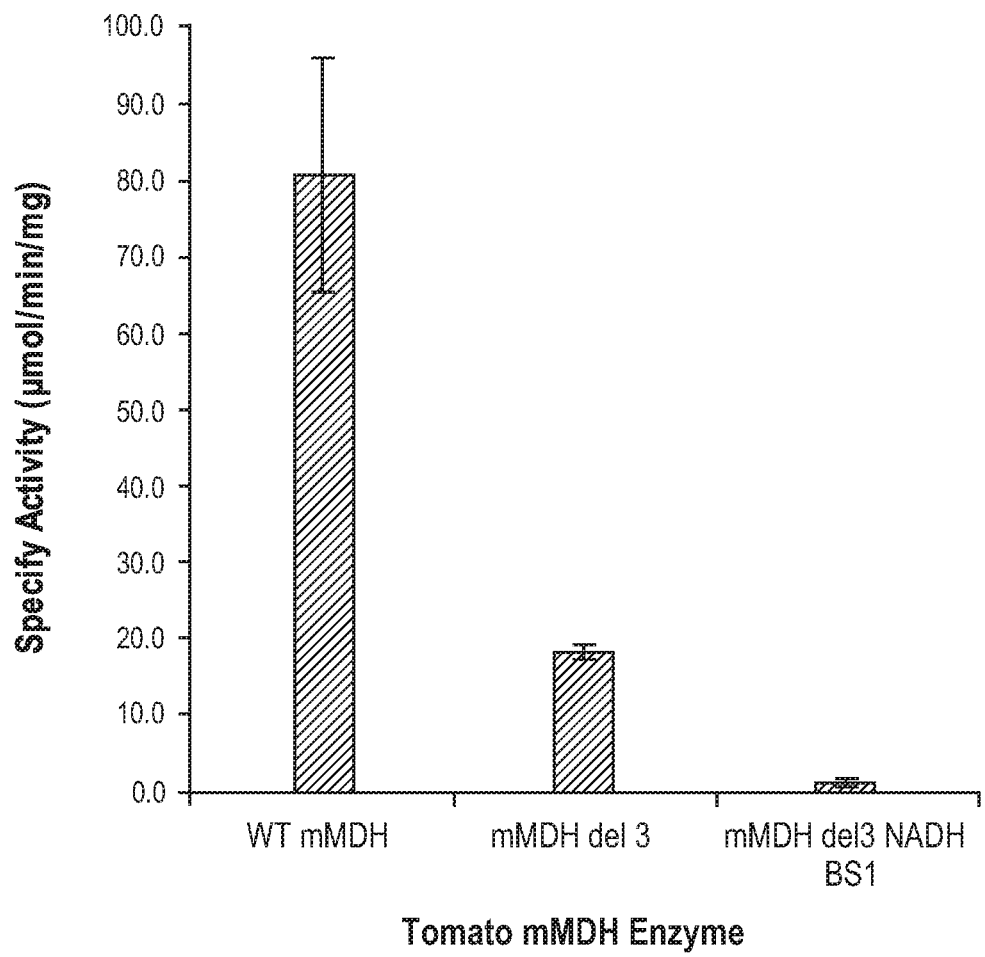
FIG. 13 is a table which depicts the specific activities of wild-type and two mutant tomato mMDH enzymes that were measured spectrophotometrically monitoring for NADH oxidation. The "mMDH del 3" mutation retains about 23% of the activity of the wild-type enzyme and the activity of the "mMDH del3 NADH BS1" mutation is significantly diminished at about 1.5% of the wild-type enzyme.

Enzyme assays were performed in a microplate reader at 35° C. and contained 100 mM Tris-HCl pH 8.2, 400 µM NADH, 0.0075-0.045 µM mMDH or mMDH mutant in a final volume of 200 µL. Reactions were incubated at 35° C. for 1 minute prior to initiation by the addition of oxaloacetate to a final concentration of 3 mM. Initial rates were determined spectrophotometrically monitoring for NADH oxidation (?340 nm). Rates were converted from mOD/min to µM min-1 using the molar extinction coefficient 6220 M−1 cm−1. The results of the enzyme assays are depicted in FIG. 13 and Table 5.

As shown, the specific activities of wild-type and two mutant tomato mMDH enzymes were measured spectrophotometrically monitoring for NADH oxidation. The mutation to the first NADH binding sequence encoded on SEQ ID NO:124 (labeled as "mMDH del3 NADH BS1" in Table 5 and FIG. 13) is significantly diminished and produces about 1.5% of the activity of the wild-type enzyme. Comparatively, the mutation of the second NADH binding sequence encoded on SEQ ID NO:136 (labeled as "mMDH del 3" in Table 5 and FIG. 13) retains about 23% of the activity of the wild-type enzyme. The mutations introduced within the NADH binding site in the mMDH enzyme result in reduced enzymatic activity, as a result the tomato plants which contain these mutations within the mMDH enzyme produce fruit with greater amounts of fresh weight.

TABLE 5

Enzyme kinetic assays which were completed on the mutated mMDH enzymes which are described as "mMDH del3" and "mMDH del3 NADH BS1". The mutations resulted in enzymes which had lower enzyme activity as compared to the wild type mMDH "WT mMDH".

| — | Average | Standard Deviation |
|---|---|---|
| WT mMDH | 80.4 | 15.11 |
| mMDH del 3 | 18.4 | 0.79 |
| mMDH del3 NADH BS1 | 1.1 | 0.46 |

| — | % WT Activity | |
|---|---|---|
| mDH del 3 | 22.9 | — |
| mMDH del3 NADH BS1 | 1.4 | |

Incorporation of Additional Mutations within the mMDH Enzyme Construction of Vectors for Heterologous Expression and Overexpression of Mitochondrial Malate Dehydrogenase (mMDH)

The isolated polynucleotide sequences which encode the native and mutated mMDH enzymes from tomato, soybean, and corn are introduced into vectors and transformed into microbial organisms for heterologous expression. Construction of plasmids containing the mutant mMDH open reading frames can be fused to a 6x His tag or other sequence used for isolation. Fragments of the mMDH polynucleotide sequence are synthesized. The fragments are flanked by restriction enzyme sites and can be readily cloned into a plasmid containing the mMDH open reading frame. The fragments are designed to contain mutations of about 3 bps, 4 bps, 5 bps, 6 bps, 7 bps, 8 bps, or 9 bps throughout the first and second NADH binding domain. In addition to these various mutations introduced into the second NADH binding domain of the mMDH open reading frame, the mutations that were produced in the tomato plants are incorporated into the isolated polynucleotide sequences which encode mMDH enzymes from tomato, soybean, and corn. As a result, a series of mutated mMDH coding sequences comprising in-frame deletions in both of the NADH binding domains are produced for the enzymes isolated from tomato, soybean, and corn.

Overexpression and Purification of Mitochondrial Malate Dehydrogenase (mMDH)

The plasmids containing the various mutations introduced within the coding sequence of tomato, soybean, and corn are transformed into chemically competent Escherichia coli cells. Transformed bacterial colonies are grown. A single colony is used to inoculate a seed culture. The culture is grown and is subsequently used to inoculate media. The cultures are induced and the growth of the culture is monitored using a spectrophotometer. Induction is allowed to proceed for a period of time until the cells are harvested.

The cultures are centrifuged and the resulting cell pellets are resuspended in a lysis buffer. The resuspended cell solutions are sonicated or lysed using other methods known to those with skill in the art. Cell debris is removed by centrifugation. Proteins are eluted. Fractions containing mMDH are identified by SDS-PAGE analysis and activity assays. Positive fractions are pooled together and concentrated. The concentrated fractions are desalted. Protein concentrations are determined using predicted molar extinction coefficients calculated using the Expasy Bioinformatics Resource Portal ProtParam tool. The desalted enzymes can be flash frozen in liquid nitrogen and stored at −80° C. until further use or assayed immediately.

Assessment of Wild-Type and Mutant mMDH Activity

Enzyme assays are performed in a final a cocktail which comprises a buffer, NADH, and purified mMDH enzyme (additional reagents are included as needed). The reaction is initiated by the addition of oxaloacetate (0-50 mM). Initial enzymatic rates are determined by spectrophotometrically monitoring for a decrease at 340 nm (NADH oxidation). Rates for the various mutations introduced into the mMDH enzyme are determined by converting to $\mu M\ min^{-1}$ using the molar extinction coefficient $6220\ M^{-1}\ cm^{-1}$. The alterations to the enzymes from the incorporation of the mutations results in modified substrate specificity of the mMDH enzyme. The mMDH enzyme catalyzes the biochemical reaction shown in FIG. 12, wherein the mMDH enzyme reversibly catalyzes the oxidation of malate to oxaloacetate using the reduction of NAD+ to NADH. Of the various mMDH enzymes tested, the mutations which produce the most favorable overall kinetic parameters ($k_{cat}$/Km values) are identified. These mutations result in an mMDH enzyme with reduced activity, as a result the plants which contain mutations to these mMDH enzymes produce seed and fruit with greater amounts of fresh weight.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A tomato plant cell comprising a homozygously modified endogenous mitochondrial malate dehydrogenase (mMDH) gene such that activity of the expressed mMDH protein is reduced in the plant cell, wherein
   (i) the endogenous mMDH comprises sequences as shown in SEQ ID NO:3-10;
   (ii) the modification is made following cleavage by a nuclease comprising a cleavage domain and a DNA-binding domain that binds to a target site within any one of SEQ ID NO:3-10; and
   (iii) the modification is within or between SEQ ID NO:3 and SEQ ID NO:4; within or between SEQ ID NO:5 and SEQ ID NO:6; within or between SEQ ID NO:7 and SEQ ID NO:8; or within or between SEQ ID NO:9 and SEQ ID NO:10.

2. The plant cell of claim 1, wherein the modification comprises a mutation in one or more NADH binding domains of the mMDH gene.

3. The plant cell of claim 1, wherein one or more alleles of mMDH are modified.

4. A plant part comprising the one or more modified plant cells of claim 1.

5. The plant part of claim 4, wherein the plant part is a leaf, stem, root, flower, seed, or fruit.

6. The plant cell of claim 1, wherein the modification is made using a nuclease comprising a pair of nucleases as follows:
   (i) a first nuclease comprising a cleavage domain and a DNA-binding domain that binds to a target sequence within SEQ ID NO:3 and a second nuclease comprising a cleavage domain and a zinc finger protein that binds to a target sequence within SEQ ID NO:4;
   (ii) a first nuclease comprising a cleavage domain and a DNA-binding domain that binds to a target sequence within SEQ ID NO:5 and a second nuclease comprising a cleavage domain and a zinc finger protein that binds to a target sequence within SEQ ID NO:6;
   (iii) a first nuclease comprising a cleavage domain and a DNA-binding domain that binds to a target sequence within SEQ ID NO:7 and a second nuclease comprising a cleavage domain and a zinc finger protein that binds to a target sequence within SEQ ID NO:8; and
   (iv) a first nuclease comprising a cleavage domain and a DNA-binding domain that binds to a target sequence within SEQ ID NO:9 and a second nuclease comprising a cleavage domain and a zinc finger protein that binds to a target sequence within SEQ ID NO:10.

7. The plant cell of claim 6, wherein the cleavage domain comprises a TypeIIS endonuclease cleavage domain or a Cas9 protein.

8. The plant cell of claim 7, wherein the nuclease comprises a zinc finger nuclease, a TALEN or a CRISPR/Cas nuclease system.

9. The plant cell of claim 8, wherein the zinc finger nuclease comprises first and second zinc finger nucleases, each zinc finger nuclease comprising a zinc finger protein having five or six zinc finger domains ordered finger 1 to finger 5 or finger 1 to finger 6, each zinc finger domain comprising a recognition helix region, wherein the zinc finger nuclease comprises the recognition helix regions ordered and shown as follows:
- a first zinc finger protein comprising:
  - F1: RSDTLSV (SEQ ID NO:23);
  - F2: DNSTRIK (SEQ ID NO:24);
  - F3: RSDHLSE (SEQ ID NO:25);
  - F4: TSGSLTR (SEQ ID NO:26);
  - F5: RSDALSR (SEQ ID NO:27); and
  - F6: TSGNLTR (SEQ ID NO:18), wherein the zinc finger protein binds to a target site as shown in SEQ ID NO:5; and
- (ii) a second zinc finger protein comprising:
  - F1: RSDNLAR (SEQ ID NO:29);
  - F2: QRGNRNT (SEQ ID NO:30);
  - F3: DSSDRKK (SEQ ID NO:31);
  - F4: DRSNLSR (SEQ ID NO:32); and
  - F5: LRHHLTR (SEQ ID NO:33), wherein the zinc finger protein binds to a target site as shown in SEQ ID NO:6.

10. The plant of claim 9, wherein the zinc finger nuclease comprises a non-canonical zinc finger domain.

11. The plant of claim 8, wherein the nuclease is introduced into the plant cell as a polynucleotide.

12. A method for producing a plant cell according to claim 1, the method comprising introducing one or more polynucleotides that express the nuclease into a plant cell such that the mMDH gene expression is reduced in the plant cell.

13. The method of claim 12, further comprising introducing an exogenous nucleic acid donor sequence into the cell, wherein the exogenous nucleic acid donor sequence is integrated into the mMDH gene following cleavage by the nuclease.

14. The method of claim 13, wherein the modification comprises a mutation in one or more NADH binding domains.

15. The method of claim 13, wherein the reduced MDH protein activity results in increased photosynthesis, modifications to the citric acid cycle within the plant cell, higher levels of malate in the plant cell, reduced oxaloacetate (OAA) levels in the cell and/or increased fruit yield.

16. A method of increasing crop yield, comprising planting a plant or plant part comprising the plant cell of claim 1, or a seed or plant part of the plant.

* * * * *